US009101568B2

(12) United States Patent
Pichichero et al.

(10) Patent No.: US 9,101,568 B2
(45) Date of Patent: Aug. 11, 2015

(54) COMPOSITIONS AND METHODS RELATED TO P6

(71) Applicants: Rochester General Hospital Research Institute, Rochester, NY (US); Michael Pichichero, Rochester, NY (US)

(72) Inventors: Michael Pichichero, Rochester, NY (US); M. Nadeem Khan, Rochester, NY (US); Ravinder Kaur, Pittsford, NY (US); Sharad Sharma, Rochester, NY (US); Janet Casey, Pittsford, NY (US); Lea Michel, Rochester, NY (US)

(73) Assignee: Rochester General Hospital Research Institute, Rochester, NY (US)

( * ) Notice: Subject to any disclaimer, the term of this patent is extended or adjusted under 35 U.S.C. 154(b) by 0 days.

(21) Appl. No.: 14/316,935

(22) Filed: Jun. 27, 2014

(65) Prior Publication Data

US 2014/0314803 A1  Oct. 23, 2014

Related U.S. Application Data

(63) Continuation of application No. 13/488,251, filed on Jun. 4, 2012, now abandoned.

(60) Provisional application No. 61/493,437, filed on Jun. 4, 2011.

(51) Int. Cl.
*A61K 39/00* (2006.01)
*A61K 39/02* (2006.01)
*A61K 39/102* (2006.01)
*G01N 33/68* (2006.01)

(52) U.S. Cl.
CPC .......... *A61K 39/102* (2013.01); *G01N 33/6854* (2013.01); *A61K 2039/57* (2013.01)

(58) Field of Classification Search
CPC .................................................... A61K 39/02
See application file for complete search history.

(56) References Cited

U.S. PATENT DOCUMENTS

| | | | |
|---|---|---|---|
| 4,868,116 A | 9/1989 | Morgan | |
| 4,879,213 A * | 11/1989 | Fox et al. | 435/5 |
| 4,980,286 A | 12/1990 | Morgan | |
| 5,011,686 A | 4/1991 | Pang | |
| 5,789,542 A | 8/1998 | McLaughlin | |
| 5,843,464 A | 12/1998 | Bakaletz | |
| 6,261,834 B1 | 7/2001 | Srivastava | |
| 2004/0009122 A1 | 1/2004 | Klaveness | |

FOREIGN PATENT DOCUMENTS

| | | |
|---|---|---|
| WO | 8804932 | 7/1988 |
| WO | 8907136 | 8/1989 |
| WO | 9002806 | 3/1990 |
| WO | 9315205 | 8/1993 |
| WO | 9400153 | 1/1994 |
| WO | 9412641 | 6/1994 |
| WO | 9426304 | 11/1994 |
| WO | 9517210 | 6/1995 |
| WO | 9602555 | 2/1996 |
| WO | 9633739 | 10/1996 |
| WO | 9701638 | 1/1997 |
| WO | 9964067 | 12/1999 |

OTHER PUBLICATIONS

Akkoyunia, et al., "Biological activity of serum antibodies to a nonacylated form of lipoprotein D of Haemophilus influenza", Infect Immun., 64:4586-92 (1996).
Avetisyan, et al., "Cell-mediated immune responses to influenza vaccination in healthy volunteers and allogeneic stem cell transplant recipients", Bone Marrow Transplant. 36 (5):411-5 (2005).
Avigan, et al., "Vaccination against infectious disease following hematopoietic stem cell transplantation", Biol.Blood Marrow Transplant., 7(3):171-83 (2001).
Badr, et al., "Immunization of mice with P6 of nontypeable Haemophilus influenzae: kinetics of the antibody response and IgG subclasses", Vaccine, 18:29-37 (1999).
Bagshawe, et al., "A cytotoxic agent can be generated selectively at cancer sites", Br. J. Cancer, 58:700-3 (1988).
Bagshawe, "The First Bagshawe lecture. Towards generating cytotoxic agents at cancer sites", Br. J. Cancer, 60:275-81 (1989).
Barenkamp, et al., "Outer membrane protein and biotype analysis of pathogenic nontypeable Haemophilus influenza", Infect Immun.,36:535-40 (1982).
Barnett, et al., "Immune response to pneumococcal conjugate and polysaccharide vaccines in otitis-prone and otitis-free children", Clin.Infect.Dis., 29(1):191-2 (1999).
Battelli, et al., "T lymphocyte killing by a xanthine-oxidase-containing immunotoxin", Cancer Immunol. Immunother., 35:421-5 (1992).
Blondelle and Houghten, "Design of model amphipathic peptides having potent antimicrobial activities", Biochem. 31: 12688-94 (1992).
Bogdan, et al., "Mapping of surface-exposed, conformational epitope of the P6 protein of Haemophilus influenza", Infect Immun., 63:4395-4401 (1995).
Burns, et al., "Vesicular stomatitis virus G glycoprotein pseudotyped retroviral vectors: concentration to very high titer and efficient gene transfer into mammalian and nonmammalian cells", PNAS, 90:8033-7 (1993).
Casey, et al:, "New patterns in the otopathogens causing acute otitis media six to eight years after introduction of pneumococcal conjugate vaccine", Pediatr Infect Dis J., 29: 304-9 (2010).
Chen, et al., "The Levels and Bactericidal Capacity of Antibodies Directed against the UspA1 and UspA2 Outer Membrane Proteins of Moraxella (Branhamella) catarrhatis in Adults and Children", Infect. Immun., 67: 1310-16 (1999).
Cripps and Otczyk, "Prospects for a vaccine against otitis media", Exp Rev Vaccines, 5: 517-34 (2006).
Daly, et al., "Neonatal intramuscular injection with recombinant adeno-associated virus results in prolonged beta-gluouronidase expression in situ and correction of liver pathology in mucopolysaccharidosis type VII mice", Hum Gene Ther., 10:85-94 (1999a).

(Continued)

*Primary Examiner* — Albert Navarro
(74) *Attorney, Agent, or Firm* — Pabst Patent Group LLP

(57) ABSTRACT

Disclosed are compositions and methods related to vaccination for AOM and children prone to AOM.

12 Claims, 21 Drawing Sheets

(56) References Cited

OTHER PUBLICATIONS

Daly, et al., "Neonatal gene transfer leads to widespread correction of pathology in a murine model of lysosomal storage disease", PNAS, 96:2296-2300 (1999b).

de Bree, et al., "Characterization of CD4+ memory T cell responses directed against common respiratory pathogens in peripheral blood and lung", J.Infect.Dis. 195(11):1718-25 (2007).

DeMaria et al., "Immunization with outer membrane protein P6 from nontypeable Haemophilus influenzae induces bacterioidal antibody and affords protection in the ohinohilia model of otitis media", Infect Immun., 64:5167-92 (1996).

De Roos, et al., "Mycardial infarct sizing and assessment of reperfusion by magnetic resonance imaging: a review", Int. J. Card. Imaging, 7:133-8 (1991).

Dull, et al., "A Third-generation lentivirus vector with a conditional packaging system", J. Virol., 72(11):8463-71 (1998).

Emonts, et al., "Genetic polymorphisms in immunoresponse genes TNFA, IL6, IL10, and TLR4 are associated with recurrent acute otitis media", Pediatrics, 120(4):814-23 (2007).

Faden, "The microbiologic and immunologic basis for recurrent otitis media in children", Eur.J.Pediatr., 160(7):407-13 (2001).

Faden, et al., "Epidemiology of nasopharyngeal colonization with nontypable Haemophilus influenzae in the first 2 years of life", J Infect Dis., 172:132-5 (1995).

Faden, et al., "Otitismedia in children. I. The Systemicimmuneresponse to nontypable Haemophilus influenza", J Infect Dis., 1999;160:999-1004 (1999).

Fazilleau, et al., "Follicular helper T cells: lineage and location", Immunity., 30(3):324-35 (2009).

Forsgreen, et al., "Protein D of Haemophilus influenzae: A protective Nontypeable H. influenzae antigen and a carrier for pneumococcal vaccines", Clin. Infect Dis., 46:726-31 (2008).

Harabuchi, et al., "Nasopharyngeal colonization with nontypeable Haemophilus influenzae and recurrent otitis media. Tonawanda/Williamsville Pediatrics", J Infect Dis.,170(4):862-6 (1994).

Hughes, et al., "Monoclonal antibody targeting of liposomes to mouse lung in vivo", Cancer Res., 49:6214-20, (1989).

Javadpour, et al., "De novo antimicrobial peptides with low mammalian cell toxicity", J. Med. Chem. 39:3107-13 (1996).

Kaur, et al., "Serum antibody response to three non-typeable Haemophilus influenzae outer membrane proteins during acute otitis media and naeopharyngeal colonization in otitis prone and non-otitis prone children", Vaccine, 29:1023-8 (2011).

King, et al., "Adaptive immunity to nontypeable Haemophilus influenza", Am.J.Respir.Crit Care Med., 167(4):587-92 (2003).

Kodama, et al., "Cellular immune response of adenoidal and tonsillar lymphocytes to the P6 outer membrane protein of non-typeable Haemophilus influenzae and its relation to otitis media", Acta Otolaryngol., 119(3):377-83 (1999).

Kordower, et al., "Lentiviral gene transfer to the nonhuman primate brain", Exp Neurol., 160:1-16 (1999).

Kyd and Cripps, "Nontypeable Haemophilus influenzae: challenges in developing a vaccine", J Biotechnol.,73:103-8 (1999).

Kyd and Cripps, "Potential of a novel protein, OMP26, from nontypeable Haemophilus influenzae to enhance pulmonary clearance in a rat model", Infect Immun., 66:2272-8 (1998).

Kyd, et al., "Efficacy of the 26-kilodalton outer membrane protein and two P5 fimbrin-derived immunogens to induce clearance of nontypeable Haemophilus influenzae from the rat middle ear and lungs as well as from the chinchilla middle ear and nasopharynx", Infect Immun., 71:4591-9 (2003).

Lamoreaux, et al., "Intracellular cytokine optimization and standard operating procedure", Nat.Protoc., 1(3):1507-16 (2006).

Lipschutz, et al., "Analysis of membrane traffic in polarized epithelial cells",Curr. Protoc Cell Biol.,15:5 ( 2001).

Litzinger and Huang, "Biodistribution and immunotargetability of ganglioside-stabilized dioleoylphosphatidylethanolamine liposomes", Biochim Biophys Acta, 1104:179-87, (1992).

Loeb and Smith, "Outer membrane protein composition in disease isolates of Haemophilus influenzae: pathogenic and epidemiological implications", Infect Immun., 30:709-17 (1980).

Malley, et al., "Antibody-independent, interleukin-17A-mediated, cross-serotype immunity to pneumococci in mice immunized intranasally with the cell wall polysaccharide",Infect.Immun., 74(4):2187-95 (2006).

Maloy and Kari, "Structure-activity studies on magainins and other host defense peptides", Biopolymers, 37:105-22 (1995).

Mancheno, et al., "A peptide of nine amino acid residues from alpha-sarcin cytotoxin is a membrane-pertubing structure", J. Pept. Res., 51:142-8 (1998).

Maslanka, et al., "Age-dependent Neisseria meningitidis serogroup C class-specific antibody concentrations and bactericidal liters in sera from young children from Montana immunized with a licensed polysaccharide vaccine", Infect. Immun. 66: 2453-9 (1998).

Mattila, et al., "Adenoids provide a microenvironment for the generation of CD4(+), CD45RO(+), L-selectin(−), CXCR4(+), CCR5(+) T lymphocytes, a lymphocyte phanotype found in the middle ear effusion", Int. Immunol., 12(9):1235-43 (2000).

McCormack, et al., "Factors affecting long-term expression of a secreted transgene product after intravenous administration of a retroviral vector", Mol. Ther., 3:516-25 (2001).

McCrea, et al., "Relationships of nontypeable Haemophilus influenzae strains to hemolytic and nonhemolytic Haemophilus haemolyticus strains,", J. Clin. Microbiol. 46:406-16 (2008).

Morgan and Gainor, "Approaches to the Discovery of Non-Peptide Ligands for Peptide Receptors and Peptidases", Ann. Rep. Med. Chem. 24:243-2 (1989).

Morita, et al., "Human blood CXCR5(+)CD4(+) T cells are counterparts of T follicular cells and contain specific subsets that differentially support antibody secretion", Imunity, 34(1):108-21 (2011).

Mulligan, "The basic science of gene therapy", Science, 260:926-32 (1993).

Muralidhar, et al., "Global microRNA profiles in cervical squamous cell carcinoma depend on Drosha expression levels", J Pathol., 212(4):368-77 (2007).

Mureithi, et al., "T cell memory response to pneumococcal protein antigens in an area of high pneumococcal carriage and disease", J.Infect.Dis., 200(5):783-93 (2009).

Murphy, et al., "A subtyping system for nontypable Haemophilus influenzae based on outer-membrane proteins", J Infect Dis., 147:838-46 (1983).

Murphy, et al., "Haemophilus haemplyticus: a human respiratory tract commensal to be distinguished from Haemophilus influenza", J Infect Dis., 195:81-9 (2007).

Murphy, et al., "Identification of a 16,600-dalton outer membrane protein on nontypeable Haemophilus influenzae as a target for human serum bactericidal antibody",. J Clin Invest, 78(4):1020-7 (1986).

Murphy, et al., "Identification of a specific epitope of Haemophilus influenzae on a 16,600-dalton outer membrane protein", J Infect Dis. 152:1300-7 (1985).

Neary, et al., "Antibodies to Loop 6 of the P2 Porin Protein of Nontypeable Haemophilus influenzae are Bactericidal against Multiple Strain", Infect Immunity, 69:773-778 (2001).

Nelson, et al., "Molecular conservation of the P6 outer membrane protein among strains of Haemophilus influenzae: analysis of antigenic determinants, gene sequences, and restriction fragment length polymorphisms", Infect Immun., 59:2658-63 (1991).

Nomura, et al., "Promiscuous peptides on the nontypeable Haemophilus influenzae P6 outer membrane protein", J Clin. Immunol., 28(4):361-9 (2008).

Novotny, et al., "Epitope mapping of the outer membrane protein P5-homologous fimbrin adhesin of nontypeable Haemophilus influenza", Infect Immun., 68(4):2119-28 (2000).

Parsons, et al., "Peptidoglycan recognition by Pal, an outer membrane lipoprotein", Biochemistry, 45:2122-28 (2006).

Pichichero, et al., "Antibody response to Haemophilus influenzae outer membrane protein D, P6, and OMP26 after nasopharyngeal colonization and acute otitis media in children", Vaccine, 28(44):7184-92 (2010).

(56) References Cited

OTHER PUBLICATIONS

Pietersz and McKenzie, "Antibody conjugate for the treatment of cancer", Immunol. Rev., 129:57-80, (1992).

Poeschla, et al., "CXCR4 is required by a nonprimate lentivirus: heterologous expression of feline immunodeficiency virus in human, rodent, and feline cells", J Virol., 72(8):6858-66 (1998).

Pollard and Levin, "Production of low-avidity antibody by infants after infection with serogroup B meningococci", Lancet, 356: 2065-6 (2000).

Powers, et al., "Indium-111 platelet scintigraphy in cerebrovascular disease", Neurology, 32:938-43 (1982).

Prellner, et al., "Response to rubella tetanus, and diphtheria vaccines in otitis-prone and non-otitis-prone children", Ann.Otol.Rhinol. Laryngol., 99(8):628-32 (1990).

Prymula, et al., "Pneumococcal capsular polysaccharides conjugated to protein D for prevention of acute otitis media caused by both Streptococcus pneumoniae and non-typable Haemophilus influenzae: a randomised double-blind efficacy study", Lancet, 367:749-8 (2008).

Rapola, et al., "Antibody response to pneumococcal proteins pneumococcal surface adhesin A and pneumolysin in children with acute otitis media",. Pediatr Infect Dis J., 20:482-7 (2001).

Revai, et al., "Association between cytokine gene polymorphisms and risk for upper respiratory tract infection and acute otitis media", Clin.Infect.Dis., 49(2):257-61 (2009).

Roffler, et al., "Anti-neoplastic glucuronide prodrug treatment of human tumor cells targeted with a monoclonal antibody-enzyme conjugate", Biochem. Pharmacol, 42:2062-5, (1991).

Saberwal and Nagaraj, "Cell-lytic and antibacterial peptides that act by pertubing the barrier function of membranes: facets fo their conformational features, structure-function correlations and membrane-perturbing abilities", Biochim. Biophys. Acta. 1197:109-31 (1994).

Sabirov, et al., "Breast-feeding is associated with a reduced frequency of acute otitis media and high serum antibody levels against NTHI and outer membrane protein vaccine antigen candidate P6", Pediatr Res., 66(5):565-70 (2009).

Samukawa, et al., "Immune response to specific antigens of Streptococcus pneumoniae and Moraxella catarrhalis in the respiratory tract", Infect Immun., 68:1569-73 (2000).

Senter, et al., "Generation of 5-fluorouracil from 5-fluorocytosine by monoclonal antibody-cytosine deaminase conjugates", Bioconjugate Chem., 2:447-51 (1991).

Senter, et al., "Generation of cytotoxic agents by targeted enzymes", Bioconjugate Chem., 4:3-9 (1993).

Shurin, et al., "Bactericidal antibody and susceptibility to otitis media caused by nontypable strains of Haemophilus influenza", J Pediatr., 97(3):364-9 (1980).

Sikkema and Murphy, "Molecular analysis of the P2 porin protein of nontypeable HaemPPophilus influenza", Infect Immunity, 60: 5204-11 (1992).

Skotnicka, et al., "Lymphocyte subpopulations in middle ear effusions: flow cytometry analysis", Otol.Neurotol., 26(4):567-71 (2005).

Spinola, et al., "Epidemiology of colonization by nontypable Haemophilus Influenzae in children: a longitudinal study", J Infect Dis., 154(1):100-9 (1986).

St. Geme, "The pathogenesis of nontypable Haemophilus influenzae otitis media", Vaccine, 19(1):S41-50 (2001).

Tarantal, et al., "Rhesus monkey model for fetal gene transfer: studies with retroviral-based vector systems", Mol. Ther., 3:128-38 (2001).

Thakur, et al., "Indium-LLL labeled platelets: studies on preparation and evaluation of in vitro and in vivo functions", Throm Res., 9:345-57 (1976).

Virolainen, et al., "Comparision of serum antibodies to pneumolysin with those to pneumococcal capsular polysaccharides in children with acute otitis media", Pediatr Infect Dis J, 15:128-33 (1996).

Yamanaka and Faden, "Antibody response to outer membrane protein of nontypeable Haemophilus influenzae in otitis-prone children", J Pediatr., 122:212-8 (1993).

Yu and Vinuesa, "The elusive identity of T follicular helper cells", Trends Immunol., 31(10):377-83 (2010).

Zhang, et al., "Low CD4 T cell immunity to pneumolysin is associated with nasopharyngeal carriage of pneumococci in children", J.Infect.Dis., 195(8):1194-202 (2007).

Zinkernagel, "Maternal Antibodies, Childhood Infections, and Autoimmune Diseases", NEJM, 2001; 345: 1331-5 (2001).

* cited by examiner

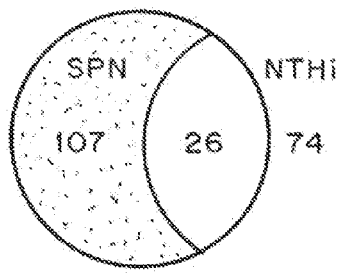

A. Differentially expressed genes (PBMC) with AOM due to Spn (>2 fold)

| Gene Family | #Regulated genes | % Up-regulated | %Down-regulated |
|---|---|---|---|
| Cytokines & chemokines | 21 | 9 | 12 |
| Complement | 7 | 6 | 1 |
| TLR | 5 | 3 | 2 |
| T cell response | 19 | 5 | 14 |
| Cell adhesion | 43 | 29 | 14 |
| Apoptosis | 29 | 19 | 10 |
| Inflammatory response | 23 | 22 | 1 |
| Response to bacteria | 18 | 12 | 6 |

B. Differentially expressed genes (PBMC) with AOM due to NTHi (>2 fold)

| Gene Family | #Regulated genes | %Up-regulated | %Down-regulated |
|---|---|---|---|
| Cytokines & chemokines | 20 | 3 | 17 |
| Complement | 8 | 6 | 2 |
| TLR | 1 | 0 | 1 |
| Response to bacteria | 20 | 9 | 11 |
| T cell response | 19 | 11 | 8 |
| Cell adhesion | 5 | 3 | 2 |
| Apoptosis | 23 | 12 | 11 |
| Inflammatory response | 13 | 3 | 10 |

FIG. 8

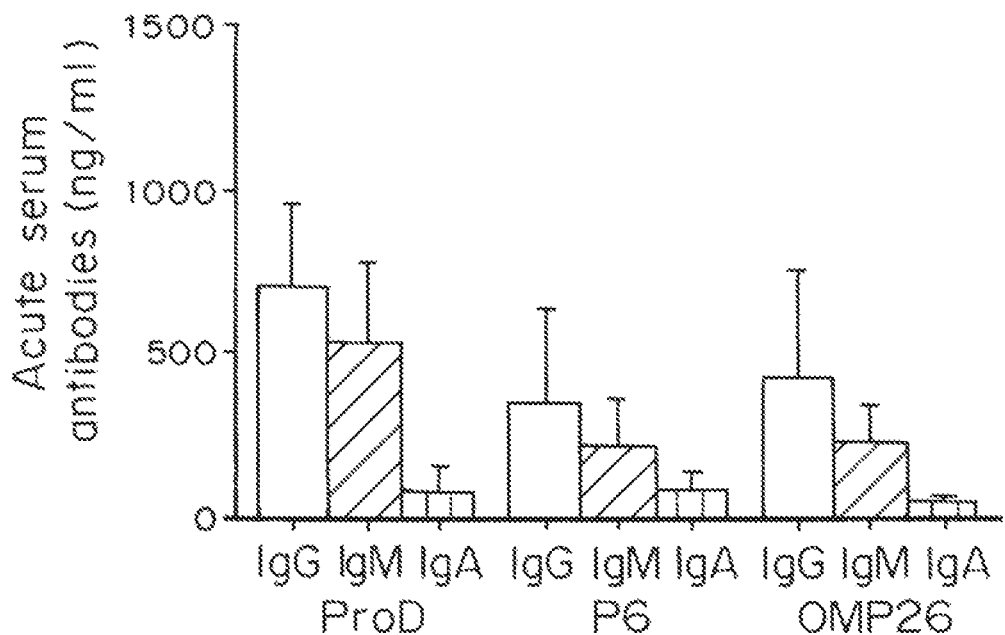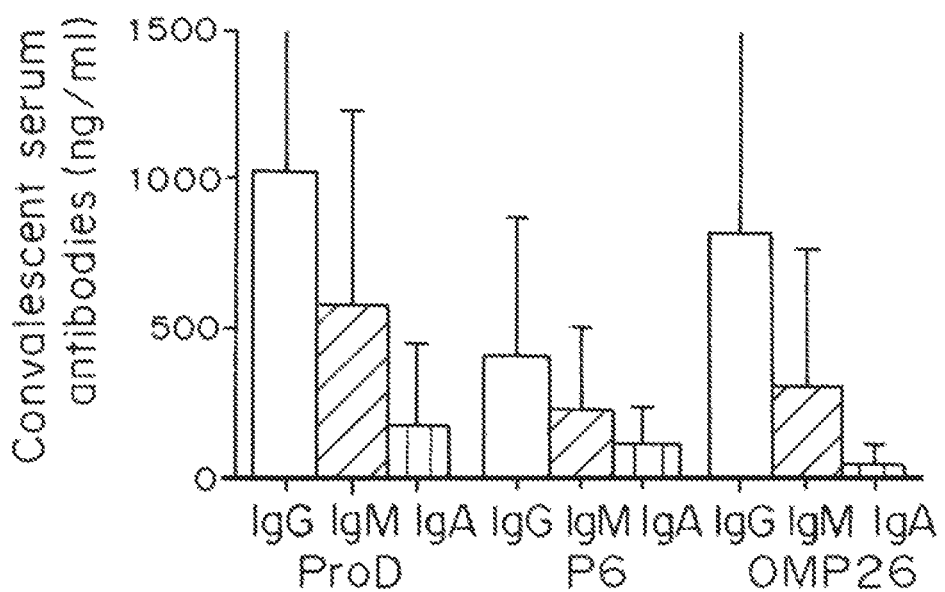
FIG. 13

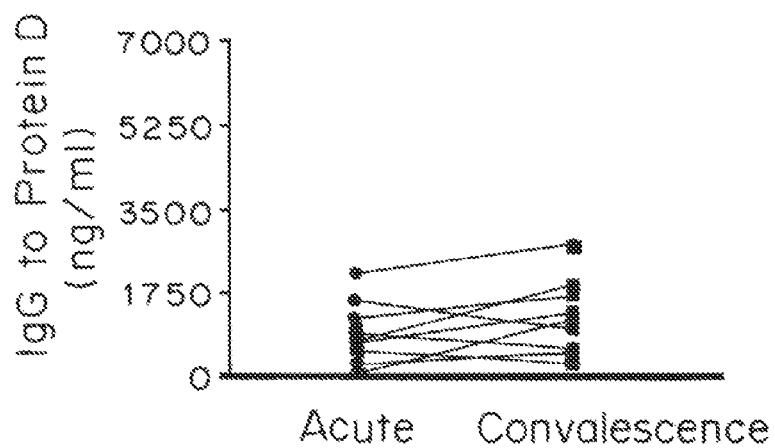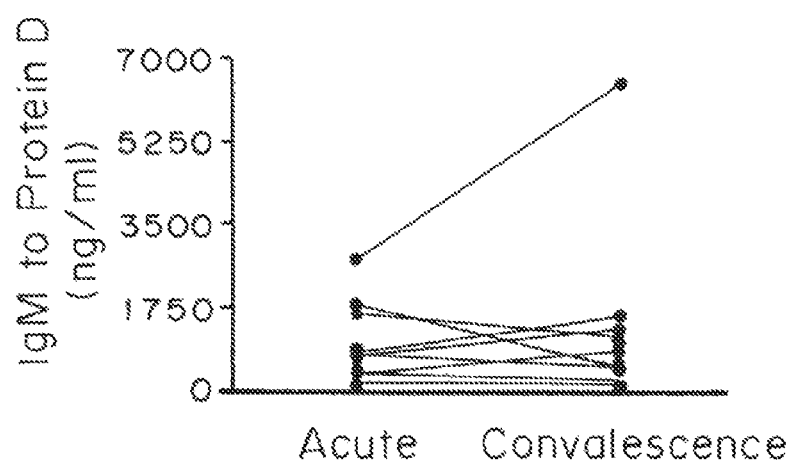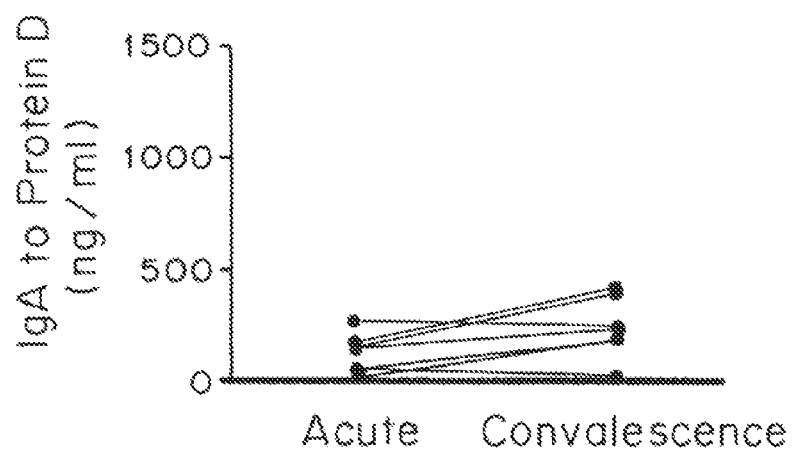
FIG. 14A

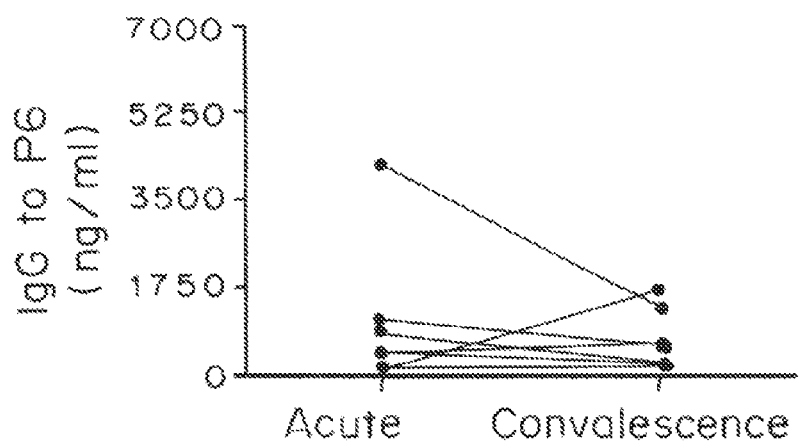
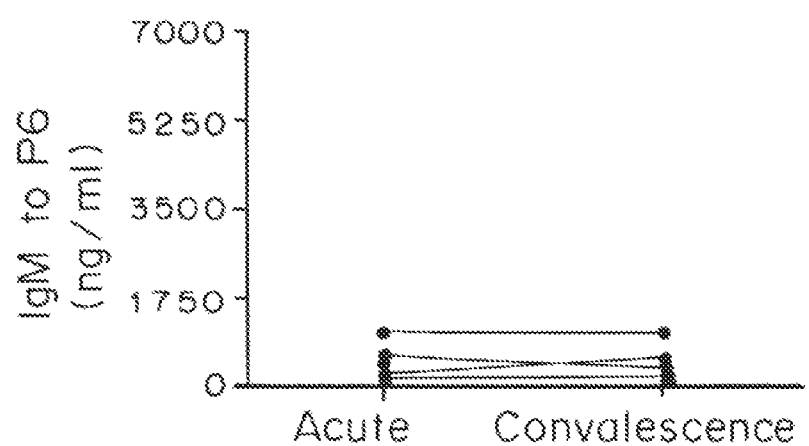
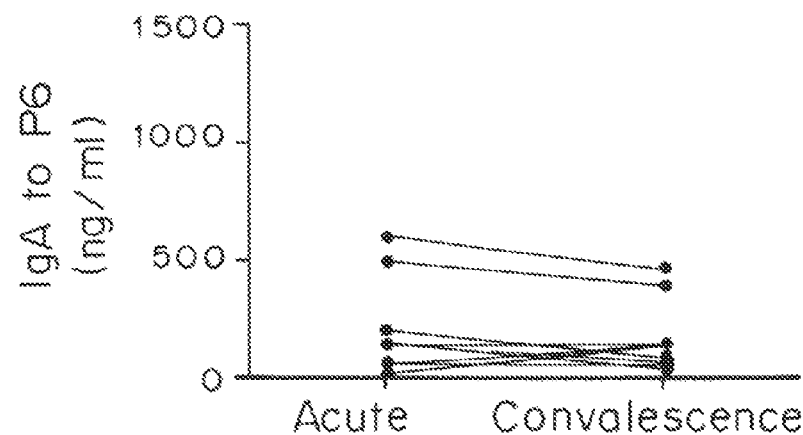
FIG. 14B

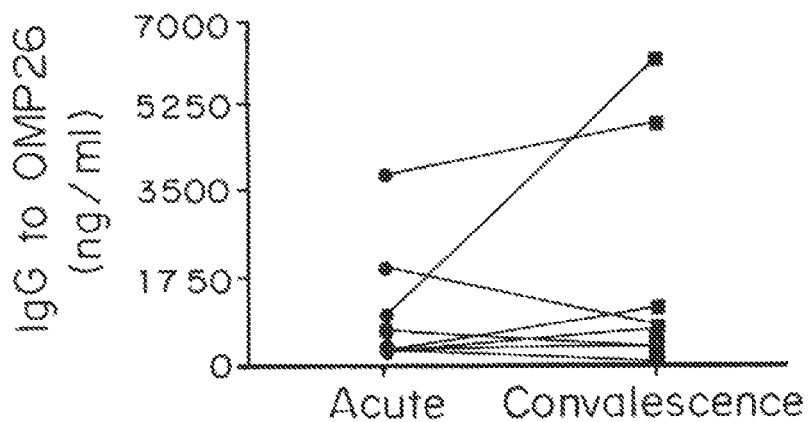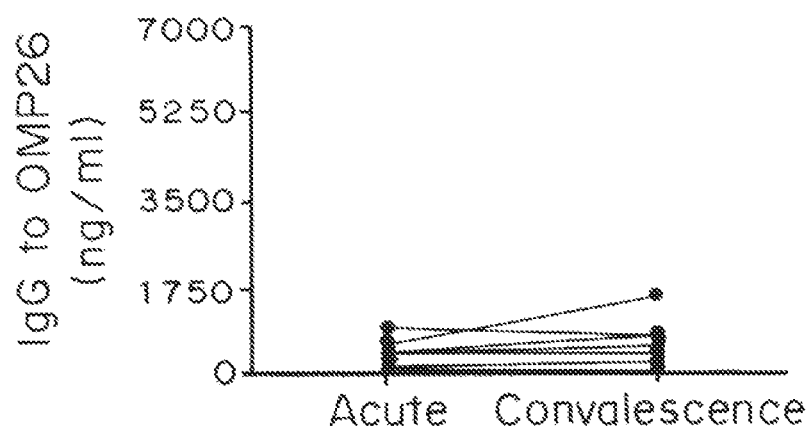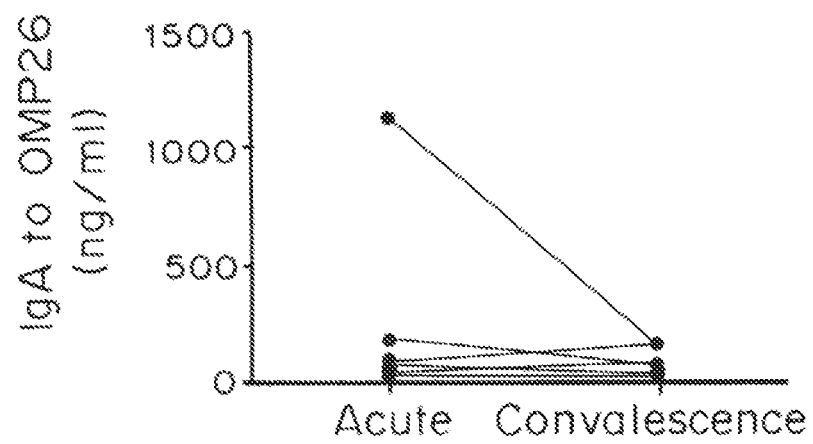
FIG. 14C

SEQUENCE LISTING

```
<160> NUMBER OF SEQ ID NOS: 1

<210> SEQ ID NO 1
<211> LENGTH: 153
<212> TYPE: PRT
<213> ORGANISM: Haemophilus influenzae

<400> SEQUENCE: 1

Met Asn Lys Phe Val Lys Ser Leu Leu Val Ala Gly Ser Val Ala Ala
1               5                   10                  15

Leu Ala Ala Cys Ser Ser Ser Asn Asn Asp Ala Ala Gly Asn Gly Ala
            20                  25                  30

Ala Gln Thr Phe Gly Gly Tyr Ser Val Ala Asp Leu Gln Gln Arg Tyr
        35                  40                  45

Asn Thr Val Tyr Phe Gly Phe Asp Lys Tyr Asp Ile Thr Gly Glu Tyr
    50                  55                  60

Val Gln Ile Leu Asp Ala His Ala Ala Tyr Leu Asn Ala Thr Pro Ala
65                  70                  75                  80

Ala Lys Val Leu Val Glu Gly Asn Thr Asp Glu Arg Gly Thr Pro Glu
                85                  90                  95

Tyr Asn Ile Ala Leu Gly Gln Arg Arg Ala Asp Ala Val Lys Gly Tyr
            100                 105                 110

Leu Ala Gly Lys Gly Val Asp Ala Gly Lys Leu Gly Thr Val Ser Tyr
        115                 120                 125

Gly Glu Glu Lys Pro Ala Val Leu Gly His Asp Glu Ala Ala Tyr Ser
    130                 135                 140

Lys Asn Arg Arg Ala Val Leu Ala Tyr
145                 150
```

COMPOSITIONS AND METHODS RELATED TO P6

CROSS-REFERENCE TO RELATED APPLICATIONS

This application is a Continuation of U.S. application Ser. No. 13/488,251, filed Jun. 4, 2012, which claims benefit of U.S. Provisional Application No. 61/493,437, filed Jun. 4, 2011. Application Ser. No. 13/488,251, filed Jun. 4, 2012, and Application No. 61/493,437, filed Jun. 4, 2011, are hereby incorporated herein by reference in their entirety.

STATEMENT REGARDING FEDERALLY SPONSORED RESEARCH OR DEVELOPMENT

This invention was made with Government Support under RO1 08671 by the National Institutes of Health and National Institute on Deafness and Other Communication Disorders. The Government has certain rights in the invention.

REFERENCE TO SEQUENCE LISTING

The Sequence Listing submitted Jun. 27, 2014 as a text file named "RGH_101_CON_AMD_AFD_Sequence_Listing.txt," created on Jun. 27, 2014, and having a size of 1,725 bytes, is hereby incorporated by reference pursuant to 37 C.F.R. §1.52(e)(5).

FIELD OF THE INVENTION

The field of the invention is compositions, methods and kits related to therapies Acute Otitis Media (AOM) and other respiratory diseases and disorders caused by the bacteria non-typeable *Haemophilus influenzae* (NTHi).

BACKGROUND OF THE INVENTION

Acute Otitis Media (AOM) is the most common infectious disease among children to cause parents to seek medical care for their child. Children receive antibiotics to treat AOM which increases the emergence of antibiotic resistant bacteria. Temporary hearing loss is the most common complication; rarely there are intracranial complications. WHO estimates that 51,000 deaths/year are attributable to AOM in children younger than 5 years old and that chronic AOM (occurring in 65-330 million people) is the major cause of hearing loss in developing countries. Nontypeable *Haemophilus influenzae* (NTHi) bacteria accounts for 40-60% of AOM and recurrent AOM. A similar percentage of cases of acute sinusitis and rhinosinusitis, acute exacerbations of chronic bronchitis and acute pneumonia (in the developing world) are caused by NTHi.

Otitis prone (OP) children are defined as children with recurrent AOM, with at least 3 episodes in 6 months or 4 episodes in a 12-month time span. Each episode of AOM is typically followed by 4-12 weeks of otitis media with effusion (OME) during which time the child has diminished hearing and this often leads to temporary delayed speech and language development and can be associated with permanent hearing loss. Non otitis prone (NOP) children experience no ear infections or few ear infections, not meeting the OP definition. In the US alone, the economic burden of otitis media exceeded $5 billion/year in 1997 in medical treatment, surgical management, and loss of income for working parents. Thus, the impact on health costs and on lifestyle for the child and parents is very meaningful. OP children eventually lose their propensity to experience AOM, usually by age 5 years.

Due to the large costs related to AOM, there is a need for an effective preventive or prophylactic treatment. OP children do not always generate an efficient immune response and thus a vaccine that generates an immune response that efficiently destroys the pathogen is needed.

The disclosed invention provides a vaccine that produces humoral and cell mediated responses to NTHi for preventing ear infections, sinus infections, acute exacerbations of bronchitis and pneumonia. The invention provides epitopes that are of importance for generating an effective immune response to NTHi.

The invention further provides methods of vaccinating individuals with an effective NHTi vaccine.

SUMMARY OF THE INVENTION

Disclosed are compositions and methods related to Acute Otitis Media (AOM). For example, disclosed are epitopes for an immunization against Nontypeable *Haemophilus influenzae* (NTHi), selected from the group of peptides of 3B9, 7F3 and 4G4, or mixtures thereof.

Also disclosed are vaccines comprising one or more of the epitopes. Also disclosed are vaccines for inhibiting infection comprising the epitope of claim 1, in combination with an antigenic pharmaceutical carrier. Also disclosed are vaccines comprising P6 at a concentration of at least 1.1, 1.2, 1.3, 1.5, 1.7, 1.9, 2.0, 2.5, 3.0, 5, 7, or 10 fold the P6 and P6 epitope of a vaccine having P6, protein D, and OMP24 present in them. Also disclosed are vaccines comprising P6, or an epitope of claim 1, or mixture there of, wherein the vaccine comprises a concentration of antigen greater than 1.1, 1.2, 1.3, 1.5, 1.7, 1.9, 2.0, 2.5, 3.0, 5, 7, or 10 fold the P6 and P6 epitope antigen of a vaccine having P6, protein D, and OMP24 present in them. Also disclosed are vaccines comprising P6 and Protein D, epitopes of P6 or Protein D, or mixtures thereof, but not OMP26 of non typeable *Haemophilus influenzae* (NTHi).

Also disclosed are methods for screening patients for Nontypeable *Haemophilus influenzae* (NTHi) infection comprising reacting a biological sample with the epitopes of claim 1. Also disclosed are methods for treating patients for Nontypeable *Haemophilus influenzae* (NTHi) comprising administering to the patient an epitope of claim 1, or mixtures thereof, in an amount effective to inhibit a Nontypeable *Haemophilus influenzae* (NTHi) infection. Also disclosed are methods for vaccinating a host against a Nontypeable *Haemophilus influenzae* (NTHi) infection comprising providing the epitope of claim 1 in combination with an antigenic pharmaceutical carrier. Also disclosed are methods of vaccination, said method comprising step of administering therapeutically effective dose of the vaccine of claim 23 to a subject in need thereof. Also disclosed are methods of treating a child, comprising identifying a child wherein the child is prone to having acute otitis media (AOM) and administering the vaccine of claim 34 to the child.

Also disclosed are kits for vaccination, the kit comprising a vaccine in a deliverable form.

The epitopes can be reactive with anti-P6 polyclonal antibodies. The epitopes can be used in combination with a pharmaceutical carrier for administration to a subject. The epitopes can be used in an effective concentration for administration to a subject to neutralize Nontypeable *Haemophilus influenzae* (NTHi). The epitopes can further comprise a pharmaceutical carrier for administration to a patient, wherein the carrier and concentration of sequences elicit an immune response when administered to a subject. The epitopes can be labeled with a compound selected from the group consisting of dyes, fluorescent labels, chemiluminescent labels, enzymes, and radioactive labels. The epitopes can be immobilized onto a substrate. The epitopes can be used at a concentration of at least 1.1, 1.2, 1.3, 1.5, 1.7, 1.9, 2.0, 2.5, 3.0, 5, 7, or 10 fold the P6 and P6 epitope of a vaccine having P6, protein D, and OMP24 present in them.

The vaccines can comprise one or more of the epitope. The vaccines can comprise one or more of the epitopes and P6 at a concentration of at least 1.1, 1.2, 1.3, 1.5, 1.7, 1.9, 2.0, 2.5, 3.0, 5, 7, or 10 fold the P6 and P6 epitope of a vaccine having P6, protein D, and OMP24 present in them. The vaccines can be in a capsular form. The vaccines can consist of P6 or P6 epitopes.

The methods can use epitopes labeled with a compound selected from the group consisting of dyes, fluorescent labels, chemiluminescent labels, enzymes, and radioactive labels. The methods can use epitopes immobilized onto a substrate. The methods can further comprise predicting the prognosis of the patient based on the reactivity of the patient sample with the epitopes. The methods can use epitopes that act as a vaccine against Nontypeable *Haemophilus influenzae* (NTHi) infection. The methods can treat patients and subjects having Nontypeable *Haemophilus influenzae* (NTHi), having a Nontypeable *Haemophilus influenzae* (NTHi) ear infection, and/or prone to having Nontypeable *Haemophilus influenzae* (NTHi).

The methods can administer the vaccines through an oral route or intra peritoneal route. The methods can administer the vaccines in capsular form. The methods can administer the vaccines at a dosage ranging from 0.01 mg/ml/kg to 100 mg/ml/kg. The methods can use vaccines capable of inhibiting a Nontypeable *Haemophilus influenzae* (NTHi) infection in a subject prone to Nontypeable *Haemophilus influenzae* (NTHi), to a greater extent than a vaccine comprising Protein D or OMP26.

BRIEF DESCRIPTION OF THE DRAWINGS

FIG. 1A is a graph of the bactericidal titers against homologous and heterologous NTHi strains elicited in children with AOM. FIG. 1B is a graph of the comparison of anti P6 ELISA titers in bactericidal and non bactericidal sera elicited in children with AOM. FIG. 1C is a graph of the comparison of anti Protein D ELISA titers in bactericidal and non bactericidal sera elicited in children with AOM. FIG. 1D is a graph of the whole cell ELISA titers against bactericidal and non bactericidal sera elicited in children with AOM.

FIG. 8 is a comparison of differentially expressed immune response related genes obtained from PBMCs of children (18 months old) with Spn or NTHi induced AOMs expressed relative to their respective healthy control visits. Genes regulated greater than 2 fold are represented.

FIG. 13 shows graphs of IgG, IgM and IgA antibody levels comparison to NTHi outer membrane proteins D, P6 and OMP26 in acute (top) and convalescent (bottom) sera of 9 children with NTHi AOM. Antibodies concentrations were summarized as geometric mean concentration with 95% confidence intervals.

FIGS. 14A, 14B and 14C are graphs of individual IgG, IgM and IgA antibody levels to NTHi outer membrane proteins D (A), P6 (B) and OMP26 (C) in acute and convalescent sera of 9 children with NTHi AOM.

Figure 15:
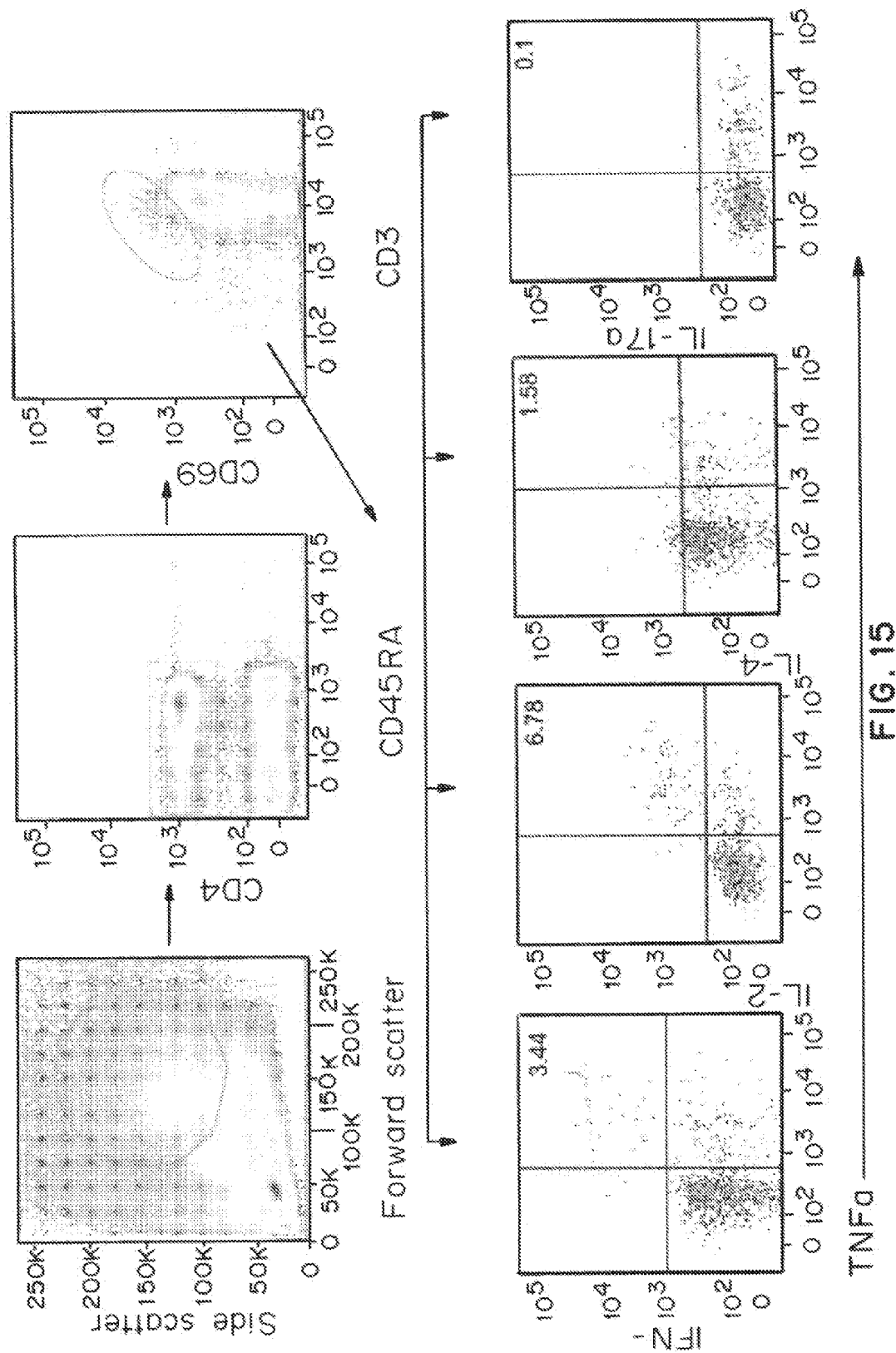

FIG. 15 is the gating strategy for enumerating cytokine specific memory CD4$^+$ T-cells among children. To exclude cell debris and clumps, cells were first gated based on their forward- and side-scatter properties followed by sequential gating on CD4$^+$ CD45RA$^{Low}$ T-cells and then to CD3$^+$CD69$^+$ cytokine positive cells before gating on to TNF-α vs. other cytokines. Low frequency responders were confirmed by excessive back gating. Preliminarily, whole assay was standardized and compared to multiplex bead array (CBA, BD Biosciences) for the detection of CD4$^+$ T-cell cytokine profiles.

Figure 16A:
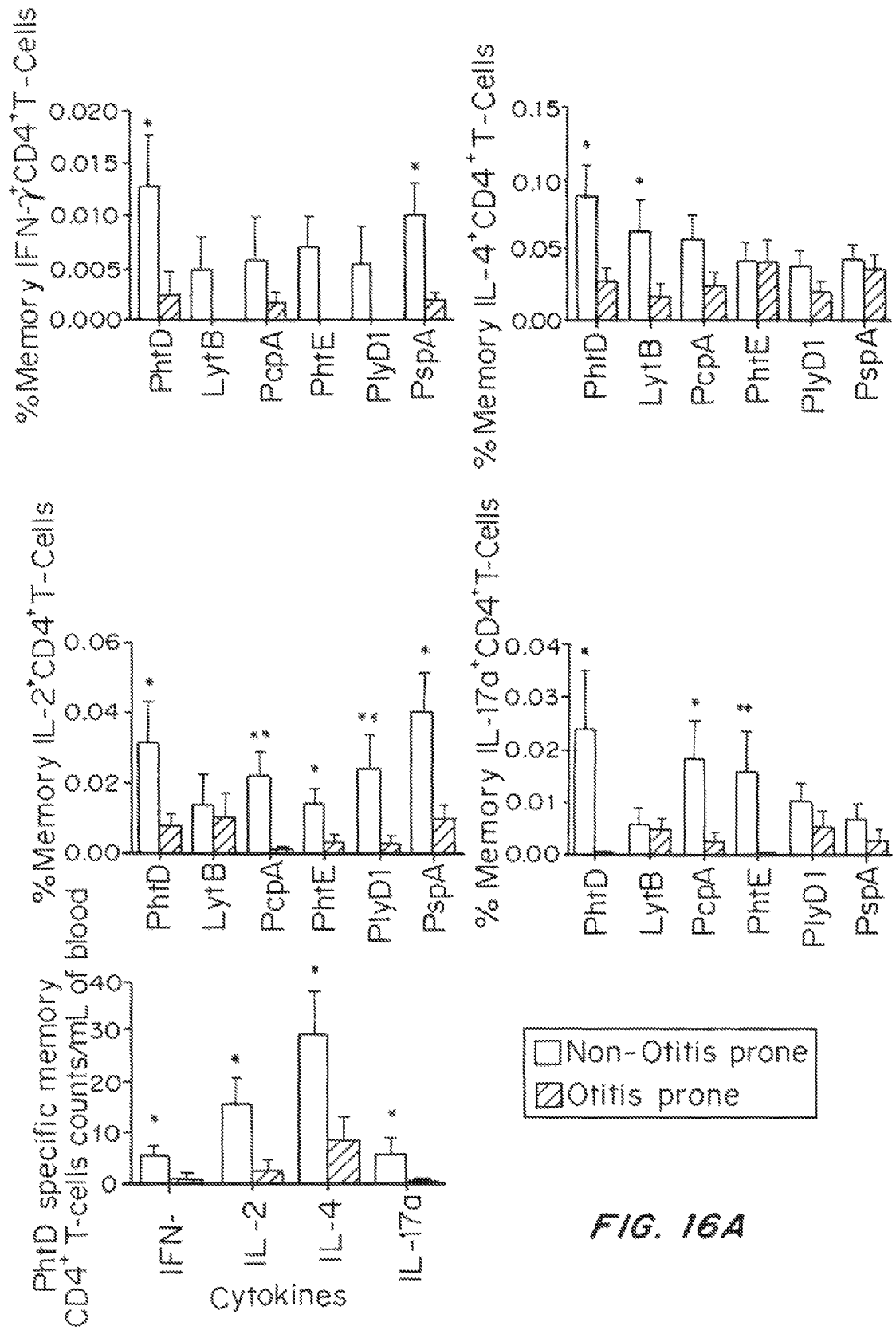
Figure 16B:
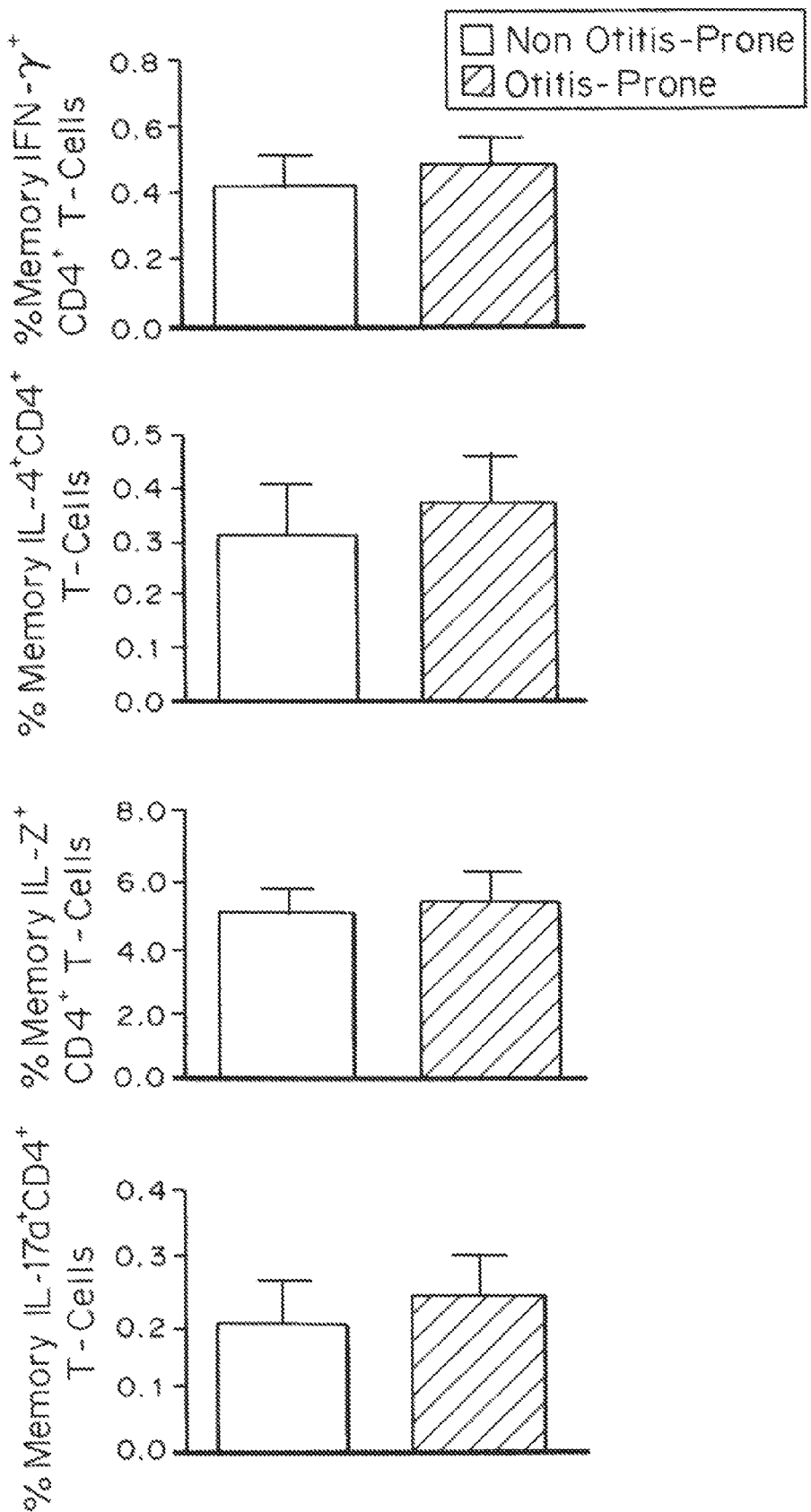

FIGS. 16A and 16B are graphs of memory T cells. [A] Percent frequencies of memory CD4$^+$ T-cell subsets producing various cytokines (IFN-γ, IL-4, IL-2 & IL-17a) against six pneumococcal antigens in the circulation of non-otitis prone and otitis prone children while un-stimulated control serve as a negative control. Bar graphs represent normalized mean percentage values of CD69$^+$ CD4$^+$ T-cells gated on CD45RA$^{Low}$, following antigen stimulations. Absolute blood counts were calculated for the cytokine producing cells in case of PhtD antigen. Error bars represent SEM; P values were calculated using Mann Whitney test. *P<0.05; **P<0.005. [B] PBMC samples from non otitis-prone and otitis-prone children were stimulated with SEB and cytokine production was observed in CD45RA$^{Low}$ CD4$^+$ T-cell population (p>0.5).

Figure 17A:
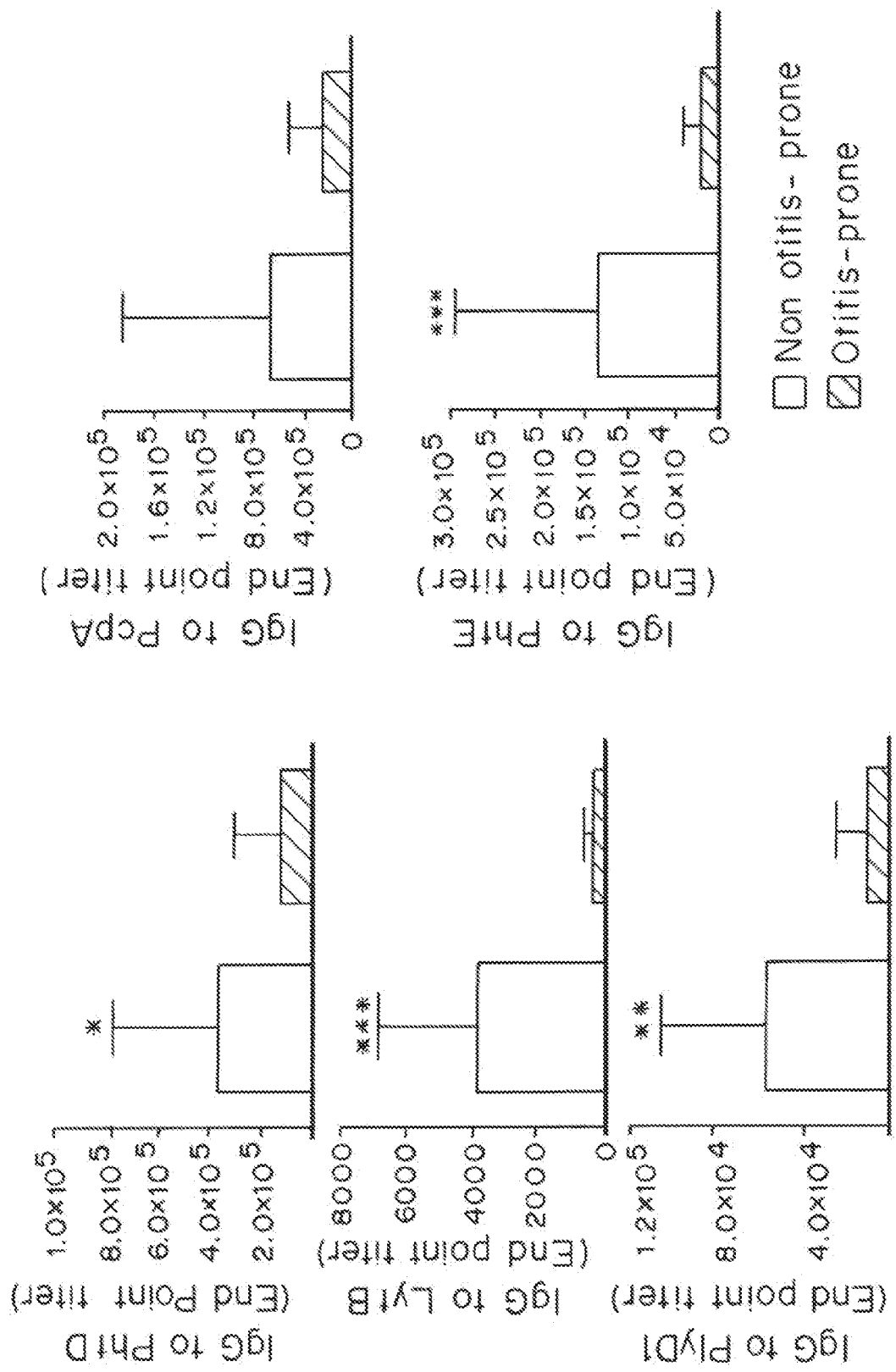
Figure 17B:
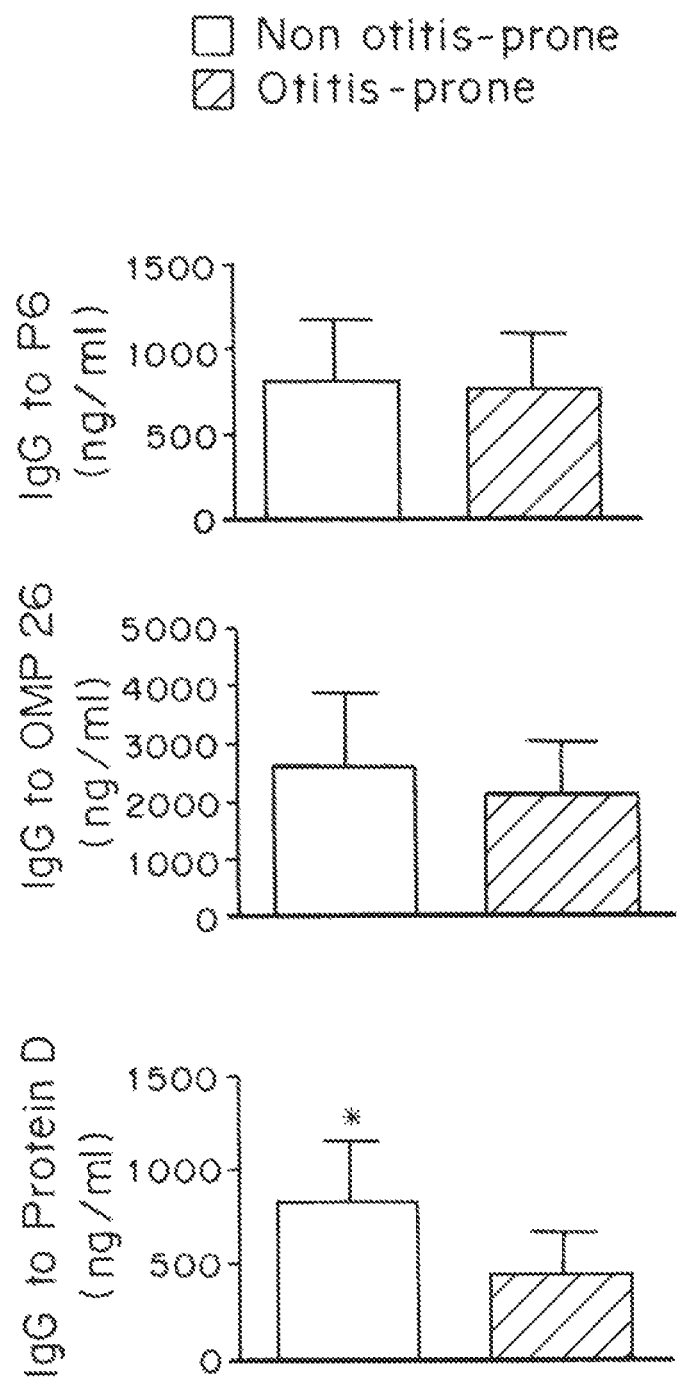

FIGS. 17A and 17B are graphs of IgG to different antigens. [A] Comparison of IgG responses to five pneumococcal protein antigens (PhtD, LytB, PcpA, PhtE and PlyD1) in the serum samples of two cohorts of non-otitis prone and otitis prone children. *P<0.05; P<0.005; *P<0.0005. Y-axis represents Geometric mean titers and error bars are upper 95% confidence intervals. [B] IgG responses to NTHi protein antigens (P6, OMP26 and Protein D) were also observed in the serum samples of two cohorts of non-otitis prone and otitis prone children. *P<0.05. Y-axis represents Geometric mean titers and error bars are upper 95% confidence intervals.

Figure 18A:
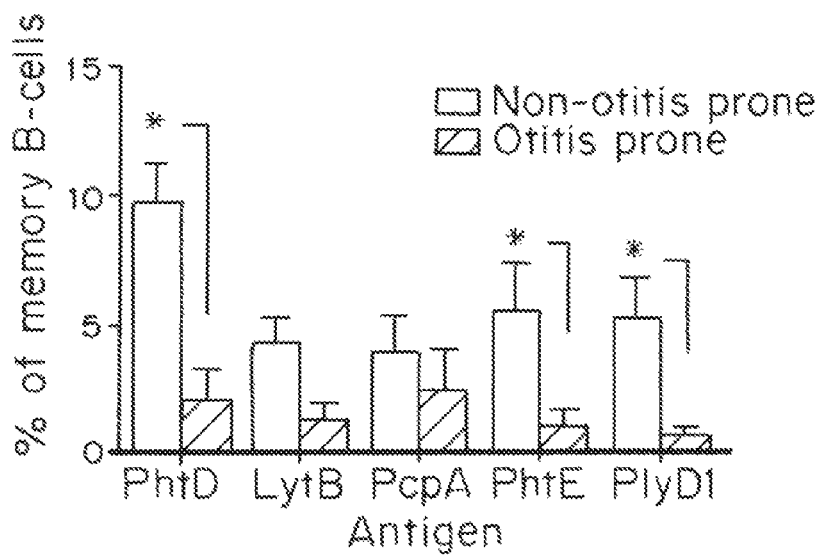
Figure 18B:
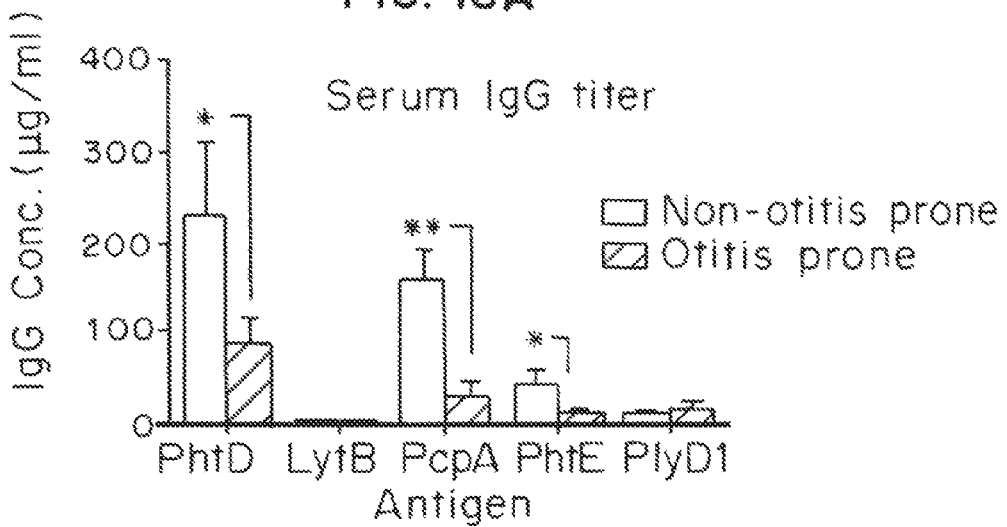
Figure 18C:
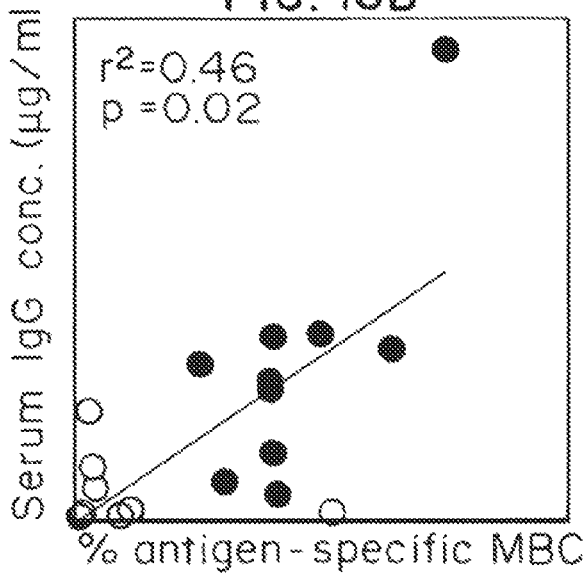

FIGS. 18A, 18B and 18C are graphs of memory B cells and IgG. FIG. 18A represents frequencies of antigen-specific memory B cells enumerated in the same cohorts (mean±SEM). Bar graphs shows mean±SEM of serum IgG titers to 5-pneumococcal protein antigens in non-otitis prone (n=12) and otitis prone children (n=10) (B). A correlation of PhtD specific serum antibody titers to the PhtD specific percentages of antigen specific memory B cells is shown in otitis prone (empty circles) and non-otitis prone children (filled circles) (C). P values were calculated using Mann Whitney test. *P<0.05 **<0.005.

DETAILED DESCRIPTION OF THE INVENTION

A. Compositions
1. Acute Otitis Media (AOM)

Otitis media is an inflammation of the middle ear, the space behind the ear drum. It is one of the two conditions that are commonly thought of as ear infections, the other being Otitis externa. Inflammation of the middle ear in otitis media is caused by a bacterial or viral infection. Ear infections are very common in childhood, and include acute and recurrent—or chronic-conditions; all of which involve inflammation of the ear drum (tympanic membrane), and are usually associated with a buildup of fluid in the space behind the ear drum (middle ear space). This inflammation and fluid buildup results in pain which causes caregivers or patients to readily seek medical attention for the condition.

Inflammation in the middle ear space, and the associated pain, are the essence of all otitis media infections. Once the middle ear space is filled with fluid, hearing will be dampened (conductive hearing impairment) until the condition improves. In many individuals, for the reasons discussed below, the condition is recurrent and will happen several times in a lifetime (chronic or recurrent otitis media).

There are essentially two types of otitis media recognized, each with a separate diagnosis and separate causes and general symptomatic profiles. Otitis Media with Effusion (OME) is primarily a non specific inflammatory response characterized by fluid behind the ear. Acute Otis Media (AOM) with effusion is an infectious disease characterized by rapid onset, pain, inflammation and the like of the middle ear. It appears that 40 to 50% of AOM in young children is caused by *Streptococcus pneumonia,* 20 to 30% by *Haemophilus* influenza and 10 to 15% by *Moraxella catarrhalis*. Recurrent AOM has been associated with excessive levels of *S. pneumonia* and *Haemophilus influenzae*. Additionally, low levels of antioxidants, including glutathione in particular, have also been shown to correlate with recurrent AOM (Cemek et al., International Journal of Pediatric Otorhinolaryngology, Volume 69, Issue 6, Pages 823-827).

Treatment of AOM has classically been accomplished with antibacterial medications. Classic antibacterial treatment based on the particular organism and its susceptibility to the antibiotic rather than the disease state has been the mainstay of most bacterial type infections. U.S. Pat. No. 6,987,093 discloses the use of Azithromycin to treat AOM. Of course a problem with antibiotic use is the eventual resistance of the particular antibiotic to the strains that cause AOM. It is clear that many high dosage antimicrobial treatments have a number of untoward side effects.

i. *Haemophilus* Influenza
a. Outer Membrane Protein (OMP) P6

The recombinant outer membrane protein of the invention may be derived from any NTHi bacterial outer membrane.

P6 is an outer membrane protein found on Nontypable *H. influenzae* (NTHi) which is the major cause of acute otitis media (AOM) (Casey et al. Pediatr Infect Dis J. 29:304-09, 2010). P6 was identified as highly specific marker for NTHi (Murphy et al. J Infect Dis. 152:1300-07, 1985). P6 is highly conserved among NTHi strains (Nelson et al. Infect Immun 59:2658-63, 1991). Since P6 is a surface protein, it is the target of human serum bactericidal antibodies (Bogdan et al. Infect Immun 63:4395-4401, 1995; Murphy et al. J Clin Invest 78:1020-27, 1986; De Maria et al. Infect Immun 64:5187-92, 1996).

P6 has previously been defined by its structure via NMR spectroscopy (Orban et al. Biochemistry 45:2122-28, 2006). The structure is hereby incorporated by reference. P6 is further defined in EP 281673 (State University of New York) which is hereby incorporated by reference.

The protein sequence for *Haemophilus influenzae* P6 Amino Acid sequence (SEQ ID NO:1):

```
  1   mnkfvksllv agsvaalaac sssnndaagn gaaqtfggys
      vadlqqrynt vyfgfdkydi 61   tgeyvqilda haaylnatpa akvlvegntd ergtpeynia
      lgqrradavk gylagkgvda 121   gklgtvsyge ekpavlghde aaysknrrav lay
```

One letter coded Amino Acid sequence (SEQ ID NO:1):

MNKFVKSLLVAGSVAALAACSSSNNDAAGNGAAQTFGGYSVADLQQR

YNTVYFGFDKYDITGEYVQILDAHAAYLNATPAAKVLVEGNTDERGT

PEYNIALGQRRADAVKGYLAGKGVDAGKLGTVSYGEEKPAVLGHDEA

AYSKNRRAVLAY b. Protein D

Information about protein D can be found in EP 594610 by Glaxo Smith Kline, which is herein incorporated by Reference in its entirety at least for information related to protein D and NTHi.

2. Vaccines

One composition disclosed herein is a vaccine. The vaccine can contain nucleic acids, amino acids or a combination thereof. A vaccine (or an immunogenic composition) comprises an immunogenic amount (preferably an effective or protective amount) of a composition, such as an outer membrane protein, (either isolated or purified, or present in an outer membrane vesicle, ghost or killed, live, or live-attenuated whole cell preparation) in a pharmaceutically acceptable excipient, and an optional adjuvant. In this context, immunogenic amount can be defined as a sufficient quantity of protein to elicit an antibody response in a host.

An immunogenic amount of one of the disclosed compositions can be formulated in a pharmaceutically acceptable excipient, and an optional adjuvant, to prevent or treat *Haemophilus influenzae* disease (preferably otitis media, sinusitis, conjunctivitis, or lower respiratory tract infection). Vaccines can be used to induce an immune response in a mammal susceptible to *Haemophilus influenzae* infection by administering to the mammal an effective amount of the vaccine (an effective amount being an amount capable of protecting a host to some degree against an NTHi infection). A vaccine can also prevent *Haemophilus influenzae* infection by administration to a mammal in an effective amount.

Vaccines are capable of eliciting a cross-protective immune response against a large variety of NTHi strains (particularly where one or more modified loops are integrated into an NTHi outer membrane protein).

A preferred vaccine comprises a recombinant NTHi outer membrane protein, preferably P6, as such vaccines can effectively protect a host against otitis media by immunization with a single molecule.

Vaccines can elicit a humoral response, cell-mediated immune response or a combination thereof. Ideally, the immune response provides protection upon subsequent challenge with NTHi. However, protective immunity is not required.

Additionally, the proteins of the present invention are preferably adjuvanted in the vaccine formulation of the invention. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes. Other known adjuvants include CpG containing oligonucleotides. The oligonucleotides are characterized in that the CpG dinucleotide is unmethylated. Such oligonucleotides are well known and are described in, for example WO96/02555.

Further preferred adjuvants are those which induce an immune response preferentially of the TH1 type. High levels of Th1-type cytokines tend to favor the induction of cell mediated immune responses to the given antigen, whilst high levels of Th2-type cytokines tend to favor the induction of humoral immune responses to the antigen. Suitable adjuvant systems include, for example monophosphoryl lipid A, preferably 3-de-O-acylated monophosphoryl lipid A (3D-MPL), or a combination of 3D-MPL together with an aluminium salt. CpG oligonucleotides also preferentially induce a TH1 response. An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21 3D-MPL & tocopherol in an oil in water emulsion is described in WO 95/17210 and is a preferred formulation.

3. Detection Label

The disclosed compositions can comprise a detection label, also referred to as detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique, a magnetic resonance technique, or an ultrasound technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferrimagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent agents include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethaneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011,686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraaza-cyclododecane-N—,N',N",N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbiurn(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

The detectable agent can be coupled to the composition in such a way so as not to interfere with the ability of the vaccine to generate an immune response. The detectable agent can be directly or indirectly bound or conjugated to the disclosed compositions.

4. Therapeutic Agents

As used herein, the term "therapeutic agent" means a molecule which can have one or more biological activities in a normal or pathologic tissue. A variety of therapeutic agents can be used. The therapeutic agent can comprise a compound or composition for treating viral, bacterial or fungal diseases. The therapeutic agent can comprise a compound or composition to A therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; and pro-apoptotic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); a cytotoxic polypeptide including a toxin or caspase, for example, diphtheria toxin A chain, *Pseudomonas* exotoxin A, cholera toxin, a ligand fusion toxin such as DAB389EGF or ricin; or one of those described further herein or known in the art (see below). It is understood that these and other polypeptides with biological activity can be a "therapeutic polypeptide."

The compositions disclosed herein can also be used at a site of inflammation or injury. Agents useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. For example, disclosed are agents comprising an antimicrobial peptide, where the composition is selectively internalized and exhibits a high toxicity to the targeted area. Useful antimicrobial peptides can have low mammalian cell toxicity when not incorporated into the composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including Gram-positive or Gram-negative bacteria, or fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:151-155 (1990); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into the composition disclosed herein can have low mammalian cell toxicity when linked to the composition. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, disclosed are compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art.

An antimicrobial peptide that induces significant mitochondrial swelling at, for example, 50 μM, 40 μM, 30 μM, 20 μM, 10 μM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

Anti-fungal agents that can be administered with the compounds of the invention include, but are not limited to, polyene antifungals (e.g., amphotericin and nystatin), azole antifungals (e.g., ketoconazole, miconazole, fluconazole, itraconazole, posaconazole, ravuconazole, voriconazole, clotrimazole, econazole, oxiconazole, sulconazole, terconazole, butoconazole, isavuconazole, and tioconazole), amorolfine, butenafine, naftifine, terbinafine, flucytosine, nikkomycin Z, echinocandins (e.g., caspofungin, micafungin (FK463), anidulafungin (LY303366)), griseofulvin, ciclopiroxolamine, tolnaftate, intrathecal, 5-fluorocytosine, MK0991 (Merck), haloprogrin, and undecylenate.

Anti-bacterial agents that can be administered with the compounds of the invention include, but are not limited to, sulfa drugs (e.g., sulfanilamide), folic acid analogs (e.g., trimethoprim), beta-lactams (e.g., penacillin, cephalosporins), aminoglycosides (e.g., stretomycin, kanamycin, neomycin, gentamycin), tetracyclines (e.g., chlorotetracycline, oxytetracycline, and doxycycline), macrolides (e.g., erythromycin, azithromycin, and clarithromycin), lincosamides (e.g., clindamycin), streptogramins (e.g., quinupristin and dalfopristin), fluoroquinolones (e.g., ciprofloxacin, levofloxacin, and moxifloxacin), polypeptides (e.g., polymixins), rifampin, mupirocin, cycloserine, aminocyclitol (e.g., spectinomycin), glycopeptides (e.g., vancomycin), oxazolidinones (e.g., linezolid), ribosomes, chloramphenicol, fusidic acid, and metronidazole.

Anti-viral agents that can be administered with the compounds of the invention include, but are not limited to, Emtricitabine (FTC); Lamivudine (3TC); Carbovir; Acyclovir; Interferon; Famciclovir; Penciclovir; Zidovudine (AZT); Didanosine (ddI); Zalcitabine (ddC); Stavudine (d4T); Tenofovir DF (Viread); Abacavir (ABC); L-(−)-FMAU; L-DDA phosphate prodrugs; .beta.-D-dioxolane nucleosides such as .beta.-D-dioxolanyl-guanine (DG), .beta.-D-dioxolanyl-2,6-diaminopurine (DAPD), and .beta.-D-dioxolanyl-6-chloro-purine (ACP); non-nucleoside RT inhibitors such as Nevirapine (Viramune), MKC-442, Efavirenz (Sustiva), Delavirdine (Rescriptor); protease inhibitors such as Amprenavir, Atazanavir, Fosamprenavir, Indinavir, Kaletra, Nelfinavir, Ritonavir, Saquinavir, AZT, DMP-450; combination treatments such as Epzicom (ABC+3TC), Trizivir (ABC+3TC+AZT), Truvada (FTC+Viread); Omega IFN (BioMedicines Inc.); BILN-2061 (Boehringer Ingelheim); Summetrel (Endo Pharmaceuticals Holdings Inc.); Roferon A (F. Hoffman-La Roche); Pegasys (F. Hoffman-La Roche); Pegasys/Ribaravin (F. Hoffman-La Roche); CellCept (F. Hoffman-La Roche); Wellferon (GlaxoSmithKline); Albuferon-alpha (Human Genome Sciences Inc.); Levovirin (ICN Pharmaceuticals); IDN-6556 (Idun Pharmaceuticals); IP-501 (Indevus Pharmaceuticals); Actimmune (InterMune Inc.); Infergen A (InterMune Inc.); ISIS 14803 (ISIS Pharamceuticals Inc.); JTK-003 (Japan Tobacco Inc.); Pegasys/Ceplene (Maxim Pharmaceuticals); Ceplene (Maxim Pharmaceuticals); Civacir (Nabi Biopharmaceuticals Inc.); Intron A/Zadaxin (RegeneRx); Levovirin (Ribapharm Inc.); Viramidine (Ribapharm Inc.); Heptazyme (Ribozyme Pharmaceuticals); Intron A (Schering-Plough); PEG-Intron (Schering-Plough); Rebetron (Schering Plough); Ribavirin (Schering-Plough); PEG-Intron/Ribavirin (Schering-Plough); Zadazim (SciClone); Rebif (Serono); IFN-.beta./EMZ701 (Transition Therapeutics); T67 (Tularik Inc.); VX-497 (Vertex Pharmaceuticals Inc.); VX-950/LY-570310 (Vertex Pharmaceuticals Inc.); Omniferon (Viragen Inc.); XTL-002 (XTL Biopharmaceuticals); SCH 503034 (Schering-Plough); isatoribine and its prodrugs ANA971 and ANA975 (Anadys); R1479 (Roche Biosciences); Valopicitabine (Idenix); NIM811 (Novartis); Actilon (Coley Pharmaceuticals); Pradefovir (Metabasis. Therapeutics); zanamivir; adefovir, adefovir dipivoxil, oseltamivir; vidarabine; gancyclovir; valganciclovir; amantadine; rimantadine; relenza; tamiflu; amantadine; entecavir; and pleconaril.

Anti-parasitic agents that can be administered with the compounds of the invention include, but are not limited to, avermectins, milbemycins, lufenuron, imidacloprid, organophosphates, pyrethroids, sufanamides, iodquinol, diloxanide furoate, metronidazole, paromycin, azithromycin, quinacrine, furazolidone, tinidazole, ornidazole, bovine, colostrum, bovine dialyzable leukocyte extract, chloroquine, chloroquine phosphate, diclazuril, eflornithine, paromomycin, pentamidine, pyrimethamine, spiramycin, trimethoprim-sulfamethoxazole, albendazole, quinine, quinidine, tetracycline, pyrimethamine-sulfadoxine, mefloquine, doxycycline, proguanil, clindamycin, suramin, melarsoprol, diminazene, nifurtimox, spiroarsoranes, ketoconazole, terbinafine, lovastatin, sodium stibobgluconate, N-methylglucamine antimonate, amphotericin B, allopurinol, itraconazole, sulfadiazine, dapsone, trimetrexate, clarithromycin, roxithromycin, atovaquone, aprinocid, timidazole, mepacrine hydrochloride, emetine, polyaminopropyl biguanide, paromomycin, benzimidazole, praziquantel, or albendazole.

5. Peptides and Peptide Variants

In some forms, the compositions can be or include a peptide, peptidomimetic, and/or amino acid segment. Unless the context indicates otherwise, reference herein to "peptide" is intended to refer also to amino acid segments, which can form a part of, or constitute an entire, peptide. The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides and amino acid segments can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The disclosed amino acid segments can have, for example, a relatively short length of less than six, seven, eight, nine, ten, 12, 15, 20, 25, 30, 35 or 40 residues. The disclosed amino acid segments also can be useful in the context of a significantly longer sequence. Thus, the amino acid segments can have, for example, a length of up to 50, 100, 150, 200, 250, 300, 400, 500, 1000 or 2000 residues. In particular embodiments, an amino acid segment can have a length of at least 10, 20, 30, 40, 50, 60, 70, 80, 90, 100 or 200 residues. In further embodiments, an amino acid segment can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins, protein sequences, peptides, peptides sequences, and amino acid sequences, it is understood that the nucleic acids that can encode those sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. The disclosed peptides and proteins can be coupled to each other via peptide bonds to form fusion peptides and proteins.

The disclosed peptides and amino acid segments can be modified. As used herein, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does no include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence of the amino acid segment and methylated forms of the amino acid sequence of the amino acid segment include amino acid substitutions.

Protein variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

Substitutional variants are those in which at least one residue has been removed and a different residue inserted in its place. Examples of such substitutions, referred to as conservative substitutions, can generally be made in accordance with the following Table 6.

TABLE 6

Amino Acid Substitutions
Original Residue Exemplary Conservative
Substitutions, others are known in the art.

| Original Residue | Exemplary Conservative Substitutions |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |

TABLE 6-continued

Amino Acid Substitutions
Original Residue Exemplary Conservative
Substitutions, others are known in the art.

| Original Residue | Exemplary Conservative Substitutions |
|---|---|
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity can be made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. These can be referred to a less conservative variants.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or .alpha.-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods [e.g., as described in Hruby, et al. (1990) Biochem J. 268:249-262].

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243-252]. These techniques include, but are not limited to, replacing the peptide backbone with a backbone composed of phosphonates, amidates, carbamates, sulfonamides, secondary amines, and N-methylamino acids.

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH═CH— (cis and trans), —COCH$_2$—, —CH(OH)CH$_2$—, and —CHH$_2$SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$); Spatola et al. Life Sci 38:1243-1249 (1986) (—CHH$_2$—S); Hann J. Chem. Soc Perkin Trans. I 307-314 (1982) (—CH—CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as β-alanine, γ-aminobutyric acid, and the like.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, can be accomplished, for example, by deleting one of the basic residues or substituting one by glutaminyl or histidyl residues.

Certain post-translational derivatizations can be the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed amino acids sequences, amino acid segments, peptides, proteins, etc. herein is through defining the variants and derivatives in terms of homology/identity to specific known sequences. For example, specifically disclosed are variants of these and other amino acids sequences, amino acid segments, peptides, proteins, etc. herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Nati. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative variants and homology can be combined together in any combination, such as embodiments that have at least 70% homology to a particular sequence wherein the variants are conservative variants.

As this specification discusses various amino acids sequences, amino acid segment sequences, peptide sequences, protein sequences, etc., it is understood that nucleic acids that can encode those sequences are also disclosed. This would include all degenerate sequences related to a specific amino acid sequence, i.e. all nucleic acids having a sequence that encodes one particular amino acid sequence as well as all nucleic acids, including degenerate nucleic acids, encoding the disclosed variants and derivatives of the amino acid sequences. Thus, while each particular nucleic acid sequence may not be written out herein, it is understood that each and every sequence is in fact disclosed and described herein through the disclosed amino acid sequences.

Also disclosed are bifunctional peptides, which contain the homing peptide fused to a second peptide having a separate function. Such bifunctional peptides have at least two functions conferred by different portions of the full-length molecule and can, for example, display anti-angiogenic activity or pro-apoptotic activity in addition to the ability to home to a target.

Also disclosed are isolated multivalent peptides that include at least two subsequences each independently containing a peptide or amino acid segment. The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. This is in addition to the multiple homing molecules and, for example, multiple membrane disrupting molecules that can comprise the disclosed compositions. In a further embodiment, the multivalent peptide can contain identical subsequences, such as repeats of a specified amino acid sequence. In a further embodiment, the multivalent peptide contains contiguous identical or non-identical subsequences, which are not separated by any intervening amino acids.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an $N^\alpha$—$C^\alpha$ cyclized amino acid; an $N^\alpha$.-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

6. Pharmaceutical Compositions and Carriers

The disclosed compositions can be administered in vivo either alone or in a pharmaceutically acceptable carrier. By "pharmaceutically acceptable" is meant a material that is not biologically or otherwise undesirable, i.e., the material can be administered to a subject, along with the composition disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

i. Pharmaceutically Acceptable Carriers

The compositions disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

7. Delivery Systems

Expression vectors can comprise the DNA or RNA molecule of the invention, wherein said expression vector is capable of expressing a recombinant outer membrane protein of the invention when present in a compatible host cell, and a host cell comprising this expression vector.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (2nd Ed., Cold Spring Harbor Laboratory Press, Cold Spring Harbor, N.Y. (1989)).

Delivery can be applied, in general, via local or systemic routes of administration. Local administration includes virus injection directly into the region or organ of interest, versus intravenous (IV) or intraperitoneal (IP) injections (systemic) aiming at viral delivery to multiple sites and organs via the blood circulation. Previous research on the effects of local administration demonstrated gene expression limited to the site/organ of the injection, which did not extend to the rest of the body (Daly et al., 1999a; Kordower et al., 1999). Furthermore, previous studies have demonstrated successful global gene transfer to multiple tissues and organs in rodents and primates following viral IV and IP injections (Daly et al., 1999b; Tarntal et al., 2001; McCormack et al., 2001; Lipschutz et al., 2001). Disclosed herein IP injection of FIV(lacZ) in mice of adult (3 months old) as well as of perinatal age (P4)

resulted in global transfer and expression of the reporter gene lacZ in brain, liver, spleen and kidney. Also disclosed, the levels of expression achieved via IP injections were superior to those acquired following local administration directly into the liver.

As stated above, there are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as P6 construct into the cell without degradation and include a promoter yielding expression of P6 encoding sequences in the cells into which it is delivered. In some embodiments the vectors for the P6 constructs are derived from either a virus, retrovirus, or lentivirus. Viral vectors can be, for example, Adenovirus, Adeno-associated virus, Herpes virus, Vaccinia virus, Polio virus, AIDS virus, neuronal trophic virus, Sindbis and other RNA viruses, including these viruses with the HIV backbone, and lentiviruses. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene, such as, the disclosed P6 constructs or marker gene, than other viral vectors, and for this reason are commonly used vectors. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector, which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virions are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

d. Lentiviral Vectors

The vectors can be lentiviral vectors, including but not limited to, SIV vectors, HIV vectors or a hybrid construct of these vectors, including viruses with the HIV backbone.

These vectors also include first, second and third generation lentiviruses. Third generation lentiviruses have lentiviral packaging genes split into at least 3 independent plasmids or constructs. Also vectors can be any viral family that shares the properties of these viruses which make them suitable for use as vectors. Lentiviral vectors are a special type of retroviral vector which are typically characterized by having a long incubation period for infection. Furthermore, lentiviral vectors can infect non-dividing cells. Lentiviral vectors are based on the nucleic acid backbone of a virus from the lentiviral family of viruses. Typically, a lentiviral vector contains the 5' and 3' LTR regions of a lentivirus, such as SIV and HIV. Lentiviral vectors also typically contain the Rev Responsive Element (RRE) of a lentivirus, such as SIV and HIV.

(A) Feline Immunodeficiency Viral Vectors

One type of vector that the disclosed constructs can be delivered in is the VSV-G pseudotyped Feline Immunodeficiency Virus system developed by Poeschla et al. (1998). This lentivirus has been shown to efficiently infect dividing, growth arrested as well as post-mitotic cells. Furthermore, due to its lentiviral properties, it allows for incorporation of the transgene into the host's genome, leading to stable gene expression. This is a 3-vector system, whereby each confers distinct instructions: the FIV vector carries the transgene of interest and lentiviral apparatus with mutated packaging and envelope genes. A vesicular stomatitis virus G-glycoprotein vector (VSV-G; Burns et al., 1993) contributes to the formation of the viral envelope in trans. The third vector confers packaging instructions in trans (Poeschla et al., 1998). FIV production is accomplished in vitro following co-transfection of the aforementioned vectors into 293-T cells. The FIV-rich supernatant is then collected, filtered and can be used directly or following concentration by centrifugation. Titers routinely range between 104-107 bfu/ml.

e. Packaging Vectors

As discussed above, retroviral vectors are based on retroviruses which contain a number of different sequence elements that control things as diverse as integration of the virus, replication of the integrated virus, replication of un-integrated virus, cellular invasion, and packaging of the virus into infectious particles. While the vectors in theory could contain all of their necessary elements, as well as an exogenous gene element (if the exogenous gene element is small enough) typically many of the necessary elements are removed. Since all of the packaging and replication components have been removed from the typical retroviral, including lentiviral, vectors which will be used within a subject, the vectors need to be packaged into the initial infectious particle through the use of packaging vectors and packaging cell lines. Typically retroviral vectors have been engineered so that the myriad functions of the retrovirus are separated onto at least two vectors, a packaging vector and a delivery vector. This type of system then requires the presence of all of the vectors providing all of the elements in the same cell before an infectious particle can be produced. The packaging vector typically carries the structural and replication genes derived from the retrovirus, and the delivery vector is the vector that carries the exogenous gene element that is preferably expressed in the target cell. These types of systems can split the packaging functions of the packaging vector into multiple vectors, e.g., third-generation lentivirus systems. Dull, T. et al., "A Third-generation lentivirus vector with a conditional packaging system" J. Virol 72(11):8463-71 (1998)

Retroviruses typically contain an envelope protein (env). The Env protein is in essence the protein which surrounds the nucleic acid cargo. Furthermore cellular infection specificity is based on the particular Env protein associated with a typical retrovirus. In typical packaging vector/delivery vector systems, the Env protein is expressed from a separate vector than for example the protease (pro) or integrase (in) proteins.

(A) Packaging Cell Lines

The vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals. One type of packaging cell line is a 293 cell line.

f. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson. Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

ii. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed constructs or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)). Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

8. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

i. Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, alpha-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

a. Constitutive Promoters

In certain embodiments the promoters are constitutive promoters. This can be any promoter that causes transcription regulation in the absence of the addition of other factors. Examples of this type of promoter are the CMV promoter and the beta actin promoter, as well as others discussed herein. In certain embodiments the promoter can consist of fusions of one or more different types of promoters. For example, the regulatory regions of the CMV promoter and the beta actin promoter are well known and understood, examples, of which are disclosed herein. Parts of these promoters can be fused together to, for example, produce a CMV-beta actin fusion promoter. It is understood that this type of promoter has a CMV component and a beta actin component. These components can function independently as promoters, and thus, are themselves considered beta actin promoters and CMV promoters. A promoter can be any portion of a known promoter that causes promoter activity. It is well understood that many promoters, including the CMV and Beta Actin promoters have functional domains which are understood and that these can be used as a beta actin promoter or CMV promoter. Furthermore, these domains can be determined There are many CMV promoter variations that exist, as well as beta actin promoters, and fusion promoters. These promoters can be compared, and for example, functional regions delineated, as described herein. Furthermore, each of these sequences can function independently or together in any combination to provide a promoter region for the disclosed nucleic acids.

b. Non-Constitutive Promoters

The promoters can also be non-constitutive promoters, such as cell specific promoters. These are promoters that are turned on at specific time in development or stage or a particular type of cell, such as a cardiac cell, or neural cell, or a bone cell. Some examples of cell specific promoters are, the neural enolase specific promoter, (NSE) the COLL1A1 procollagen promoter, and the CD11b promoter (PBMC-microglia/macrophage/monocyte specific promoter.

It is understood that the recombinant systems can be expressed in a tissue-specific manner. It is understood that tissue specific expression can occur due to the presence of a tissue-specific promoter. Typically, proteins under control of a tissue-specific promoter are transcribed when the promoter becomes active by virtue of being present in the tissue for which it is specific. Therefore, all cells can encode for a particular gene without global expression. As such, labeled proteins can be shown to be present in certain tissues without expression in other nearby tissues that may complicate results or expression of proteins in tissues where expression may be detrimental to the host. Disclosed are methods wherein the cre recombinase is under the control of the EIIA promoter, a promoter specific for breast tissue, such as the WAP promoter, a promoter specific for ovarian tissue, such as the ACTB promoter, or a promoter specific for bone tissue, such as osteocalcin. Any tissues specific promoter can be used. Promoters specific for prostate, testis, and neural are also disclosed. Examples of some tissue-specific promoters include but are not limited to MUC1, EIIA, ACTB, WAP, bHLH-EC2, HOXA-1, Alpha-fetoprotein (AFP), opsin, CR1/2, Fc-.quadrature.-Receptor 1 (Fc-.quadrature.-R1), MMTVD-LTR, the human insulin promoter, Pdha-2, rat neuron-specific enolase. For example, use of the AFP promoter creates specificity for the liver. Another example, HOXA-1 is a neuronal tissue specific promoter, and as such, proteins expressed under the control of HOXA-1 are only expressed in neuronal tissue. (All of which are herein incorporated by reference at least for the sequence of the promoters and related sequences.)

Other cell specific promoters can be found in (Sutcliffe, J. G. (1988), Ann. Rev. Neuroscience 11, 157-198). For example, when transfecting nerve cells, there are a variety of nerve specific promoters, such as the neuron specific enolase promoter. Other examples of neuron specific promoters would be the Tau promoter, Synapsin I (Hoesche, C., Sauerwald, A., et al., (1993) J. Biol. Chem. 268, 26494-26502. and II (Chin, L.-S et al., (1994), J. Biol. Chem. 269, 18507-18513) promoters, the amino acid decarboxylase (AADC) (Albert, V., et al., (1992), Proc. Natl. Acad. Sci. 89, 12053-12057) and FE65 (Faraonio, R., et al., (1994), Nucl. Acids Res. 22, 4876-4883) promoters. Other nerve specific promoters include, the promoter for the WT1 gene (Fraizer, G, et al., (1994), J. Biol. Chem. 269, 8892-8900), nuerofilament light chain promoter (Yazdanbakhsh, K., et al., (1993) Nucl. Acids Res. 21, 455-461), and the glial fibrillary acidic protein, (Kaneko, R. & Sueoka, N. (1993) Proc. Natl. Acad. Sci. 90, 4698-4702). (All of which are herein incorporated by reference at least for the sequence of the promoters and related sequences.)

Expression of the transgene can be targeted selectively to neurons by cloning a neuron specific promoter, such as the NSE promoter as disclosed herein (Liu H. et al., Journal of Neuroscience. 23(18):7143-54, 2003); tyrosine hydroxylase promoter (Kessler M A. et al., Brain Research. Molecular Brain Research. 112(1-2):8-23, 2003); myelin basic protein promoter (Kessler M A. et al Biochemical & Biophysical Research Communications. 288(4):809-18, 2001); glial fibrillary acidic protein promoter (Nolte C. et al., GLIA. 33(1):72-86, 2001); neurofilaments gene (heavy, medium, light) promoters (Yaworsky P J. et al., Journal of Biological Chemistry. 272(40):25112-20, 1997) (All of which are herein incorporated by reference at least for the sequence of the promoters and related sequences.) The NSE promoter is disclosed in Peel A L. et al., Gene Therapy. 4(1):16-24, 1997) (SEQ ID NO:69) (pTR-NT3myc; Powell Gene Therapy Center, University of Florida, Gainesville Fla.).

ii. Markers

The viral vectors can include nucleic acid sequence encoding a marker product. This marker product is used to determine if the gene has been delivered to the cell and once delivered is being expressed. Preferred marker genes are the E. Coli lacZ gene, which encodes .beta.-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mal. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

iii. Post Transcriptional Regulatory Elements

The disclosed vectors can also contain post-transcriptional regulatory elements.

Post-transcriptional regulatory elements can enhance mRNA stability or enhance translation of the transcribed mRNA. An exemplary post-transcriptional regulatory sequence is the WPRE sequence isolated from the woodchuck hepatitis virus. (Zufferey R, et al., "Woodchuck hepatitis virus post-transcriptional regulatory element enhances expression of transgenes delivered by retroviral vectors," J Virol; 73:2886-92 (1999)). Post-transcriptional regulatory elements can be positioned both 3' and 5' to the exogenous gene, but it is preferred that they are positioned 3' to the exogenous gene.

iv. Transduction Efficiency Elements

Transduction efficiency elements are sequences that enhance the packaging and transduction of the vector. These elements typically contain polypurine sequences. An example of a transduction efficiency element is the ppt-cts sequence that contains the central polypurine tract (ppt) and central terminal site (cts) from the FIV. These sequences are in the disclosed FIV sequences herein. Each retrovirus and lentivirus can have there own ppt-cts.

v. 3' Untranslated Regions

Expression vectors used in eukaryotic host cells (yeast, fungi, insect, plant, animal, human or nucleated cells) can also contain sequences necessary for the termination of transcription which can affect mRNA expression. These 3' untranslated regions are transcribed as polyadenylated segments in the untranslated portion of the mRNA encoding the exogenous gene. The 3' untranslated regions also include transcription termination sites. The transcription unit also can contain a polyadenylation region. One benefit of this region is that it increases the likelihood that the transcribed unit will be processed and transported like mRNA. The identification and use of polyadenylation signals in expression constructs is well established. Homologous polyadenylation signals can be used in the transgene constructs. In an embodiment of the transcription unit, the polyadenylation region is derived from the SV40 early polyadenylation signal and consists of about 400 bases. Transcribed units can contain other standard sequences alone or in combination with the above sequences improve expression from, or stability of, the construct.

9. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

10. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

11. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include the P6 vaccine.

Methods

A. Methods of Treating with Combination Therapies

The disclosed methods can comprise treating an individual with one of the disclosed compositions, such as a P6 vaccine, in combination with a therapeutic agent. The therapeutic agent can be a therapeutic polypeptide, peptide (including one or more peptides of the invention), a nucleic acid encoding a therapeutic polypeptide, an anti-inflammatory agent, a biological and/or small molecule targeting agent, an immunomodulatory agent, or a combination thereof, for example. The therapeutic agent may be administered simultaneously with the vaccine, or administered at a different time than the vaccine.

Combination therapies can provide one or more therapeutic benefits. The therapies can have a synergistic effect wherein the presence of multiple therapies is more than the sum of each individual therapy. There can be one therapeutic effect that is enhanced by the presence of a second therapy.

The treatment of subjects can include the disclosed compositions alone or in combination with a therapeutic agent. The therapeutic agent can be any of the therapeutic agents disclosed herein. The therapeutic agent can be but is not limited to an anti-viral, anti-bacterial or anti-inflammatory agent.

The disclosed compositions can be administered as multivalent subunit vaccines in combination with antigens from other proteins of *H. influenzae* to achieve an enhanced bactericidal activity. They can also be administered in combination with polysaccharide antigens, for example the PRP capsular polysaccharide (preferably conjugated to a protein such as tetanus toxoid) of *H. influenzae* b. For combined administration with epitopes of other proteins, the protein of the invention is either administered separately, as a mixture (for instance within an outer membrane vesicle preparation) or as a conjugate or genetic fusion polypeptide. The conjugate is formed by standard techniques for coupling proteinaceous materials. The proteins of the invention can be used in conjunction with antigens of other organisms (e.g. encapsulated or nonencapsulated, bacteria, viruses, fungi and parasites). For example, the proteins of the invention are useful in conjunction with antigens of other microorganisms implicated in otitis media or other diseases. These include *Streptococcus pneumoniae*, *Streptococcus* pyrogenes group A, *Staphylococcus aureus*, respiratory syncytial virus and *Moraxella catarrhalis*

The compositions can be used in combination vaccines which provide protection against a range of different pathogens. Many pediatric vaccines are now given as a combination vaccine so as to reduce the number of injections a child has to receive. Thus for pediatric vaccines, other antigens from other pathogens may be formulated with the compositions disclosed herein. For example the disclosed compositions can be formulated with (or administered separately but at the same time) the well known 'trivalent' combination vaccine comprising Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2] for example, the marketed vaccine INFANRIX-DTPa™ (SmithKlineBeecham Biologicals) which contains DT, TT, PT, FHA and PRN antigens, or with a whole cell pertussis component for example as marketed by SmithKlineBeecham Biologicals s.a., as Tritanrix™. The combined vaccine may also comprise other antigens, such as Hepatitis B surface antigen (HBsAg), Polio virus antigens (for instance inactivated trivalent polio virus—IPV), *Moraxella catarrhalis* outer membrane proteins, non-typeable *Haemophilus influenzae* proteins, *N. meningitidis* B outer membrane proteins. Examples of other non-typeable *Haemophilus influenzae* antigens which can be included in a combination vaccine (especially for the prevention of otitis media) include: Fimbrin protein [(U.S. Pat. No. 5,766,608-Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; TbpA and/or TbpB; Hia; Hsf; Hin47; Hif; Hmw1; Hmw2; Hmw3; Hmw4; Hap; D15 (WO 94/12641); P2; and P5 (WO 94/26304).

B. Methods of Administering

The compositions can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compositions can be administered intravenously, intraperitoneally, intramuscularly, subcutaneously, intracavity, or transdermally.

The compositions provided herein may be administered in a physiologically acceptable carrier to a host. Preferred methods of administration include systemic or direct administration to a cell. The compositions can be administered to a cell or subject, as is generally known in the art for gene therapy applications. In gene therapy applications, the compositions are introduced into cells in order to transfect an organelle. "Gene therapy" includes both conventional gene therapy where a lasting effect is achieved by a single treatment, and the administration of gene therapeutic agents, which involves the one time or repeated administration of a therapeutically effective DNA or RNA.

The modified complex compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

1. Parental Administration

The compositions of the present disclosure can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

2. Dosages

Dosages and desired concentrations of the pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

The amount or dose of the material administered should be sufficient to affect a therapeutic or prophylactic response in a subject over a reasonable time frame. For example, the dose of the material should be sufficient to treat a bacterial infection. The dose should be sufficient to stimulate the immune response and/or treat or prevent AOM in children prone to otitis media.

Many assays for determining an administered dose are known in the art. For purposes of the present methods, an assay which comprises comparing the bactericidal antibodies in response to several different doses of a substance (i.e. P6 vaccine) to a set of mammals can be performed. The dose also can be determined by the existence, nature and extent of any adverse side effects that might accompany the administration. A variety of factors, such as age, body weight, general health, diet, sex, material to be administered, route of administration, and the severity of the condition being treated can be considered when determining dosage.

3. Administration of Multiple Compositions

Simultaneous administration of two compositions, such as a P6 vaccine and a therapeutic, means that the compositions are administered at the same time. To be administered at the same time means that both compositions are administered together. Administering the compositions together involves formulating them in a compatible carrier. Simultaneous administration can also refer to administering one composition in one formulation and then immediately administering the other composition. Simultaneous administration is the administration of two or more compositions within 30 minutes of each other.

The vaccine and the therapeutic can also be administered consecutively. Consecutive administration refers to separate, individual formulations for each composition. The compositions can be administered in any order: the conjugate first or the second therapeutic first. The term consecutive administration refers to administration of one composition and then at least 30 minutes later administering the other composition. The consecutive administration can be at least 30 minutes, 45 minutes, 1 hour, 2 hours, 3 hours, 4 hours, 5 hours, 10 hours, 12 hours, 18 hours, 1 day, 2 days, 3 days, 4 days, 5 days, 6 days, 7 days, 10 days, 14 days or 30 days from the administration of the first composition.

DEFINITIONS

Unless defined otherwise, all technical and scientific terms used herein have the same meanings as commonly understood by one of skill in the art to which the disclosed invention belongs. Publications cited herein and the materials for which they are cited are specifically incorporated by reference.

1. A, an the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. AOM

AOM was diagnosed by pneumatic otoscopy by validated otoscopists, when children with acute onset of otalgia had tympanic membranes (TMs) that were: (1) bulging or full; and (2) a cloudy or purulent effusion was observed, or the TM was completely opacified; and (3) TM mobility was reduced or absent.

3. AOM Prone Children

An AOM prone child is a child having three episodes of AOM within 6 months or 4 episodes within one year were considered otitis prone while others who had fewer episodes were placed into the non-otitis prone group.

4. Antibiotic

"Antibiotic" or like words or other forms refers to a compound, substance, molecule, or composition, which acts to reduce, inhibit, or prevent an infection of a bacteria.

5. Assaying

Assaying, assay, or like terms refers to an analysis to determine a characteristic of a substance, such as a molecule or a cell, such as for example, the presence, absence, quantity, extent, kinetics, dynamics, or binding.

6. Assay Output

An "assay output" or like terms or other forms refers to the result or product from running an assay, such as data. For example, an assay output could be the fact that antibodies to P6 are present in a sample, after running the assay which tested whether anti-P6 antibodies were present or not. The assay can be expressed in a readout on a screen, on a paper, or in any other media, such as a computer disk etc., but it must be expressed. In other words, the fact of anti-P6 antibody presence is not the assay output, it is the expression of this fact in some tangible form that is the assay output.

7. Biological Sample/Sample

As used herein, the term "biological sample" or "sample" refers to any material or substance from an individual or patient that contains immune cells or antibodies. For example, the sample can be blood, serum, urine or any other type of fluid.

8. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

9. Comprise

Throughout the description and claims of this specification, the word "comprise" and variations of the word, such as "comprising" and "comprises," means "including but not limited to," and is not intended to exclude, for example, other additives, components, integers or steps.

10. Complex

The term complex as used herein refers to the association of a first molecule with an another molecule for which the first molecule has a binding affinity.

11. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

12. Contacting

Contacting or like terms means bringing into proximity such that a molecular interaction can take place, if a molecular interaction is possible between at least two things, such as molecules, cells, markers, at least a compound or composition, or at least two compositions, or any of these with an article(s) or with a machine. For example, contacting refers to bringing at least two compositions, molecules, articles, or things into contact, i.e. such that they are in proximity to mix or touch. For example, having a solution of composition A and cultured cell B and pouring solution of composition A over cultured cell B would be bringing solution of composition A in contact with cell culture B.

It is understood that anything disclosed herein can be brought into contact with anything else. For example, a sample can be brought into contact with a reagent, such as an antibody that binds P6, protein D and so forth.

13. Coapplication

"Coapplication" is defined as the application of one or more substances simultaneously, such as in the same formulation or consecutively, within a time frame such that each substance is active during a point when the other substance or substances are active.

14. Compounds and Compositions

Compounds and compositions have their standard meaning in the art. It is understood that wherever, a particular designation, such as a molecule, substance, marker, cell, or reagent compositions comprising, consisting of, and consisting essentially of these designations are disclosed. Thus, where the particular designation marker is used, it is understood that also disclosed would be compositions comprising that marker, consisting of that marker, or consisting essentially of that marker. Where appropriate wherever a particular designation is made, it is understood that the compound of that designation is also disclosed. For example, if particular biological material, such as EGF, is disclosed EGF in its compound form is also disclosed.

15. Control

The terms control or "control levels" or "control cells" or like terms are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard. For example, a control can refer to the results from an experiment in which the subjects or objects or reagents etc are treated as in a parallel experiment except for omission of the procedure or agent or variable etc under test and which is used as a standard of comparison in judging experimental effects. Thus, the control can be used to determine the effects related to the procedure or agent or variable etc. For example, if the effect of a test molecule on a cell was in question, one could a) simply record the characteristics of the cell in the presence of the molecule, b) perform a and then also record the effects of adding a control molecule with a known activity or lack of activity, or a control composition (e.g., the assay buffer solution (the vehicle)) and then compare effects of the test molecule to the control. In certain circumstances once a control is performed the control can be used as a standard, in which the control experiment does not have to be performed again and in other circumstances the control experiment should be run in parallel each time a comparison will be made.

16. Consisting Essentially of

"Consisting essentially of" in embodiments refers to, for example, a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, aberrant affinity of a stimulus for a cell surface receptor or for an intracellular receptor, anomalous or contrary cell activity in response to a ligand candidate or like stimulus, and like characteristics.

17. Comparing

"Comparing" or like words or other forms refers to the act of reviewing something in relation to something else.

18. Determining

"Determining" or like words or other forms refers to the act of settling or deciding by choice from different alternatives or possibilities.

19. Different Expression

The terms different expression and like terms can include any difference including at least a 1%, 5%, 10%, 15%, 20%, 30%, 40%, 50%, 75%, 100%, 300%, 500%, 750%, 1000%, 5000%, 10,000%, or 50,000% difference.

20. Ear Infection

A middle ear infection (acute otitis media) is characterized by inflammation of the ear drum (tympanic membrane) and the accumulation of fluid behind the ear drum within the middle ear space. Typically the middle ear fluid during AOM contains inflammatory and immune cells and immune cell products and either bacteria or viruses or both.

21. Epitope

As used herein, "epitope" refers to the region or fragment of an antigen that can be recognized by the immune system. Preferably, the epitope is recognized by antibodies, B cells or T cells. An epitope can be linear or conformational.

There are 3 commonly used monoclonal antibodies for P6: 3B9, 7F3 and 4G4. Apicella and coworkers mapped the P6 conformational epitope for antibody 3B9 using small peptides and competition binding experiments. The results of Apicella's experiments pointed to a non-continuous string of amino acids in the P6 sequence as being important for 3B9 binding: GNTDERGT . . . RR (residues 87-94 and 147-148). (Bogdan J A, Apicella M A (1995) Mapping of a surface-exposed, conformational epitope of the P6 protein of *Haemophilus influenzae*. Infect Immun 63: 4395-4401.) Murphy and coworkers proposed that the aspartate at position 59 is implicated in antibody 7F3 binding to P6 (Murphy T F, Kirkham C, Sikkema D J (1992) Neonatal, urogenital isolates of biotype 4 nontypeable *Haemophilus influenzae* express a variant P6 outer membrane protein molecule. Infect Immun 60: 2016-22). It has been confirmed that D59 was indeed part of the epitope to monoclonal antibody 7F3 using nuclear magnetic resonance spectroscopy and ELISA. (Michel L V, Kalmeta B, McCreary M, Snyder J, Craig P, Pichichero M E (2011) Vaccine candidate P6 of nontypable *Haemophilus influenzae* is not an outer membrane protein based on protein structural analysis, Vaccine 29: 1624-1627) It has also been shown that monoclonal antibody 4G4 competes for a similar epitope as 7F3 (Murphy T F, Kirkham C, Sikkema D J (1992) Neonatal, urogenital isolates of biotype 4 nontypeable *Haemophilus influenzae* express a variant P6 outer membrane protein molecule. Infect Immun 60: 2016-22 Bogdan J A, Apicella M A (1995) Mapping of a surface-exposed, conformational epitope of the P6 protein of *Haemophilus influenzae*. Infect Immun 63: 4395-4401), but no specific amino acids have been implicated in 4G4 binding. Additionally, the structure of P6 has been solved by nuclear magnetic resonance spectroscopy [Parsons L M, Lin F, Orban J. Peptidoglycan recognition by Pal, an outer membrane lipoprotein. Biochemistry 2006; 45: 2122-28].

22. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

23. Immune Response

"Immune response" is how the body recognizes and defends itself against foreign substances such as bacteria, viruses, toxins, drugs, etc. An immune response can also be the body's response to substances that appear to be foreign even if the substances are actually self proteins.

24. In Vitro In Vivo

The terms in vitro and in vivo as used herein have their usual and ordinary meanings in the art.

25. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

26. Infection

Infections of the human host are caused by bacteria, viruses, fungi and parasites. Infections elicit an inflammatory and immune response by the human host to eliminate the organism 27. Lung Infection Lung infections may be caused by bacteria, viruses, fungi and parasites and the pathological process is confined to the lower airways consisting of the trachea, bronchi, bronchioles and lung parenchyma.

28. Material

Material is the tangible part of something (chemical, biochemical, biological, or mixed) that goes into the makeup of a physical object.

29. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts. t is understood that molecules can include recombinant variations or humanized variations or oligomeric or non-oligomeric variations where appropriate.

30. Normalizing

Normalizing or like terms means, adjusting data, or a response, or an assay result, for example, to remove at least one common variable.

31. Optionally

"Optional" or "optionally" means that the subsequently described event or circumstance may or may not occur, and that the description includes instances where said event or circumstance occurs and instances where it does not.

32. Obtaining

"Obtaining" or like words or other forms refers to getting or receiving or attaining. It requires to a planned effort by the actor, but the plan can be in acceptance, for example, by accepting something that is given one.

33. Pharmacological Activity

As used herein, the term "pharmacological activity" refers to the inherent physical properties of a peptide or polypeptide. These properties include but are not limited to half-life, solubility, and stability and other pharmacokinetic properties.

34. Pneumonia

Pneumonia is an infection of the lung parenchyma. If the infection involves the bronchi it is often termed bronchitis or bronchopneumonia.

*Streptococcus pneumonia* is a bacteria that causes ear infections, sinus infections, bronchopneumonia, pneumonia, bacteremia, septicemia, meningitis, and other bloodstream-disseminated infections such as arthritis.

35. Positive Control

A "positive control" or like terms is a control that shows that the conditions for data collection can lead to data collection.

36. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

37. Prescribing, Prescription

"Prescribing" or "Prescription" or like words or other forms refers to a written direction or act for a therapeutic or corrective agent; specifically, such as one for the preparation and use of a medication.

38. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

39. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

40. Pro-Drug

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

41. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

42. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

43. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

44. RT, PCR, qPCR

"RT, PCT, and qPCR" refer to molecular biology techniques, Reverse Transcriptase, Polymerase Chain Reaction, and quantitative PCR respectively. These techniques allow for the detection and amplification of nucleic acids from cells.

45. Sinus Infection

Sinus infections are commonly termed sinusitis or rhinosinusitis. Inflammation occurs in the sinus spaces, consisting of the maxillary, ethmoid, frontal and sphenoid sinuses.

46. Subject

As used throughout, by a "subject" is meant an individual. A subject can be a patient. A subject can be preferably less than 18, 17, 16, 15, 14, 13, 12, 11, 10, 9, 8, 7, 6, 5, 4, 3, 2, or 1.

47. Standard

A "standard" or like terms or other forms refers to an established rule or measure that has been previously determined, but which can be used for comparative purposes. It often is used like a control, and often it is produced by running a control or multiple control experiments to determine a consistent or average result as a "control."

48. Substance

A substance or like terms is any physical object. A material is a substance. Molecules, cells, proteins, and DNA can be considered substances. A machine or an article would be considered to be made of substances, rather than considered a substance themselves.

49. Tissue

Tissue or like terms refers to a collection of cells. Typically a tissue is obtained from a subject.

50. Transmitting the Assay Output to a Recipient

"Transmitting the assay output to a recipient" or like terms or other forms refers to the act of sending an assay output. This can refer to for example, refer to an email from a computer, automatically generated to, for example, a doctor or doctor's office.

51. Treating

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertantly cause harm.

52. Treatment

By "treatment" and "treating" is meant the medical management of a subject with the intent to cure, ameliorate, stabilize, or prevent one or more symptoms of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes prophylactic or palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

53. Therapeutically Effective

The term "therapeutically effective" means that the amount of the composition used is of sufficient quantity to ameliorate one or more causes or symptoms of a disease or disorder. Such amelioration only requires a reduction or alteration or decrease, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

Those skilled in the art will recognize, or be able to ascertain using no more than routine experimentation, many equivalents to the specific embodiments of the invention described herein. Such equivalents are intended to be encompassed by the following claims.

EXAMPLES

A. Example 1

Bactericidal Antibody Response Against P6, Protein D and OMP26 of Non Typeable *Haemophilus influenzae* (NTHi) after Acute Otitis Media (AOM) in Otitis Prone Children 1. Background Nontypeable *Haemophilus influenzae* (NTHi) is one of the major causes of infections in the upper respiratory tract and middle ear leading to AOM. Bactericidal antibody provides protection from AOM caused by NTHi. Understanding the contributions of bactericidal antibody specific to potential vaccine antigens will help in the design of a novel vaccine, which could protect against NTHi infections.

Protein D, P6, and OMP26 are three conserved outer membrane proteins of NTHi currently being considered as vaccine candidates against infections caused by NTHi.

The aim of the present study was to investigate the antigen specific bactericidal antibody response, to protein D, P6 and OMP26 in otitis prone children.

2. Methods i. Study Design

The patients constituted a consecutively studied series of 27 children; aged 7 months to 28 months of age (mean 15.41±5.7 mo) who were otitis prone between the age of 6 and 36 months. From these 27 children we had 16 acute sera collected at the time of diagnosis of AOM caused by NTHi and 26 serum samples from the convalescent stage.

ii. Tympanocentesis

All diagnoses of AOM for the defining event that caused the child to meet the definition of otitis prone was confirmed by tympanocentesis. Middle ear fluid (MEF) for culture was obtained by puncture of the inferior portion of an intact TM with a 20-gauge spinal needle attached to a 3-mL syringe using a hand-held operating otoscope. If a small sample of MEF was obtained on aspiration, 0.5 ml of trypticase soy broth was aspirated through the spinal needle and then aliquoted and inoculated onto agar plates and into broth, as described below.

iii. Bacteriology

Middle ear fluid were cultured on chocolate agar plates and inoculated in BHI with 15% glycerol and preserved at −80 degree. The NTHi strains were identified by standard laboratory procedures. An isolate was identified as NTHi based on colony morphology, porphyrin reactivity, and growth requirement for hemin and nicotinamide adenine dinucleotide using *Haemophilus* ID Quad plates [McCrea et al., J. Clin. Microbiol. 2008; 46: 406-416].

iv. Purification of P6, OMP26 and Protein D

Recombinant protein D was obtained from GlaxoSmithKline (GSK, Rixensart, Belgium). The P6 plasmid was obtained from Tim Murphy, University of Buffalo and the OMP26 plasmid was obtained from Jennelle Kyd, University of Canberra, Australia. P6 and OMP26 were expressed in *E. coli* BL21 (DE3). P6 was expressed predominantly as inclusion bodies and purified under denaturing conditions. OMP26 was expressed in soluble fraction and purified under native conditions. The purification was carried out with an already published procedure [Adhami et al., Infection and Immunity 1999; 67: 1935-1942; Bhushan et al., Infection and Immunity 1997; 65: 2668-75]. The purity of purified recombinant proteins was assessed by SDS-PAGE.

v. Bactericidal Assay

Forty two serum samples were screen for bactericidal activity against their homologous NTHi strain (isolated from MEF of that child). 21 bactericidal serum samples were selected to assess bactericidal activity against a heterologous strain (86-028 NP provided as a gift from Lauren Bakaletz, Ohio State University, Columbus, Ohio). The sera were heat-inactivated at 56° C. for 30 minutes to eliminate human complement. Homologous and heterologous NTHi strains were cultivated, harvested, and diluted to a concentration of $\sim 10^5$ CFU/ml. Twelve serial twofold dilutions of the serum to be tested (starting at 1:2) were mixed with precolostral calf serum complement (PCCS) and 20 µl of bacteria. After 60 minutes of incubation, the number of surviving bacteria was determined by plating 5 µl onto chocolate agar and counting the colonies. The bactericidal titer of the serum was defined as the inverse of the highest dilution that led to 50% bacterial killing and was compared to that of negative control (complement plus bacterium). In house developed appropriate controls were included in all experiments.

vi. Adsorption of Anti P6, Protein D and OMP26 Antibodies from Sera

The bactericidal sera were later depleted for anti protein D, P6, and OMP26 specific antibodies and used for bactericidal assay. For the absorption procedure, polystyrene beads were washed extensively with borate buffer (pH 8.5) and resuspended in 1 ml of Borate buffer. Recombinant protein D, P6 and OMP26 antigens were incubated with these beads overnight at room temperature. The beads were washed extensively, incubated in BSA/Borate buffer for 30 minutes at room temperature, then pelleted and incubated with 200 µl of patient sera for 2 hours at room temperature. The beads were centrifuged (200×g) and the supernatant was collected. The anti protein D, P6 and OMP26 absorbed sera levels were measured by ELISA (below mentioned) and used for bactericidal assays. The reciprocal bactericidal titers were compared with unadsorbed sera to determine the bactericidal activity mediated by each of the specific antibodies.

vii. Detection of P6, Protein D and OMP26 Specific IgG by ELISA

Protein D, P6 and OMP26 specific IgG antibody titers in the acute and convalescent serum samples were determined by ELISA. Protein D, P6 and OMP26 recombinant proteins were coated on 96 well plate with the concentration of 0.25 ug/ml each in coating buffer. After blocking with 3% skim milk, diluted serum samples were added to the wells, and the mixture was incubated at room temperature for 1 h. affinity purified goat anti human IgG antibody conjugated to horseradish—peroxidase was used as a secondary antibody. The reaction products were developed with TMB Microwell peroxidase substrate system, stopped by the addition of 1.0 M phosphoric acid, and read by ELISA reader at 450 nm.

viii. Detection of Whole Cell NTHi IgG Antibodies by ELISA

For the whole cell specific ELISA, for each child their homologous NTHi strain isolated from MEF and a heterologous strain (86-028 NP) were used. Homologous and heterologous strains were grown on chocolate agar and further inoculated into brain heart infusion broth supplemented with NAD and Hemin. The bacteria were grown to mid log phase, harvested, and washed with PBS containing 0.15 mM CaCl2, and 0.5 mM MgCl2. The pellet was finally suspended and diluted to an OD of 1 at 490 nm. The NTHi preparation was used to coat 96-well plates. After blocking with 1% gelatin and washing, diluted serum was added to the wells, and the mixture was further incubated at room temperature for 1 h. Affinity purified goat anti human IgG antibody conjugated to alkaline phosphatase was used as a secondary antibody. The reaction products were developed with PNP dissolved in diethanolamine buffer. The reaction was stopped by the addition of 2M NaOH and was read by ELISA reader (molecular devices) at 405 nm. Titers for test samples were determined relative to a reference serum run on the same plate, and values were expressed relative to reference serum.

ix. Statistics

Student t test was used to analyze the significance of antibody changes. P value<0.05 was considered as significant. Statistical analysis of correlation coefficients by linear regression ($r^2$) between ELISA titers and bactericidal titers was determined measure the level of correlation between the assays.

3. Results

Figures 1A, 1B:
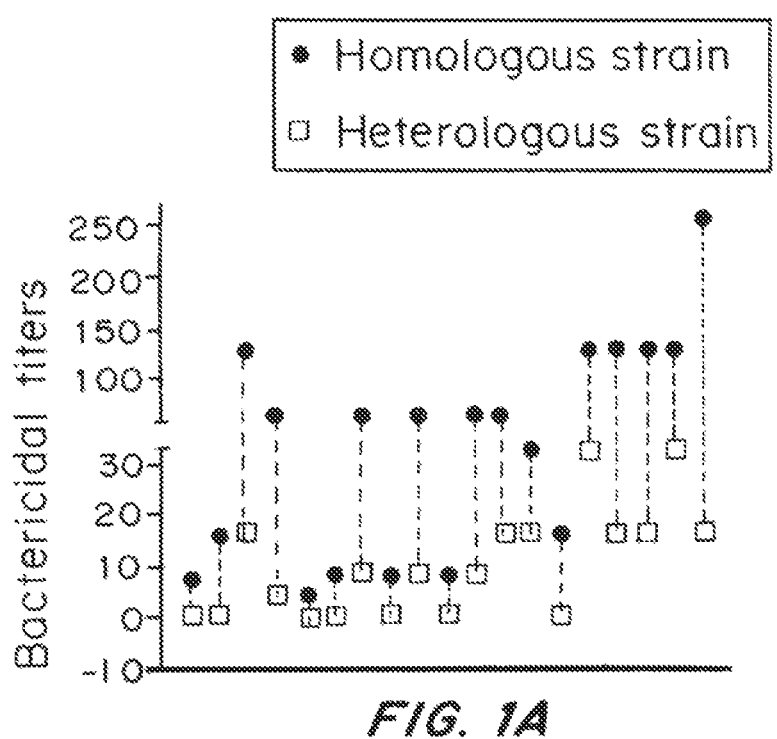
FIGS. 1A, 1B, 1C and 1D are graphs of antibody titers.

The bactericidal antibody response to 3 nontypeable *Haemophilus influenzae* (NTHi) outer membrane proteins (Protein D, P6 and OMP26) was studied in 27 otitis prone children (age 7-28 months) after an acute otitis media (AOM) caused by NTHi. Among 17 acute serum samples, only 4 sera (24%) had detectable bactericidal activity versus 18 of 25 convalescent serum samples (72%). 11 sera (58%) had bactericidal activity against a heterologous NTHi strain but the titers were significantly lower (p=0.0023) as compared to the homologous strains. Levels of protein D (p 0.002) (FIG. 1C) and P6 (p=0.003) (FIG. 1B) but not OMP26 antibodies were higher in bactericidal sera compared to non bactericidal sera.

Figure 1C:
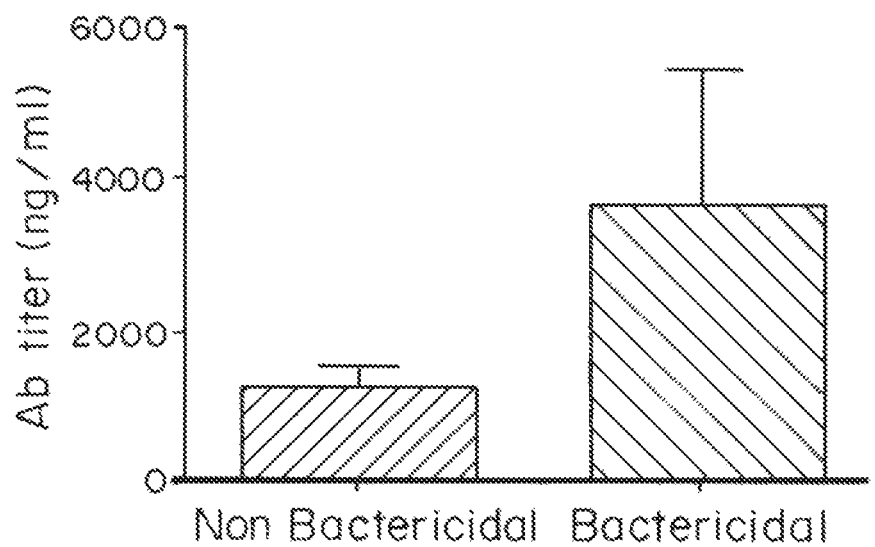
Figure 1D:
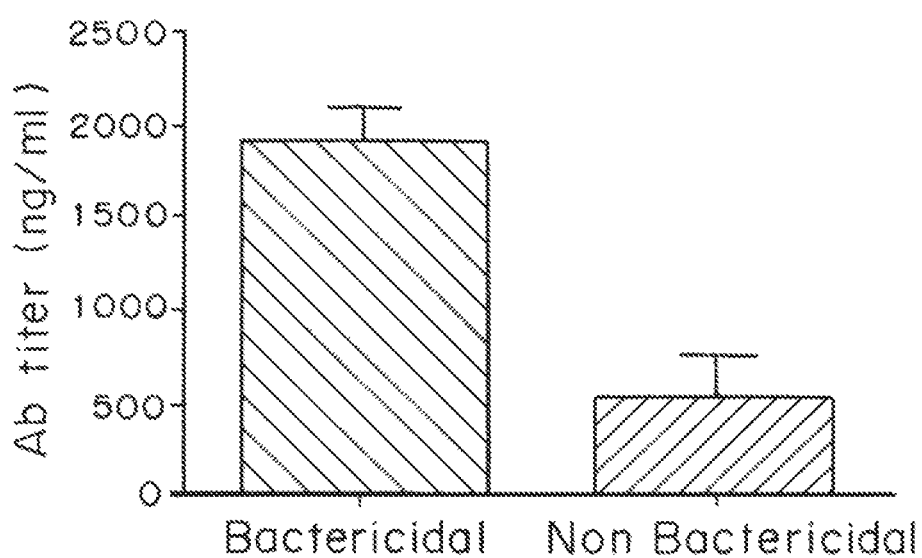
Figure 2A:
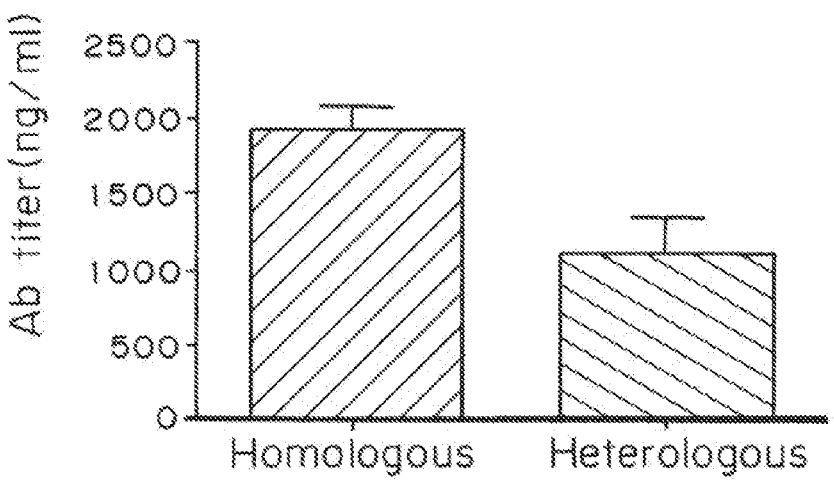
FIG. 2A is a graph of the NTHi whole cell antibody titers against homologous and heterologous NTHi strains in bactericidal sera elicited in children with AOM.

Serum IgG antibody levels to whole cell homologous and heterologous NTHi strains were measured and compared in bactericidal and non-bactericidal serum samples. FIG. 1D illustrates that the 95% confidence interval was 768 to 1994 and whole cell IgG titers were significantly higher in bactericidal sera as compared to non-bactericidal sera (p=0.001). The 95% confidence interval between the whole cell ELISA for homologous and heterologous strains was 199 to 1421 and titers were significantly higher for homologous NTHi strains as compared to the heterologous strain (p=0.03) (FIG. 2A).

Figure 2B:
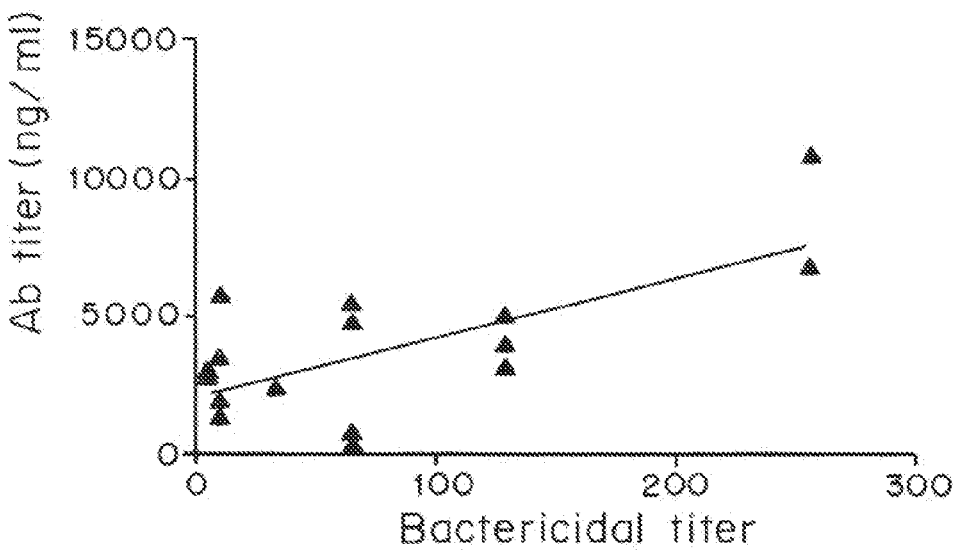
FIGS. 2B and 2C are graphs of the correlation of anti protein D and P6 IgG titers and bactericidal titers, respectively.
Figure 2C:
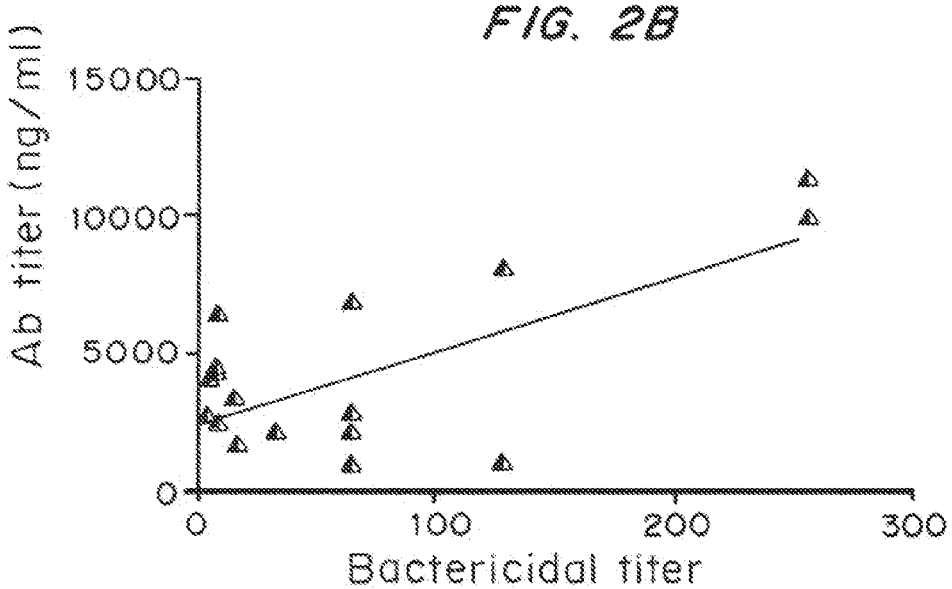
Figures 3A, 3B, 3C, 3D:
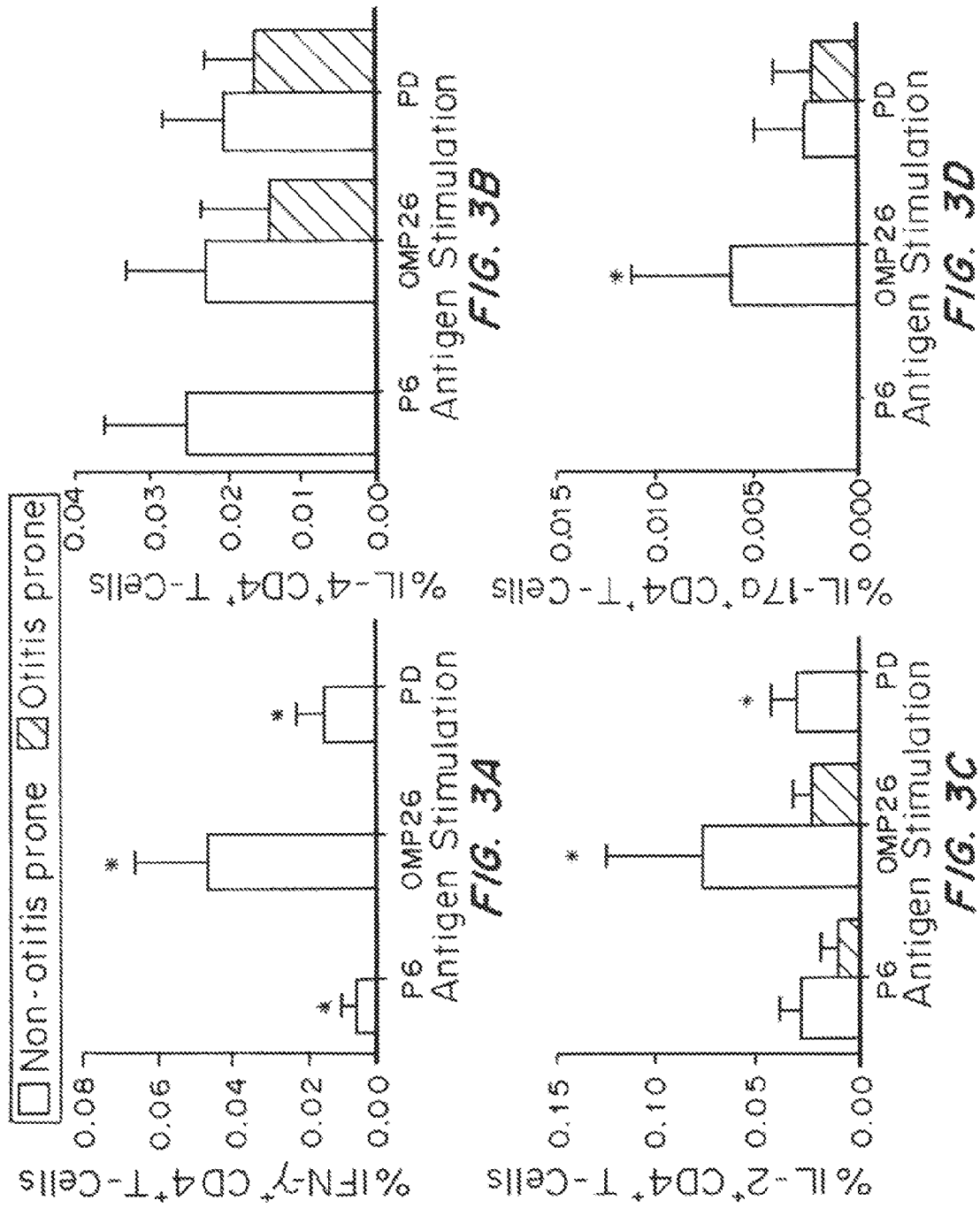
FIGS. 3A, 3B, 3C and 3D are graphs of percent frequencies of NTHi antigen specific memory CD4+ T cells. A) IFN-γ, B) IL-4, C) IL-2, and D) IL-17A, in the circulation of OP and NOP children against NTHi antigens (P6, OMP26, and Protein D). Bar graphs represent mean percentage values of CD69+CD4+ T cells gated on CD45RAlo following antigen stimulation+/−SE. *p<0.05 (n=10 each group; OP: average age 14.5 months and NOP: average age 8.2 months).

Serum IgG titers (protein D and P6) and bactericidal titers correlated (r=0.44 for protein D and 0.48 for P6; p=0.07 and 0.002, respectively) (FIGS. 2B and 2C). For 3 (14%) and 18 (86%) of 21 bactericidal sera tested, removal of anti-protein D and P6 antibody, respectively resulted in a significant drop in bactericidal antibody (p<0.005 for P6) (Table 1). Two children showed 25% bactericidal activity directed towards protein D and one child showed 50% bactericidal activity directed to protein D. For 18 (86%) of the same 21 bactericidal sera tested, a significant drop in bactericidal activity was measured after removal of P6 antibody from sera (p<0.005). P6 specific bactericidal antibody in the 18 serum samples accounted for almost 50% of the total bactericidal activity measured. OMP26 was not observed to contribute in bactericidal activity as the removal of OMP26 antibody did not change the bactericidal titers (data not shown).

TABLE 1

Representation of the relative contribution of anti P6 and protein D antibodies in total bactericidal activity in bactericidal serum samples

| Patient No | Bactericidal Titers Pre adsorption | Bactericidal titers post adsorption (P6) | Bactericidal titers post adsorption (protein D) |
|---|---|---|---|
| 06-01-041(AOM1 F/U) | 8 | 4 | 6 |
| 06-01-023 (AOM1 F/U) | 16 | 4 | 16 |
| 07-01-061(AOM1 F/U) | 128 | 64 | 128 |
| 06-01-006 (AOM1) | 64 | 32 | 64 |
| 07-01-062 (AOM1) | 4 | 4 | 4 |
| 07-01-062 (AOM1 F/U) | 32 | 16 | 24 |
| 08-01-078 (AOM2) | 8 | 4 | 4 |
| 08-01-78 (AOM2 F/U) | 64 | 32 | 64 |
| 06-01-037 (AOM1 F/U) | 8 | 4 | 8 |
| 07-01-051 (AOM1 F/U | 64 | 16 | 64 |
| 06-01-006 (AOM1 F/U) | 8 | 4 | 8 |
| 06-01-031 (AOM1 F/U) | 64 | 32 | 64 |
| 06-01-021 (AOM1 F/U) | 64 | 16 | 64 |
| 06-01-035 (AOM1 F/U) | 16 | 8 | 16 |
| 06-01-043 (AOM1 F/U) | 128 | 128 | 128 |
| 09-03-085 (AOM2 F/U) | 8 | 4 | 8 |
| 01-072 (AOM2 F/U) | 128 | 32 | 128 |
| 03-066 (AOM2 F/U) | 128 | 64 | 128 |
| 01-038 (AOM1 F/U) | 128 | 64 | 128 |
| 01-033 (AOM1 F/U) | 256 | 128 | 256 |
| 09-01-093 (AOM1 F/U | 4 | 4 | 4 |

Anti protein D, P6, and OMP26 specific antibodies were selectively depleted from 21 bactericidal sera in order to assess their relative contribution in total bactericidal antibody titers. After absorption all sera were tested for residual antibody to protein D, P6, and OMP26 by ELISA to demonstrate the absorption was complete (data not shown). Cross adsorption experiments were performed to demonstrate that the adsorption was quite specific. For instance, P6 and OMP26 ELISA titers were quantified in sera which were adsorbed for Protein D antibodies and results showed that there was no cross adsorption. Each adsorption experiment was carried out on two different occasions to look at the reproducibility of results and ELISA titers were established after every adsorption.

4. Conclusions

In this study, the bactericidal antibody response was measured against three vaccine candidate proteins of NTHi—protein D, P6, and OMP26—in otitis prone children. This is the first study to assess the proportional contribution of serum bactericidal activity against these three conserved outer membrane proteins of NTHi. These data indicate several important findings: 1. Bactericidal antibody in otitis prone children is infrequently present in acute sera but present in the majority of children in convalescence 2. The bactericidal antibody that otitis prone children develop is primarily but not exclusively to the homologous infecting strain. 3. Total antibody to protein D and P6 partially correlate with bactericidal antibody 4. Protein D does not elicit bactericidal antibody in a majority of otitis prone children. 5. P6 does elicit bactericidal antibody in a majority of otitis prone children. 6. OMP26 elicits no detectable bactericidal antibody in otitis prone children. 7. A variable proportion of serum bactericidal antibody is not directed against protein D or P6 and must be directed to other unconserved or conserved outer membrane proteins.

Shurin et al, (1980) suggested that bactericidal activity in sera to the homologous strain develops during the convalescent stage of non otitis prone children [Shurin et al., The Journal of Paediatrics 1980; 97: 364-369]. Later, Yamanaka and Faden (1992) showed that acute sera infrequently had bactericidal antibodies to homologous NTHi following AOM [Yamanaka and Faden, The Journal of Pediatrics 1992; 122: 212-218]. Faden et al (1989) reported that the bactericidal antibody response is NTHi strain specific and provided little or no cross protection in otitis prone and non otitis prone children with otitis media [Faden et al., The Journal of Infectious Disease 1989; 160: 999-1004]. Bernstein et al (1991) found in three otitis prone children that the bactericidal antibody response was not cross protective against a heterologous strain of NTHi causing a second or third episode [Bernstein et al., Otolaryngology—Head and Neck Surgery 1991; 105: 406-410]. The findings of the current data are in agreement with some aspects of previous work in regards to bactericidal antibody directed to the homologous strain prior to and after an NTHi AOM. However, bactericidal activity against a heterologous strain was not found in otitis prone children, albeit at lower titers as compared to the homologous strain. In the present study, the detection of bactericidal antibody titers in otitis prone children argues against the notion that these children are incapable of generating immune responses to NTHi as an otopathogen. However the differences between homologous and heterologous strain bactericidal activity suggests a probable reason of failure to protect against heterologous new infections and points to the necessity of a multi-component NTHi vaccine.

The focus of the comparative analysis of bactericidal antibody and antibody class was centered on IgG. The IgM responses were not taken into consideration, as they are not predictive of immunological memory or affinity maturation. Chen at al (1999) demonstrated that serum IgG levels are higher in bactericidal sera against *Moraxella catarrhalis* in healthy adults and children [Chen et al., Infection and Immunity 1999; 67: 1310-1316]. IgG antibodies to P6 have been found to be bactericidal in an experimental animal system [De Maria et al., Infection and Immunity 1996; 64: 5187-5192] and to be associated, in part, with the bactericidal activity in otitis prone children [Sabirov et al., Paediatric Research 2009; 66: 565-570]. Consistent with those previous findings and Yamanaka and Faden in otitis prone children [Yamanaka and Faden, The Journal of Pediatrics 1992; 122: 212-218], higher IgG anti P6 levels were found in bactericidal sera of otitis prone children.

A modest correlation was found between bactericidal titers and serum IgG antibody concentrations for protein D and P6 but not OMP26. It is not fully understood whether the lack of a stronger correlation is related to a disparity in antibody avidity as detected in the two assays. In the past also, high IgG antibody levels against P6 with no commensurate bactericidal activity has been attributed to IgG antibody of affinity and/or, antibodies directed against certain non-critical epitopes [Yamanaka and Faden, The Journal of Pediatrics 1992; 122: 212-218]. Avidity of antibody in children improves with age and immune maturation [Pollard et al., The Lancet 2000; 356: 2065-66; Maslanka et al., Infection and Immunity 1998; 66: 2453-59]; this area needs further investigation. No correlation was found between OMP26 IgG levels and bactericidal titers (data not shown) and OMP26, consistent with one previous report [Cripps and Otczyk, Exp Rev 685 Vaccines 2006; 5:517-34].

Significantly higher whole cell ELISA titers were found in bactericidal sera as compared to non bactericidal sera. The IgG titers were significantly higher for the homologous strain as compared to the heterologous strain. The results were quite comparable with the serum IgG titers for P6 and protein D in bactericidal and non bactericidal sera. There is limited literature on the relationship of whole cell ELISA titers and bactericidal titers. The present study indicates that bactericidal sera would have higher IgG titers against the homologous strain than non bactericidal sera and heterologous NTHi strains.

This study is the first to examine the exact proportion of bactericidal antibody directed against protein D, P6 and OMP 26 in otitis prone children after AOM. Forsgren has previously shown that antibody to protein D was bactericidal in rat model [Kyd and Cripps, Infect Immun 1998; 66: 2272-2278; Forsgreen et al., Clinical Infectious Disease 2008; 46: 726-31]. The role of protein D in bactericidal activity in children following AOM has not been previously studied. The results indicate that protein D specific antibodies contribute to bactericidal activity in about 25% of otitis prone children. In contrast the contribution of anti-P6 antibody to bactericidal activity in over 80% of otitis prone children is noteworthy, especially since the anti-P6 antibody appeared to contribute about 50% of the total bactericidal activity in many sera.

Among the 21 bactericidal sera, the proportion of bactericidal antibody response to three conserved outer membrane antigenic determinants did not exceed more than 50% in 18 sera. This result indicates that a significant percentage of bactericidal antibodies are directed to other proteins. The structurally non-conserved porins are one of the classes of proteins on the NTHi surface that have been shown to elicit bactericidal antibodies [Neary et al., Infection and Immunity 2001; 69:773-778; Sikkema and Murphy, Infection and Immunity 1992; 60:5204-5211]. Nevertheless, there might be other yet unidentified, conserved targets for bactericidal antibodies to NTHi.

The children above 6 months were deliberately taken for the study to have the minimal effect mediated by the maternal antibodies in the serum [Zinkernagel, The New England Journal of Medicine 2001; 345:1331-1335]. Therefore it was assumed that the bactericidal activity detected in the otitis prone children is totally conferred by their own immune system and not by passive transfer from mother.

In summary, the findings establish that a significant portion of bactericidal activity is directed to OMP P6 and to a lesser degree to protein D in otitis prone children following a naturally acquired AOM infection by NTHi. The contribution of other NTHi conserved antigens displayed on the NTHi surface is encouraged by the results herein. The lack of a strong correlation between bactericidal antibody titers and IgG titers indicates the need to establish a biologically relevant serologic surrogate to define a particular bactericidal titer, a threshold for defining a protective titer, which is critical for vaccine development.

B. Example 2

T Cells and AOM

1. Introduction

*Streptococcus pneumoniae* (Spn) and non-typeable *Haemophilus influenzae* (NTHi) are the two most common pathogens causing AOM [Casey et al., Pediatr. Infect. Dis. J. 2010; 29(4):304-9]. In animal models, $CD4^+$ T lymphocytes have been shown to be critical for protective immunity against these prevalent bacterial respiratory pathogens [Malley et al., Proc. Natl. Acad. Sci. U.S.A 2005; 102(13):4848-53; McCool and Weiser, Infect. Immun 2004; 72(10):5807-13; Snapper et al., Trends Immunol. 2001; 22(6):308-11]. More recently, Th-17 cells secreting IL-17, IL-21, and IL-22 have been described to impart antibody independent protection in mouse model of pneumococcal infection [Malley et al., Infect. Immun 2006; 74(4):2187-95]. In older children (median age 5 years) and adults, antigen-specific $CD4^+$ T-cells has been shown to reduce Spn nasopharyngeal colonization [Mureithi et al., J. Infect. Dis. 2009; 200(5):783-93; Zhang et al., J. Infect. Dis. 2007; 195(8):1194-202]. An effective pathogen-specific T-cell response in adults has been associated with protection from invasive Spn disease (IPD) and chronic obstructive pulmonary disease (COPD) caused by Spn and NTHi respectively [King et al., Am. J. Respir. Crit Care Med. 2003; 167(4):587-92; de Bree et al., J. Infect. Dis. 2007; 195(11):1718-25]. However, there are no data that correlate a protective role of $CD4^+$ T-helper subsets among children experiencing AOM.

Robust memory T- and B-cell responses are generated during both onset of a natural infection as well as upon vaccination, with memory lymphocytes populating lymphoid and non-lymphoid sites [de Bree et al., J. Infect. Dis. 2007; 195(11):1718-25; Lanzavecchia and Sallusto, Curr. Opin. Immunol. 2009; 21(3):298-304; Kelly et al., JAMA 2005; 294(23):3019-23]. Once generated, memory T-cells and antibodies can be detected in the blood circulation over a period of time [de Bree et al., J. Infect. Dis. 2007; 195(11):1718-25; Pitcher et al., Nat. Med. 1999; 5(5):518-25]. In both humans and mice, $CD4^+$ T-cells comprise functionally distinct populations characterized by specific cytokine profiles produced in response to antigens [Fietta and Delsante, Annu. Rev. Immunol. 2009; 27:485-517; Korn et al., Annu. Rev. Immunol. 2009; 27:485-517]. More recently, follicular helper T (Tfh) cells have been shown as a major subset to provide help to B-cells for antibody responses [Fazilleau et al., Immunity. 2009; 30(3):324-35; Yu and Vinuesa, Trends Immunol. 2010; 31(10):377-83; Morita et al., Immunity. 2011; 34(1):108-21].

To explain the immunological dysfunction that leads to recurrent AOM, earlier studies have found lower levels of otopathogen-specific antibody concentrations in otitis prone children, as compared to non-otitis prone children [Faden, Eur. J. Pediatr. 2001; 160(7):407-13; Pichichero et al., Vaccine 2010; 28:7184-7192]. This work provides a better understanding of the immunologic dysfunction in otitis prone children, focusing on the generation of different subsets (Th1, Th2 & Th-17) of memory $CD4^+$ T-helper cells in correlation with B-cell antibody responses as a possible novel explanation. Using six pneumococcal and three NTHi protein antigens, we enumerated Spn and NTHi-specific functional $CD4^+$ T-helper memory cell subsets in the peripheral blood of a cohort of non-otitis prone and otitis prone children. Serum IgG responses were also measured to the same antigens in these children.

2. Methods i. Subjects

Subjects were participants from a 5-year prospective longitudinal AOM study funded by the NIH NIDCD [Pichichero et al., Vaccine 2010; 28:7184-7192]. Enrolled children were from a middle class, suburban socio-demographic population in Rochester N.Y. Healthy children at age of 6 months without prior AOM were enrolled and had blood, nasopharyngeal (NP) and oropharyngeal (OP) cultures obtained seven times, at the age of 6, 9, 12, 15, 18, 24 and 30 months. Middle ear fluid (MEF) was obtained by tympanocentesis during AOM episodes. Colonization with Spn and/or NTHi in the NP/OP and MEF was routinely determined by standard microbiologic culture. To identify the otitis prone child in the study population all the children had tympanocentesis-confirmed infections and all received antibiotic therapy directed to the otopathogen isolated from middle ear fluid for each AOM event. PBMCs were isolated from the collected blood and frozen in the liquid nitrogen until used. Children having three episodes of AOM within 6 months or 4 episodes within one year were considered otitis prone while others who had fewer episodes were placed into the non-otitis prone group. Written informal consent was obtained in association with a protocol approved by the Rochester General Hospital Investigational Review Board.

ii. Antigens

Six different pneumococcal protein antigens were used in this study: pneumococcal histidine triad proteins D (PhtD) and E (PhtE), LytB, PcpA, PlyD1 (a detoxified derivative of pneumolysin which has three point mutations that do not interfere with anti-pneumolysin antibody responses) and PspA. *Haemophilus influenzae* protein antigens used were P6, OMP26, and Protein D. An optimal dosage for stimulation was determined by absence of detectable cell toxicity, by the use of tryptan blue staining and/or flow cytometry analysis after propidium iodide staining (data not shown). Staphylococcal enterotoxin B (Sigma, St Louis) was used as a positive control.

iii. T Cell Stimulation

T cell stimulation and intracellular cytokine profiling was standardized in our laboratory adapted from elsewhere [Lamoreaux et al., Nat. Protoc. 2006; 1(3):1507-16]. Briefly, PBMCs were stimulated with the six pneumococcal antigens or the three NTHi antigens individually depending on the NP colonizing or AOM causative pathogen. Prior to stimulation, frozen PBMCs were quickly thawed in a 37° C. water bath followed by slowly adding complete culture medium (RPMI 1640 supplemented with 10% of FBS, 2 mM L-glutamine, 0.1 mM sodium pyruvate, nonessential amino acids, 100 U/mL penicillin, 100 µg/mL streptomycin). Cells were then washed and rested overnight in complete culture media in 24-well plates. PBMCs were stimulated using a standardized protocol in our laboratory. Briefly, cells were counted and $1\times10^6$ cells were placed in the each well of a 96-well flat bottom culture plate for stimulation with either 1 µg/ml of various protein antigens individually or with 1 µg/ml of Staphylococcal enterotoxin B (SEB). Cells left untreated served as negative controls. Cells were then incubated for 2 h at 37° C. in the presence of 5% $CO_2$ for antigen processing. After 2 hours, Golgi transport inhibitors (Brefeldin A and Monensis; BD Biosciences) were added to preserve cytokines intracellularly and incubation was then continued for an additional 4 hours. To the cells 1 µg/ml concentrations of anti-CD28 and anti-CD49d antibodies (clones L293 and L25 respectively; BD Biosciences) were added to provide co-stimulation and enhance the detection of antigen specific responses. Anti-CD28 and CD49d antibodies have been widely used for co-stimulation without affecting background levels [Pitcher et al., Nat. Med. 1999; 5(5):518-25].

iv. Cell Surface Staining and Cytokine Profiling

An intracellular cytokine staining assay (ICCS) was used to evaluate antigen specific $CD4^+$ T-cell subsets (Th-1, Th-2 and Th-17). After stimulation, cells were transferred to 96-well V-bottom plates and washed once with FACS buffer (PBS with 5% FBS) and stained with the antibodies to various cell surface markers. Antibodies used were anti-CD4 APC Alexafluor 750 (clone RPA T4, eBiosciences), PE-Texas Red anti-CD45RA (clone MEM56, Invitrogen), anti-CCR7 PerCP/Cy5.5 conjugate (clone TG8/CCR7, Biolegend). To identify Tfh cells in the PBMC samples, cells were surface stained with anti-CXCR5 perCP cy5.5 (Biolegend) anti-CD4 APC Alexafluor 750, PE-Texas Red anti-CD45RA and anti-CD3 Qdot (clone UCHT1, Invitrogen) separately. Cells were then permeabilized with fixation and permeabilization solution (BD Biosciences) for 20-minutes and washed three times with 1× permeabilization buffer (BD Biosciences). A cocktail of various cytokine specific antibodies was used to stain intracellularly captured cytokines as a result of stimulation. Antibodies used were PE-Cy7 conjugated anti-IFN-γ (clone B27, BD biosciences), Pacific blue conjugated anti IL17A (clone BL168, Biolegend), Alexa fluor 700 anti IL-2 (clone MQ1-17H12, Biolegend), PE conjugated anti IL-4 (clone 8D4-8, BD Biosciences), AF 488 conjugated TNF-α, anti-CD3 Qdot 605 (clone UCHT1, Invitrogen) and PE-Cy5 anti-CD69 (clone FN50, BD biosciences). After intracellular staining, cells were further washed 3-times with 1× permeabilization buffer and one final wash with FACS buffer before resuspending them into the FACS tubes. A custom made BD LSR II flow cytometer equipped for the detection of 12 fluorescent parameters was used to collect $2\text{-}5\times10^5$ events for each sample and data was analyzed using FLOW JO (Tree Star) software. Gates for cytokine positive cells were determined by the help of unstimulated and SEB stimulated cells and cytokine responders were confirmed by excessive back-gating.

v. Humoral Responses

For measuring IgG antibody levels in the samples, ELISA was performed as described previously [Pichichero et al., Vaccine 2010; 28:7184-7192]. Briefly, 96-well ELISA plates (Nunc-Immulon) were coated with 0.5 µg/ml of individual antigens (100 µl/well) in coating buffer (bicarbonate, [pH 9.4]) and incubated overnight at 4° C. After washing, the plates were blocked with 3% skimmed milk at 37° C. for 1 hr (200 µl per well). After five washes, 100 µl of serum at a starting dilution of 1:100 (in PBS-3% skim milk) was added to the wells and diluted serially 2 fold. The mixture was incubated at room temperature for 1 hr followed by the addition of affinity purified goat anti-human IgG, IgM or IgA antibody conjugated to horseradish-peroxidase (Bethyl Laboratories, Inc, Montgomery, Tex.) as a secondary antibody. The reaction products were developed with TMB Microwell Peroxidase Substrate System (KPL, Gaithersburg, Md.), stopped by the addition of 1.0 molar phosphoric acid and read by an automated ELISA reader using a 450-nm filter. To provide quantitative results on antibody concentrations, the level of the specific antibody present in the unknown sample was determined by comparison to an internal reference serum (pool of human serum with high antigen titers). The levels of IgG in the reference serum were quantitatively measured by using a human IgG ELISA quantitation kit (Bethyl laboratories). A Four-parameter logistic-log function was used to form the reference and sample curves.

vi. Statistics

All data was analyzed using Graph Pad Prism software. Two tailed P values for the data were calculated using Mann Whitney Test. Percentages of atopy and non-atopy between all non-otitis prone and otitis prone children were compared using chi-square method.

3. Results i. Study Population

From a total study population of 387 children 19 otitis prone children were identified. From the remainder children those with 1 or 2 AOMs who were of a similar age as the non-otitis prone children were randomly selected as comparators for the study. Clinical characteristics of the study children are shown in Table 2. No significant differences were found in atopic and non atopic children between the two cohorts (p=0.5).

TABLE 2

Basic characteristics of Study subjects

| | Pneumococcal | | NTHi | |
|---|---|---|---|---|
| | Otitis prone (n = 13) | Non-otitis prone (n = 14) | Otitis prone (n = 6) | Non-otitis prone (n = 6) |
| Gender | | | | |
| Male | 9 | 10 | 3 | 2 |
| Female | 4 | 4 | 3 | 4 |
| Mean Age (months) | 13.5 | 10.1 | 14.3 | 8.2 |
| Number of AOM episodes | | | | |
| >3 in 6 months | 6 | 0 | 5 | 0 |
| >4 in 12 months | 7 | 0 | 1 | 0 |
| Number of NP colonizations with respective pathogen | | | | |
| 1-3 | 10 | 10 | 4 | 5 |
| 4-5 | 3 | 1 | 1 | 0 |
| 6 or more | 0 | 0 | 1 | 0 |
| Ventilation tube placement | 4 | None | 3 | None |
| Adenoidectomy | None | None | None | None |
| Breast feeding | 12 | 8 | 3 | 1 |
| Atopy | 7 | 4 | 4 | 1 |
| Non Atopic | 6 | 10 | 2 | 5 | ii. Otitis Prone Children have Reduced Percentages of Antigen Specific Functional T-Helper Memory Responses to Spn and NTHi in their Circulation.

The circulating frequencies of various Spn and NTHi antigen-specific memory T-helper cell subsets were compared between non-otitis prone and otitis prone children by stimulating their PBMCs with specific antigens. For that, the percentages of T-helper memory cells producing IFN-γ, IL-4, IL-2 or IL-17 were calculated by gating on activated CD69$^+$ T-cells (FIG. 15). No difference was found in the naive and memory CD4$^+$ T-cell counts among both the cohorts (Table 3). Antigen specific responses were normalized with the control PBMCs left unstimulated or stimulated with a non-specific antigen (Keyhole limpet hemocyanin).

TABLE 3

Circulating CD4$^+$ T-cell counts per million PBMCs in otitis prone and non-otitis prone children

| | Cell counts per microliter (μl) of blood (Mean ± SD) | | |
|---|---|---|---|
| Cell type | Otitis prone (n = 19) | Non-otitis prone (n = 20) | P values |
| CD3$^+$CD4$^+$ T-cells | 2306 ± 452 | 2099 ± 380 | 0.17 |
| CD3$^+$CD4$^+$CD45RA$^+$ (naive CD4$^+$ T-cells) | 1322 ± 640 | 1240 ± 590 | 0.10 |
| CD3$^+$CD4$^+$CD45RA$^−$ (memory CD4$^+$ T-cells) | 455 ± 180 | 537 ± 198 | 0.18 |

FIG. 16A demonstrates frequencies of the various subsets of T-helper memory cells to all the Spn antigens used for stimulation in non-otitis prone children (n=15) following AOM (n=6) or NP colonization (n=9) with Spn. In sharp contrast, otitis prone children (n=13) had a marked dysfunction of circulating Spn specific T-helper memory cells after AOM (n=10) and NP colonization (n=3). In particular, there was a complete lack of T-helper memory cells producing IFN-γ against LytB, PhtE and PlyD1 whereas significantly lower levels of IFN-γ were produced in response to PhtD, PcpA and PspA (P<0.02). A significant decrease in IL-4 producing T-helper memory cells was observed against PhtD and LytB (P<0.02) in the otitis prone children. IL-2 responses to PhtD (P<0.05), PcpA (P<0.005), PhtE (P<0.05), PlyD1 (P<0.005) and PspA (0.02) were significantly lower in otitis prone children and a significant reduction in IL-17a producing cells were found in otitis prone children in response to PhtD, PcpA and PhtE (P<0.05).

FIGS. 3A-D show the results of a separate series of experiments involving 6-non-otitis prone children (all NP colonized with NTHi) and 6-otitis prone children either NP colonized with NTHi (n=2) or having an AOM episode caused by NTHi (n=4). PBMCs were stimulated with NTHi protein antigens P6, OPM26 and protein D. Otitis prone children were devoid of IFN-γ producing T-helper memory cells against all 3 NTHi antigens used for stimulations. Otitis prone children lacked an IL-4 response to P6 antigen (p<0.05) but no significant differences were observed in the IL-4 response to OMP26 and protein D compared to non-otitis prone children (p=0.6). No T-helper memory cells were found in otitis prone children producing IL-2 upon stimulation with protein D, and the frequencies of cells responding to OMP26 and P6 were significantly reduced (p<0.05).

Neither otitis prone nor non-otitis prone children showed IL-17a response upon stimulation with P6. Otitis prone children were devoid of OMP26 specific memory Th-cells producing IL-17a, a significant difference from non-otitis prone children (p=0.05). The difference in the frequencies of IL-17a producing memory T-helper cells to protein D was not significant (P=0.7).

iii. Otitis Prone Children are not Deficient in Total Functional Memory T-Cells

Impaired T-helper memory cell responses to the Spn and NTHi antigens among otitis prone children were due to intrinsic T-cell defects among otitis prone children. For that, PBMC were stimulated with SEB (as described in methods), an antigen that stimulates a T-cell response independent of antigen presenting cell involvement [Llewelyn et al., Int. Immunol. 2006; 18(10):1433-41]. Upon stimulation with SEB, percentage of CD45RA$^{Low}$ CD4$^+$ T-cells producing IFN-γ, IL-4, IL-2 or IL-17a was found to be the same for otitis prone and non-otitis prone children (P>0.5; FIG. 16B).

iv. Antibody Responses to Spn and NTHi Protein Antigens are Reduced in Otitis Prone Children.

Antigen specific IgG titers were evaluated in the serum of non-otitis prone and otitis prone children. Serum IgG levels to the similar Spn and NTHi antigens in the respective groups are shown in FIG. 17. As expected, with the increased T-helper memory cell frequencies, IgG titers to PhtD, LytB, PhtE, PlyD1 were significantly higher in the non-otitis prone group compared to otitis prone (P<0.05; 0.0005; 0.0005; 0.005 respectively), whereas PcpA levels were not significantly different between the groups (FIG. 17A). Among NTHi antigens significantly higher IgG levels were observed to Protein D in non-otitis prone children compared to the otitis prone children (p<0.05), whereas no significant differences in the levels of IgG antibody to P6 and OMP26 were measured between the groups (FIG. 17B).

4. Discussion

Children who experience repeated AOM suffer the greatest morbidity from this infection, sometimes resulting in permanent hearing loss [Vergison et al., Lancet Infect. Dis. 2010; 10(3):195-203; Morris and Leach, Pediatr. Clin. North Am.

2009; 56(6):1383-99]. As compared to non-otitis prone children, previous reports have described otitis prone children to produce lower amounts of Spn and NTHi-specific antibodies and/or not to produce functional bactericidal antibodies [Faden, Eur. J. Pediatr. 2001; 160(7):407-13; Pichichero et al., Vaccine 2010; 28:7184-7192; Murphy and Yi, Ann. N.Y. Acad. Sci. 1997; 830:353-60]. These findings indicated that decreased concentration of circulating antibodies to the otopathogen antigens explained the otitis prone condition. A more precise immunological explanation for the observed lower antibody levels in the otitis prone children to was sought to facilitate further research to circumvent the dysfunction. It was postulated that a reduced antibody response observed in the otitis prone children can be the result of impaired $CD4^+$ T-helper cell responses to the pathogen. Hence, generation of antigen specific memory $CD4^+$ T helper cell subsets (Th-1, Th-2 and Th-17) were compared between non-otitis prone and otitis prone populations of children. This becomes important since $CD4^+$ T helper cells have been shown to mediate help in fighting infections caused by Spn and NTHi [Malley et al., Infect. Immun 2006; 74(4):2187-95; King et al., Am. J. Respir. Crit Care Med. 2003; 167(4):587-92; de Bree et al., J. Infect. Dis. 2007; 195(11):1718-25]. However, there is no report demonstrating a protective role of pathogen-specific $CD4^+$ T helper-cells in AOM in children which is caused by these respiratory pathogens.

A clear reduction in the functional memory $CD4^+$ T cell frequencies producing various cytokines among children that are prone to AOM infections was found (FIGS. 16A and 3A-C). Otitis prone children develop short-lived antibody responses since antibodies were detectable among these children after AOM and NP colonization with otopathogens (FIG. 17A-B). However, in the absence of adequate pathogen-specific memory $CD4^+$ T cell frequencies and after the antibody levels wane the child quickly becomes susceptible to additional AOM infections. Recent work on follicular T helper cells (Tfh) has established their significance in generating B-cell mediated antibody responses. Hence, it was expected that otitis prone children can have reduced Tfh in their circulation. Surprisingly, staining of $CD4^+$ T cells for CXCR5 expression did not identify a difference in the Tfh population in the circulation in otitis prone or non-otitis prone children (data not shown). At first, only a low percentage of CXCR5 expressing $CD4^+$ Tfh-cells can be detected in the peripheral blood as demonstrated in adults [Fazilleau et al., Immunity. 2009; 30(3):324-35]. Secondly, preliminary data indicate that children of this age group lack overall CXCR5 expressing $CD4^+$ T cells in their circulation. This makes it difficult to compare Tfh populations in the PBMCs of otitis prone and non-otitis prone children (unpublished data). Furthermore, as a result of SEB stimulation, similar percentages of functional memory $CD4^+$ T cells were observed among both the cohorts and that rules out an intrinsic defect in the $CD4^+$ T cells of otitis prone children (FIG. 1C).

Previous work has demonstrated role of Spn and NTHi antigens in $CD4^+$ T cell proliferative responses (for 5-7 days) among children and adults [Mureithi et al., J. Infect. Dis. 2009; 200(5):783-93; Zhang et al., J. Infect. Dis. 2007; 195 (8):1194-202]. A prior study evaluated $CD4^+$ T cell proliferation in the cells collected from the adenoids and tonsils of otitis prone children and found no proliferation in response to NTHi protein P6 [Kodama et al., Acta Otolaryngol. 1999; 119(3):377-83]. Studies of this nature are imperative to evaluate antigen specific T cell proliferation but fail to inform about occurrence of antigen specific memory $CD4^+$ T-cells. These data are the first report that demonstrates increased frequencies of Spn and NTHi-specific IL-17a producing memory Th-cells in the circulation of non-otitis prone children, as compared to otitis prone children (FIG. 1). Although not directly demonstrated, the IL-17a producing memory Th-cells can contribute to protection against the otitis prone condition caused by Spn or NTHi by an antibody-independent mechanism as demonstrated in a mouse model [Malley et al., Infect. Immun 2006; 74(4):2187-95].

The cellular phenotyping of middle ear fluid during AOM as well as adenoids in similar individuals has indicated a large migration of $CD45RO^{High}/CD45RA^{Low}$ memory $CD4^+$ T-cells as determined by loss of homing receptors L-selectin [Mattila et al., Int. Immunol. 2000; 12(9):1235-43; Skotnicka et al., Otol. Neurotol. 2005; 26(4):567-71]. Local secondary lymphoid organs such as adenoids are the primary sites for T-cell priming during upper respiratory tract bacterial infections and nasopharyngeal colonization. Once, an antigen loaded APC migrates to local lymphoid organs (adenoids), the differentiation of lymphocytes (c.f. $CD4^+$ T-cells) takes place. After entering the blood circulation the $CD4^+$ T-cells may eventually migrate to the middle ear mucosa (in case of AOM) and/or the upper respiratory tract (during NP colonization) [de Bree et al., J. Infect. Dis. 2007; 195(11):1718-25; Mattila et al., Int. Immunol. 2000; 12(9):1235-43]. Unlike mice, it is practically impossible to track antigen-specific $CD4^+$ T-cells in human subjects. Nevertheless, evaluation of MEF for the cellular phenotypes indicates that T-helper memory cells may play a key role in the elimination of AOM pathogens at the middle ear mucosa. Hence otopathogen-specific T cell memory, if generated, can be helpful in the prevention of recurrent AOM.

A decreased antibody response has been reported previously after immunization with *rubella* vaccine in otitis prone children [Prellner et al., Ann. Otol. Rhinol Laryngol. 1990; 99(8):628-32]. A similar dysfunction in T cell responses to vaccination have been observed among bone marrow or stem cell recipients [Avetisyan et al., Bone Marrow Transplant. 2005; 36(5):411-5; Avigan et al., Biol. Blood Marrow Transplant. 2001; 7(3):171-83]. Also earlier studies have suggested a genetic polymorphism in the expression of various immunoresponsive genes TNFa, IL-6, IL-10 among otitis-prone children [Emonts et al., Pediatrics 2007; 120(4):814-23; Revai et al., Clin. Infect. Dis. 2009; 49(2):257-61]. Faulty function of APCs has been described to be responsible for immature T cell responses among infants and young children [Zaghouani et al., Trends Immunol. 2009; 30(12):585-91]. Furthermore, dendritic cells in infants has been shown to pose restriction in generating vaccine-specific T cell memory [Upham et al., Infect. Immun 2006; 74(2):1106-12]. Collectively, based on the presented data as well as prior reports it is possible that APCs in otitis prone children are unable to prime naive T cells for memory generation. Whether otitis-prone children possess an immature subset of APC and therefore are unable to process and present antigens to the $CD4^+$ T-cells for effector/memory generation are now an area of investigation.

Generating efficacious immunity against NTHi requires CD4 T cells directed against the otopathogen. peripheral blood mononuclear cells (PBMCs) were used to discover that OP children have limited pathogen-(NTHi) specific memory CD4 T cells as compared to NOP children (FIG. 3). These findings point the way to a need for specific protein structures and adjuvants to enhance the immune response in OP children.

This study aimed at determining the divergent generation and function of T-helper effector/memory as a mechanism for failure to prevent AOM in OP children. A multi-parameter ICCS flow cytometric method was developed. Using P6 and 2 other NTHi and 6 Spn protein antigens, NTHi and Spn-specific functional CD4+ T-helper effector/memory cell subsets were analyzed from the peripheral blood, adenoids and tonsils of OP and NOP children. These data show a consistent lack or reduction of NTHi and Spn antigen specific memory (CD45RA$^{Low}$) CD4 T cells among OP children in the blood. This indicated that the lack of functional memory CD4 T-cell responses in the OP child makes them susceptible to repeated AOMs until a more developed immunologic maturation is achieved (Sharma et al JID 2011 in press). The exception is P6 where functional antibody responses are generated from natural infection in OP children infected with NTHi [Khan et al., FEMS Immunol Med Microbiol 2012 DOI:10.1111/j.1574-695X.2012.00967.x].

An absence/lower proliferation and cytokine production was found to many antigens but less so to NTHi P6 in the OP children as compared to NOP children. In the B cells, a lower/deficiency of B cell memory generation was found in OP children except less so to P6 [Sharma et al., J Infect Dis. (2012) 205(8):1225-1229].

C. Example 3

AOM and Inflammation

Figure 4:
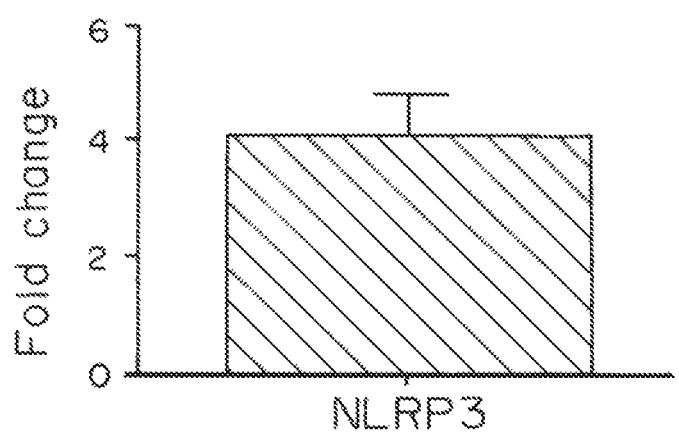
FIG. 4 is a graph showing inflammasome activation is higher in OP than NOP children. Expression of NLRP3 was determined in nasal cell pellets of OP (n=3) and NOP (n=5) children (<2 years) with AOM. Relative fold change of OP over NOP shown. +/−SEM from children 915 months old. 18S used as a calibrator.
Figure 5:
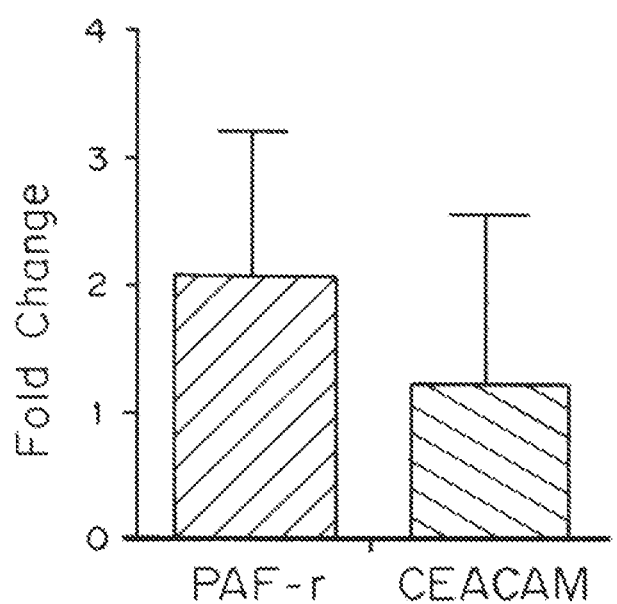
FIG. 5 is a graph showing higher bacterial receptor upregulation in the nasal mucosa of OP children. The Spn expression pattern of nasal cell pellets was assessed by RT-PCR. Data shown represents average fold change of expression of OP over NOP children+/−SD. (n=5 each group with average age of 9 months)

The innate response is comprised of both innate gene responses from epithelium and innate immune (NK, neutrophil, macrophage) responses that release pro-inflammatory cytokines that affect epithelial inflammation. There is a 93% correlation in children experiencing an active AOM infection and a concurrent respiratory viral infection. Viral infections drive significant changes to the airway epithelium manifested by morphological changes and inflammation induced by inflammasomes or cytokines, and cell death. These events set the stage for AOM. In addition, respiratory bacteria also cause inflammation and epithelial cell death. Currently, the role that NHTi plays in driving inflammasome activation of epithelium is not known but colonization is associated with increases in epithelial inflammation. These data show a trend in higher NLRP3 activation after NTHi infection in OP children (FIG. 4). The alterations to nasal epithelium to permit the transition from colonization to pathogenic infection have not been determined although viral infections of nasal epithelial cell lines cause up-regulation of epithelial cell receptors for bacterial adherence to occur more effectively. FIG. 5 shows PAFr, a bacterial adherence factor appears more up-regulated (trend) in OP than NOP children during AOM infection.

Figure 6:
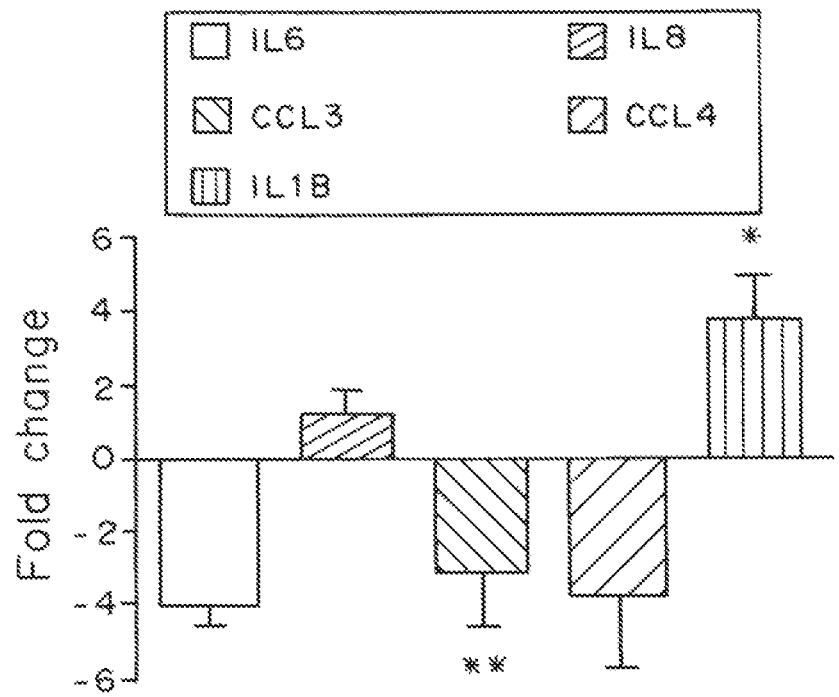
FIG. 6 is a graph showing that proinflammatory cytokine expression diverges in NOP and OP children. Expression of proinflammatory genes were determined in nasal cell pellets of OP (n=4) and NOP (n=5) children (<2 years) with AOM. Relative fold change of OP over NOP shown. +/−SEM 6-15 months old in each group. *p<0.05 for $\Delta C_T$ values **p=0.09. 18S used as a calibrator.

The exact mechanisms facilitating the transition from otopathogen colonization to AOM has not been fully determined although there is an association between the levels or polymorphisms of innate cytokine expression and AOM in OP children. The onset of AOM in OP and NOP children generally occurs within the first 6 days of a viral infection when there is significant innate cellular recruitment to the respiratory mucosa which is associated with strong pro-inflammatory cytokine release. The levels of these pro-inflammatory cytokines to viral infections could dramatically favor bacterial colonization by stressing nasal epithelium and driving progression to AOM. OP children can have divergent proinflammatory cytokine responses (FIG. 6) which may be due to either a difference in innate cytokine responses or by a lack of T-cell memory (FIG. 3) which would fail to rapidly reduce antigen burdens as would occur in NOP children and drive continued heightened epithelial stress.

D. Example 4

Toll-Like Receptors and AOM

Figure 7:
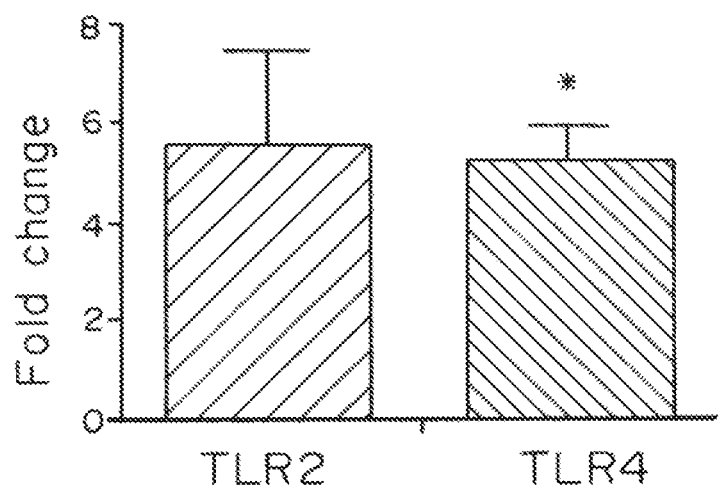
FIG. 7 is a graph showing divergent TLR expression in OP and NOP children. Expression of TLR2 and TLR4 were determined in the nasal wash of OP (n=4) and NOP (n=5) children (<2 years) during AOM. Relative fold change of OP over NOP shown. +/−SEM. *p=0.01 for $\Delta C_T$ values. 18S used as a calibrator.

Toll-like receptor (TLR) expression plays a role in initiating the activation of the immune response to bacterial infection. Previous studies have determined a correlation between disruption of TLR4 or MyD88 and AOM (Hernandez et al., (2008). J Infect Dis. 198 (12):1862-9). Differences in TLR expression have also been demonstrated to be a component of immunological maturation and adequate immune stimulation during infection. Therefore, children prone to AOM can have recurrent AOM due to intrinsic TLR expression deficiency. Defective innate immunity is associated with poor sepsis outcome in neonates but is reversible with TLR agonists implying that the capacity to respond to TLR stimulation may be a critical factor in OP children with immune competency that potentially mirrors neonates. FIG. 7 shows different TLR expression levels in cells recruited to the nasal mucosa during AOM in OP and NOP children. Surprisingly, it was determined that OP children have higher expression levels of TLR2 and TLR4 despite evidence that APC function may be lower which could imply downstream defects in signaling.

These data identify targets to be used as therapeutics with P6 to further enhance immunogenicity, and to overcome differences in immune responses of OP children in the levels of pro-inflammatory cytokines released during the innate immune response that drives AOM. The targets are downregulation of NLRP3, PAFr and IL1B and for upregulation are IL6, CCL3, CCL4 and downstream signaling of TLR2 and TLR4.

OP children with AOM infection have different levels of inflammatory gene expression in response to viral and bacterial co-infection than NOP children, but less so with P6 (FIG. 8). Inflammatory conditions can disrupt epithelial membrane integrity, lead to epithelial cell receptor alterations, and promote epithelial cell death, events that are associated with enhanced NTHi binding to epithelial mucosa and thereby facilitate an increase in the otopathogen inoculum. However, lower inflammatory conditions can also have an impact on the activation of the adaptive immune response that is more closely associated with resolution of infections and appears to deviate in OP and NOP children based on our data, but less so with P6.

E. Example 5

Antibody Response to *Haemophilus influenzae* Outer Membrane Protein D, P6, and OMP 26 after Nasopharyngeal Colonization and Acute Otitis Media in Children 1. Introduction Nontypeable *Haemophilus influenzae* (NTHi) is currently the most frequent cause of episodic and recurrent acute otitis media (AOM) in children in the United States [Casey and Pichichero, Pediatr Infect Dis J 2004; 23(9):824-8; Pichichero and Casey, Pediatr InfectDis J 2007; 26(10):512-6; Casey et al., Pediatr Infect Dis J 2010; 29 (April (4)):304.9]. AOM and all respiratory bacterial infections begin pathogenesis with colonization of the nasopharynx (NP). However, carriage of NTHi is mostly asymptomatic; only when the condition of the host is altered, NTHi may invade the middle ear, causing AOM.

A vaccine against NTHi presents a different set of challenges compared with Hib vaccination because rather than a single dominant capsular antigen, NTHi strains express multiple outer membrane proteins (OMPs) [Barenkamp et al., Infect Immun 1982; 36:535-40; Loeb and Smith, Infect Immun 1980; 30:709-17; Murphy et al., J Infect Dis 1983; 147:838-46; St. Geme, Vaccine 2001; 19(1):541-50] Several of the OMPs of NTHi have been eliminated as vaccine candidates due to surface epitope heterogeneity, variable expression or other characteristics [St. Geme, Vaccine 2001; 19(1): 541-50; Kyd and Cripps, J Biotechnol 1999; 73:103-8]. Desirable vaccine candidate antigens for NTHi should be conserved among strains and immunogenic in children and adults. At this time one OMP of NTHi, protein D, has been incorporated into a commercialized vaccine product as a carrier of pneumococcal polysaccharide antigens. Administration of that conjugate vaccine resulted in a 35% reduction in AOM caused by NTHi [Prymula et al., Lancet 2006; 367:740-8]. Further proof of the efficacy of protein D as a vaccine ingredient for prevention of NTHi mucosal infections is needed and the study of other NTHi antigens is underway in many laboratories, anticipating the need for a multi-component vaccine to optimize protection at rates higher than protein D alone.

Two additional NTHi OMPs that are leading vaccine candidates are protein 6 (P6) and protein OMP26, since they possess the desirable features noted above [St. Geme, Vaccine 2001; 19(1):541-50; Kyd and Cripps, J Biotechnol 1999; 73:103-8]. For NTHi vaccine development it is important to know whether antibodies develop after natural NTHi exposure such as after asymptomatic NP colonization and after AOM. In the present study it was hypothesized that NTHi NP colonization and AOM would represent immunizing events for potential OMP vaccine ingredients. This is the first study to prospectively compare the development of natural antibodies to 3 NTHi outer membrane proteins D, P6 and OMP26 simultaneously in a cohort of children 6-30 months of age during NP colonization and AOM. The comparisons of interest we report here include: 1. Changes in the levels of protein D, P6 and OMP26-specific IgG antibodies in children as they increased from 6 to 30 months of age; 2. Changes in antibody levels following detected colonization of the NP with NTHi; 3. Differences in antibody levels in convalescence from NP colonization versus AOM; 4. Variations in individual antibody repertoire and responses in the study cohort following AOM; and 5. Differences in contribution of antibodies to protein D, P6 and OMP26 to bactericidal activity.

2. Methods i. i. General Design

This report includes data for the 3 year time span June, 2006 to December, 2009 from children enrolled in a 5 year prospective study supported by the National Institutes of Deafness and Communication Disorders. Healthy children without previous episodes of AOM were enrolled from a middle class, suburban socio-demographic pediatric practice in Rochester, N.Y. (Legacy Pediatrics). Healthy children had serum, NP and oropharyngeal (OP) cultures and NP wash samples obtained seven times, every 3.6 months, between 6 and 30 months of age (at age 6, 9, 12, 15, 18, 24, and 30 months). In addition, if a child developed symptoms compatible with AOM, they were examined by validated otoscopist pediatricians with pneumatic otoscopy and if middle ear infection was suspected a tympanocentesis was performed to confirm the diagnosis. At the time of the acute AOM diagnosis and three weeks later acute and convalescent serum, NP and OP cultures and NP wash samples were obtained. The study was approved by the University of Rochester and Rochester General Hospital Research Subjects Review Board and written informed consent was obtained for participation and all procedures.

Three NTHi OMPs were elected to be studied. Protein D is a highly conserved antigen among NTHi strains [Forsgren et al., Clin Infect Dis 2008; 46:726-31]. It is a 43 kDa surface exposed lipoprotein that has glycerophosphodiesterase. P6 has been described as a highly conserved OMP among NTHi strains Immunization with P6 provides protection against AOM in the chinchilla model [DeMaria et al., Infect Immun 1996; 64:5187-92]. OMP26 is a highly conserved protein of NTHi that is associated with protection against NTHi infections after parenteral and mucosal immunization in the chinchilla and rat models that induced high levels of antibody [Kyd and Cripps, Infect Immun 1998; 66:2272-8; Kyd et al., Infect Immun 2003; 71:4691-9].

ii. Definition of AOM

AOM was diagnosed by pneumatic otoscopy by validated otoscopists, when children with acute onset of otalgia had tympanic membranes (TMs) that were: (1) bulging or full; and (2) a cloudy or purulent effusion was observed, or the TM was completely opacified; and (3) TM mobility was reduced or absent.

iii. Tympanocentesis

MEF for culture was obtained by puncture of the inferior portion of an intact TM with a 20-gauge spinal needle attached to a 3-mL syringe using a hand-held operating otoscope. If a small sample of MEF was obtained on aspiration, 0.5 mL of trypticase soy broth was aspirated through the spinal needle and then aliquoted and inoculated onto agar plates and into broth, as described below.

iv. Sample Collection

At each sampling visit a cotton-tipped wire swab was inserted into both nares and a culture of the posterior nasopharynx was obtained; an OP culture was obtained by rubbing both tonsils and the posterior pharynx. Then lmL of sterile phosphate buffered saline was instilled and aspirated from both nares as a third sample for culture. Serum was obtained by venipuncture after application of ELMA cream for local numbing of the area.

v. Microbiology

MEF, NP, and OP samples were inoculated into trypticase soy broth, trypticase soy agar with 5% sheep blood plates, and chocolate agar plates. All samples were incubated at 37° C. with 5% carbon dioxide. Bacteria were isolated according to the CLSI standard culture procedures. An isolate was further identified as NTHi on a similar basis as described by Murphy et al. [Murphy et al., J Infect Dis 2007; 195:81-9] to include not only colony morphology, porphyrin reactivity, and growth requirement for hemin and nicotinamide adenine dinucleotide and *Haemophilus* ID Quad plates, but also by ompP6 sequencing to distinguish NTHi from *H. haemolyticus* [Murphy et al., J Infect Dis 2007; 195:81-9].

vi. Detection of OMP-Specific Antibodies by ELISA

Protein D, P6 and OMP26-specific antibody titers were determined by ELISA using purified recombinant protein D (provided as a gift from GlaxoSmithKline Biologicals, Rixensart Belgium), lipidated P6 (provided as a gift by Dr. Tim-Murphy, University of Buffalo) and OMP26 (provided as a gift by Jennelle Kyd, University of Canberra, Australia). 96-well Nunc-Immulon 4 plates were coated with 0.25-0.5 µg/mL of individual OMP antigens 100 µL/well) in coating buffer (bicarbonate, [pH 9.4]) and incubated overnight at 4° C. After washing the plates were blocked with 3% skim milk at 37° C. for 1 h (200 µL per well). After five washes, 100 µL of serum at a starting dilution of 1:100 (in PBS.3% skim milk) was added to the wells and diluted serially 2 fold. The mixture was incubated at room temperature for 1 h followed by the addition of affinity purified goat anti-human IgG, IgM or IgA antibody conjugated to hoarseradish-peroxidase (Bethyl Laboratories, Inc., Montgomery, Tex.) as a secondary antibody. The reaction products were developed with TMB Microwell Peroxidase Substrate System (KPL, Gaithersburg, Md.), stopped by the addition of 1.0M phosphoric acid and read by an automated ELISA reader using a 450-nm filter.

To provide quantitative results on antibody concentrations, the level of the specific antibody present in the unknown sample was determined by comparison to an internal reference serum (pool of human serum with high anti-OMP titers). The levels of IgG, IgM and IgA in the reference serum were quantitatively measured by using a human IgG/IgA/IgM ELISA quantitation kit (Bethyl laboratories).

A four-parameter logistic-log function was used to form the reference and sample curves. This ELISA was fully validated according to ICH Guidance. The assay lower limit of detection for protein D was 3.5 ng/mL for IgG, 4.5 ng/mL for IgM, and 8 ng/mL for IgA; for P6 it was at 1 ng/mL for IgG, 3 ng/mL for IgM, and 3 ng/mL for IgA; and for OMP26 it was at 4 ng/mL for IgG, 3 ng/mL for IgM, and 10.5 ng/mL for IgA. The inter-assay coefficient of variation was 20% for all antigens and secondary antibody combinations.

vii. Bactericidal Assay

Eleven sera were randomly selected from those with the greatest volumes to measure bactericidal activity pre and post absorption with protein D, P6 and OMP26. The sera were heatinactivated at 56° C. for 30 min to eliminate human complement. Each serum was assayed against the bacterial strain isolated from middle ear space of that child. Homologous NTHi strains were cultivated, harvested, and diluted to a concentration of ~$10^5$ CFU/mL. Twelve serial twofold dilutions of the serum to be tested (starting at 1:2) were mixed with precolostral calf serum complement and 20 μL of bacteria. After 60 min of incubation, the number of surviving bacteria was determined by plating 5 μL onto chocolate agar and counting the colonies. The bactericidal titer of the serum was defined as the inverse of the highest dilution that led to ≥50% bacterial killing and was compared to that of negative control serum. Appropriate controls were included in all experiments. To examine the contribution of protein D, P6 and OMP26 antibodies to serum bactericidal activity observed, we removed all protein D, P6 or OMP26 antibodies from available sera using polystyrene beads. For the absorption procedure, polystyrene beads were washed extensively with borate buffer (pH 8.5) and resuspended in 1 mL of Borate buffer. Freshly prepared recombinant protein D, P6 and OMP26 antigens were incubated with these beads overnight at room temperature. The beads were washed extensively, incubated in BSA/Borate buffer for 30 min at room temperature, then pelleted and incubated with 200 μL of patient sera for 2 h at room temperature. The beads were centrifuged (200×g) and the supernatant was collected.

The efficacy of absorption was monitored by using ELISA as described above. The reciprocal bactericidal titers were compared with unabsorbed sera to determine the bactericidal activity mediated by each of the specific antibodies. An experiment was performed with cross adsorption of other antibodies and found that adsorption was quite specific.

viii. Multi-Locus Sequence Typing (MLST)

Bacterial genomic DNA was extracted from pure cultures of NTHi isolated from NP, OP or MEF samples (If children have AOM). The internal fragments of seven housekeeping genes of NTHi were amplified by PCR, using PCR Master Mix (Promega, 50 units/mL of Taq DNA Polymerase, 400 μM dNTP, 3 mM $MgCl_2$) using primers described previously [Medeiros et al., Rev Inst Med Trop Sao Paulo 1998; 40:7-9]. PCR conditions were as follows: initial denaturation at 95° C. for 4 min, followed by 30 cycles of 95° C. for 30 s, 50-55° C. annealing for 30 s and 72° C. extension for 30 s.

Sizes of PCR products were checked by running 1.5% agarose gel electrophoresis stained with ethidium bromide. The size of PCR products was 50-100 bps larger than the fragments for typing. The PCR products were purified using the Exo-sap kit (USB Company) and identified by DNA sequencing. Sequencing analyses were performed on an ABI Prism 3730xlDNA analyzers with the same primers used for PCR product amplification.

ix. Statistics

Two sample comparisons were performed using either paired t-test, two-sample t-test (using a log transformation where appropriate), the Mann-Whitney rank sum test or Fisher's exact test. Testing for increasing antibody level with age (FIG. 10) was complicated by inconsistently represented time points, and by data dependence induced by repeated sampling by subject. A modification of Kendall's tau statistic was used to measure within-subject concordance of level with age. Any pair of within subject antibody level measurements which increases with age was concordant, and was discordant otherwise (neither applies in the case of ties). In the calculation Nc and Nd were the number of concordant and discordant within-subject pairs and G=(Nc−Nd)/(Nc+Nd). The statistic G was calibrated as a correlation, with −1 and 1 representing perfect negative and positive associations, respectively, between age and antibody level measurement. The quantity S=Nc/(Nc+Nd) represented the proportion of increasing pairs. If there was no concordance S=½ was expected, on average. To assess significance, a bootstrap procedure was performed by resampling subjects with replacement. This procedure permitted within-subject dependence. The bootstrap sample was then used to estimate 95% confidence intervals for S, and p-values against the null hypothesis S=½.

For all testing, p<0.05 was considered significant.

3. Results i. NP Colonization and AOM Events

Figure 9:
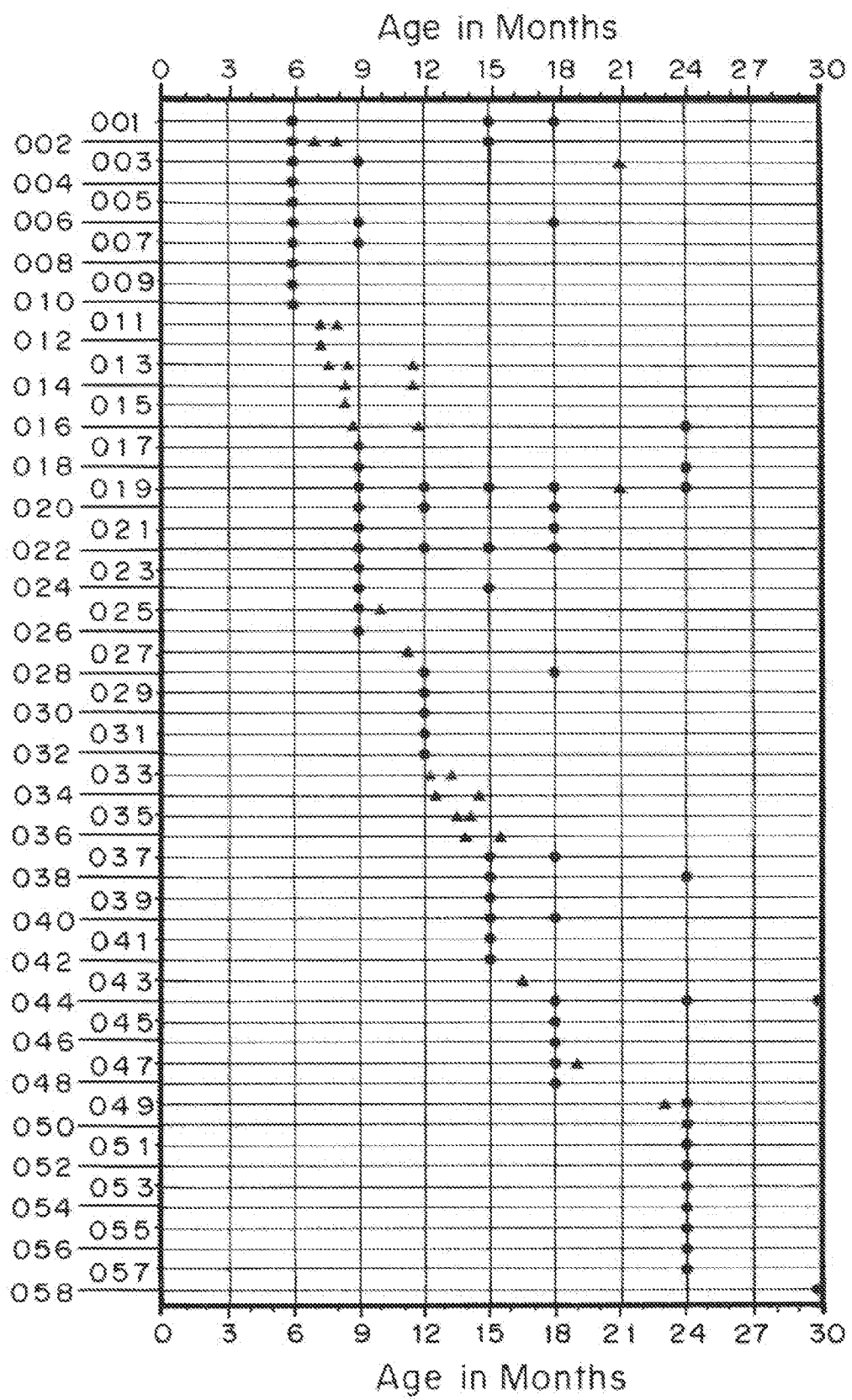
FIG. 9 shows nasopharyngeal and/or oropharyngeal colonization episodes represented by a closed circle at visits 1-7 at 6, 9, 12, 15, 18, 24, and 30 months of age. AOM episodes are represented by a closed triangle.

During the 3 years of enrollment a total of 130 children were recruited into the study. There were 631 visits with 72 NTHi OP/NP colonization episodes documented in 47 (28%) children who were culture-positive for NTHi at one or more of the seven sampling visits (FIG. 9). Among the 47 NP colonized children, 31 (66%) of the children were NTHi culture-positive at one sampling visit, 10 (21%) at two visits, 4 (9%) at three visits and 2 (4%) at four or more visits. Eighty three (64%) did not have NTHi detected by culture in the NP or OP at any of the 7 visits. Thirty-seven (79%) children experienced colonization that was detected by culture and cleared by the next sampling 3-6 months later. NP colonization was detected at the first sampling at 6 months of age in 10 (21%) children and at various times thereafter for the remainder of the subjects. Nine of the 47 colonized children (19%) experienced prolonged detected colonization of 6 months or longer with the same NTHi strain based on multi-locus sequence typing (subjects 1, 6, 7, 19, 20, 22, 37, 40, and 44; MLST data not shown). Because the study design called for NP/OP sampling at 7 specific times separated by 3-6 months, some NTHi colonization events were not detected by culture but most likely occurred as reflected in significant rises in specific antibody to one or more of the NTHi antigens studied. There were 28 NTHi AOM episodes in 18 children. Nine (50%) of the 18 AOM children experienced one AOM due to NTHI, 8 (44%) children experienced 2 AOM events due to NTHi and 1 (6%) experienced 3 NTHi AOM events (FIG. 9).

ii. Natural Acquisition of Serum Antibody to Protein D, P6 and OMP 26 Over Time

Figure 10A:
FIGS. 10A, 10B and 10C are graphs of serum IgG antibody levels to NTHi outer membrane proteins D (A), P6 (B) and OMP26 (C) in healthy children increases with age. Boxplots of the geometric mean concentration (ng/mL) displayed as a bar, 25‰ and 75‰ of the data displayed as the lower and upper limit of the box and the 95% confidence interval displayed as a short horizontal dash of antibody in sera of children taken during 7 sampling visits at 6, 9, 12, 15, 18, 24 and 30 months of age. The number of sera included at each time point was 100, 88, 60, 59, 52, 43, and 8. Boxplots of the geometric mean concentration (ng/ml) displayed as a bar, 25% ile and 75% ile of the data displayed as the lower and upper limit of the box and the 95% confidence interval displayed as short horizontal dash of antibody in sera of children taken during 7 sampling visits at 6, 9, 12, 15, 18, 24 and 30 months of age. The number of sera included at each time point was 100, 88, 60, 59, 52, 43, and 8.
Figure 10B:
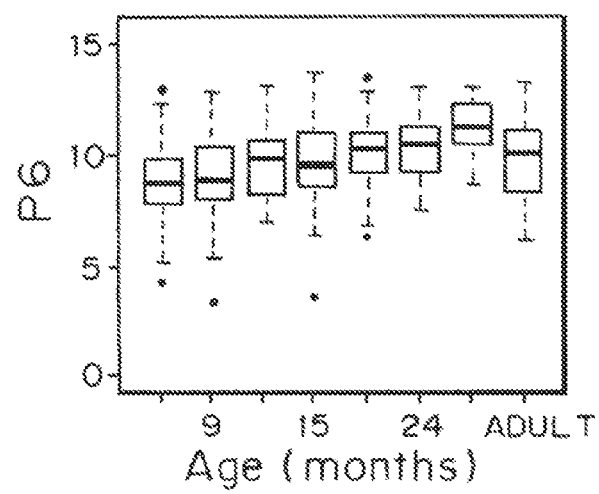
Figure 10C:
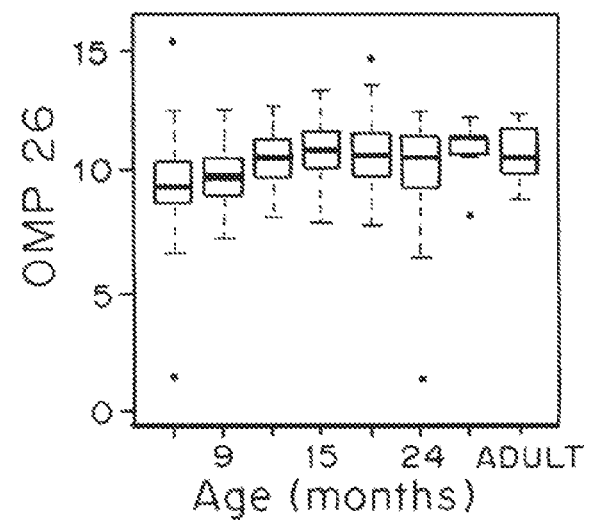
Figure 11A:
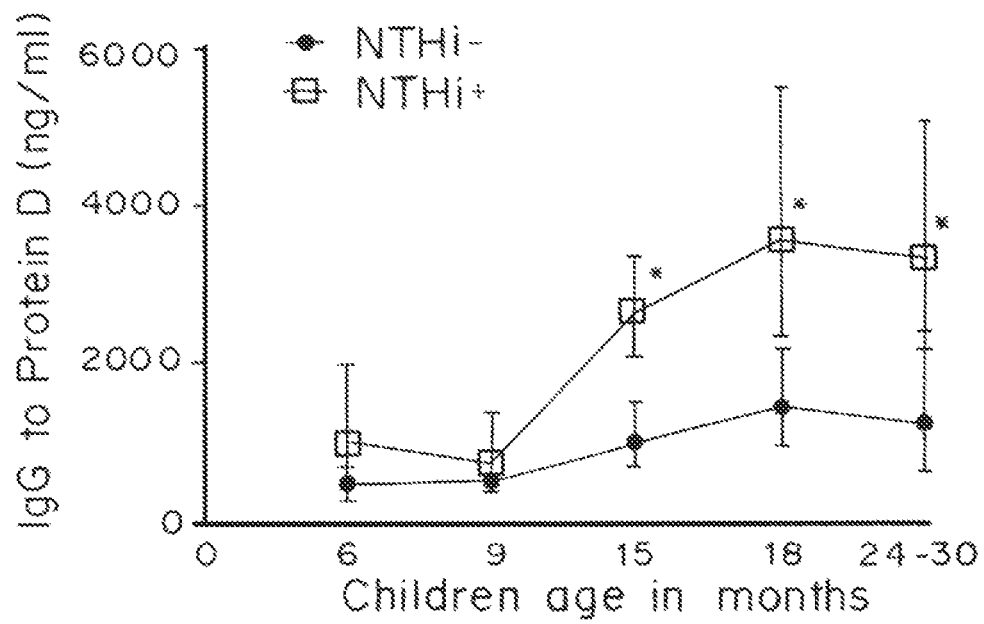
FIGS. 11A, 11B and 11C show graphs comparing serum IgG antibody levels to NTHi outer membrane proteins protein D (A), P6 (B) and OMP 26 (C) in NP colonized (□NTHi+) and non-colonized (•NTHi−) healthy children from 6 months to 24 months of age. * indicates that the differences in colonized vs. non-colonized children were significant for protein D at visit 15, 18 and 24-30 months with p value is equal to 0.04, 0.01 and 0.02 respectively and for P6 at 6, 9 and 15 months with p value 0.0003, 0.02 and 0.003 respectively.
Figure 11B:
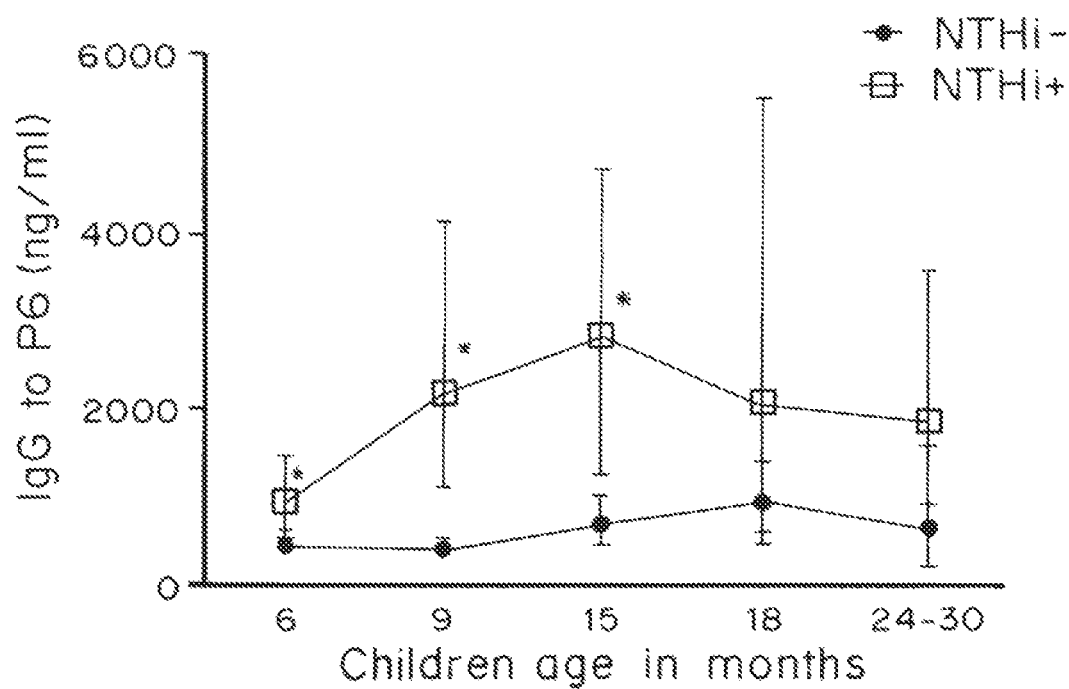
Figure 11C:
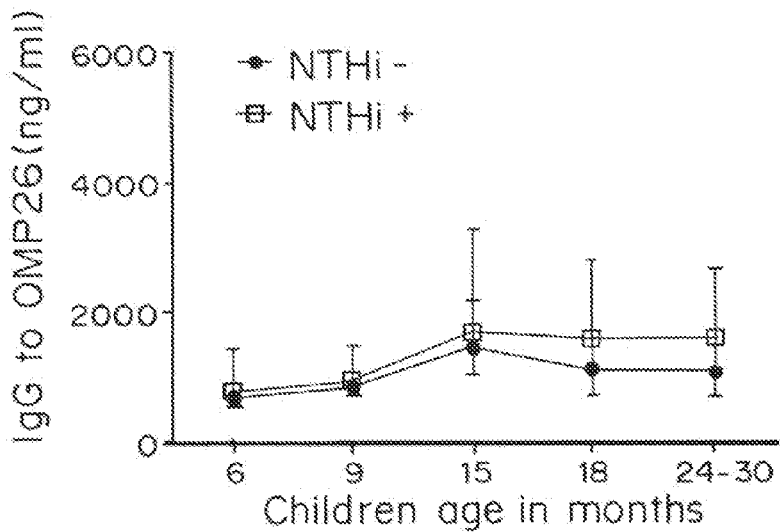
Figure 12:
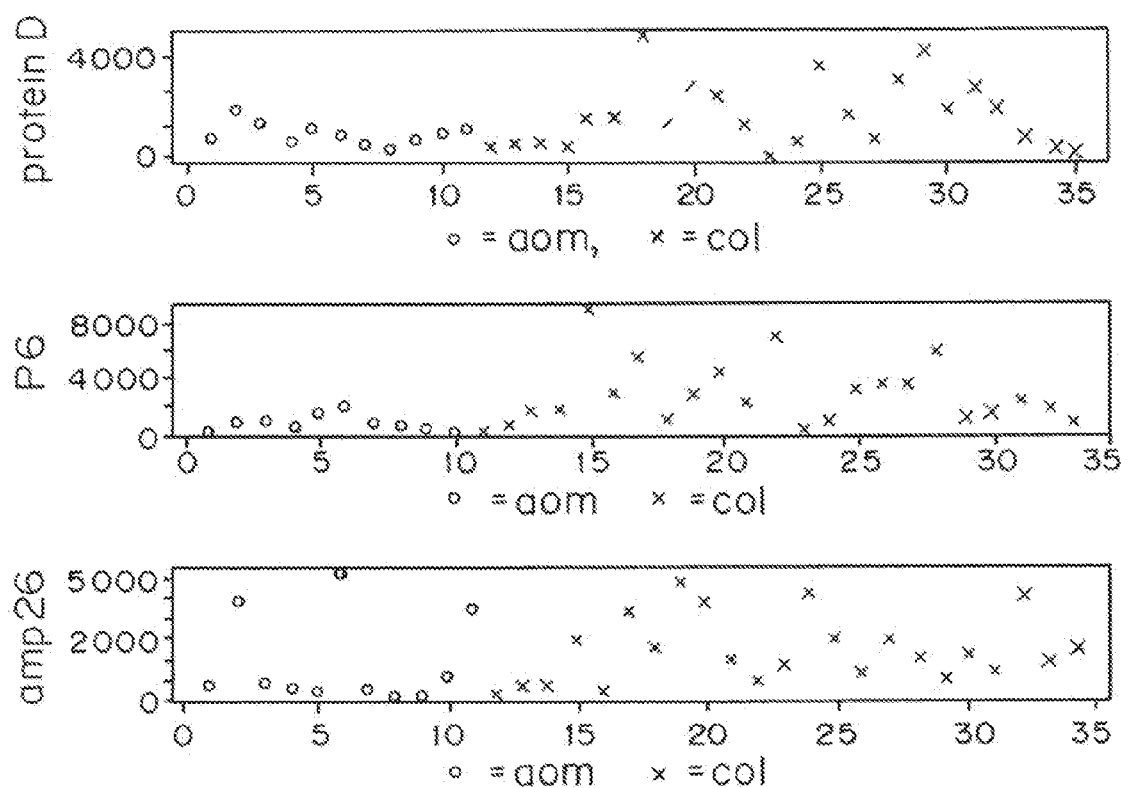
FIG. 12 is a comparison of convalescent serum IgG levels to NTHi outer membrane proteins D, P6 and OMP26 following an AOM or an NP colonization event. X-axis represents the number of cumulative data points. o=individual IgG level following an AOM event; x=individual IgG level following and NP colonization event.

FIG. 10 shows a boxplot of the measured serum antibodies to protein D, P6 and OMP26 at 6, 9, 12, 15, 18, 24, and 30 months of age corresponding to visits 1-7 for the study cohort. For comparison the antibody levels of 26 adults (age 18-60 years) are also displayed. The antibody levels increase significantly over time to all 3 NTHi proteins (p<0.001). Antibody levels among each of the 3 proteins at each of the 7 time points did not differ significantly. Compared to adults, antibody in the 24-30 month age groups combined was significantly lower than adults for protein D (p<0.001).

iii. Comparison of Serum Antibody Levels to Protein D, P6 and OMP26 in NP Colonized Versus Non-Colonized Children at Various Ages The level of antibody to protein D, P6 and OMP26 was compared in children who were NP culture-positive for NTHi at age 6, 9, 15, 18, and 24-30 months with children of the same age who were not NP culture-positive. The patterns were significantly different for the 3 proteins (FIG. 11). For protein D no difference was identified between colonized and non-colonized children at age 6 or 9 months, but a significant difference was shown at age 15, 18, and 24-30 months. For P6, a significant difference was identified between colonized and non-colonized children at age 6, 9 and 15 months, but the difference was no longer significant at age 18, and 24-30 months, largely because of wide variation in antibody quantity among those children. For OMP26, no difference was seen between colonized and non-colonized children.

iv. Comparison of Convalescent Serum IgG Levels to NTHi Outer Membrane Proteins D, P6 and OMP26 Following an AOM or an NP Colonization Event AOM events stimulate a high quantity of antibody to the studied proteins in convalescence. It is known that NP colonization is a necessary first step in pathogenesis for AOM. Therefore NP colonization plus an acute infection in the form of AOM can result in higher antibody levels than NP colonization only. Unexpectedly the levels of antibody to protein D, P6 and OMP26 following an AOM episode were determined to be generally low compared to those observed following NP colonization (FIG. 12). The lower AOM convalescent antibody levels compared to colonization convalescent antibody levels was significant for P6 (p<0.001) but not for protein D or OMP26. The analysis is complicated by the fact that the post AOM serum antibody levels were all obtained 3 weeks after an AOM event whereas the convalescent colonization antibody levels were obtained at the next scheduled visit for the child. Therefore a post colonization sample could have been obtained 3-6 months after the colonization event, at a time when some diminution of antibody likely occurred compared to the 3 weeks post AOM sampling. The differences in timing contributed to the variation in convalescent antibody levels after colonization.

v. Paired Acute and Convalescent Serum IgG, IgM and IgA Antibody Levels to NTHi Outer Membrane Proteins D, P6 and OMP26 in Children with AOM The quantity of total immunoglobulin to protein D (IgG+IgM+IgA) in acute sera at the time a child presented for clinical care for AOM was 2082 ng/mL, for P6 it was 1422 ng/mL, and for OMP26 it was 1545 ng/mL, p=0.18 for protein D vs. P6 (FIG. 13). In the convalescent serum, the quantity of total immunoglobulin to protein D was 2872 ng/mL, for P6 it was 1108 ng/mL, and for OMP26 it was 2264 ng/mL, p=0.04 for protein D vs. P6. The ratio of the three immunoglobulin classes (IgG to IgM to IgA) was not different for the 3 proteins. When assessed as a cohort the increases in IgG, IgM and IgA in acute vs. convalescent sera were not significant for any of the 3 proteins.

From the data displayed in FIG. 12 for all three proteins it appears that in the convalescent phase the antibody levels following AOM infection are not as high as after NP colonization and from FIG. 13 the acute to convalescent change in antibody concentration is not significant for the overall cohort. Therefore FIG. 5 shows the individual responses of children to all three proteins. When the individual responses were examined where paired sera were available it was observed that about one-third of children showed a rising antibody response to one or more of the NTHi antigens, with IgM predominating in acute sera (indicating a primary immune response), one-third had no change in antibody level between acute and convalescent sera, with IgG>IgM but relatively high IgM (indicating that a primary response was occurring but the sampling missed the true onset of the immune response) and one-third had a falling antibody level, with IgG_IgM (indicating that the samples were taken well past the onset of the primary immune response or that a secondary response had occurred). The absence of synchrony of the antibody responses to protein D, P6 and OMP26 is notable but at this time there are too few children to effectively analyze this effect (FIG. 14).

vi. Bactericidal Activity of NTHi Anti Protein D, P6 and OMP26 Antibodies

To evaluate the functionality of the antibodies detected by ELISA, bactericidal activity of the antibodies was assessed, specific to each protein. In Table 4a the concentration of protein D specific antibody determined by the ELISA and the bactericidal activity of the total antibody to the homologous infecting AOM strain is shown and compared to the concentrations and bactericidal titers after absorption of all or nearly all of the protein D specific antibody. For 7 of the 11 sera tested absorption of anti-protein D antibody resulted in a significant drop in bactericidal antibody. Table 4b shows the results for P6 (9 of 11 sera showed a drop) and Table 4c shows the results for OMP26 (0 of 11 showed a drop). The number of sera with bactericidal antibody to protein D was significantly greater than OMP26 (p=0.01) and the bactericidal antibody to P6 was significantly greater than OMP26 (p=0.001). Antibody to protein D and P6 accounted for all of the detected bactericidal antibody in 5 (45%) of 11 studied children and at least 50% of the bactericidal antibody in the remaining 6 children. To study the specificity of the cross absorption, P6 and OMP26 ELISA titers were quantified in sera that were absorbed to remove protein D antibodies; there was no cross absorption. Similar experiments in duplicate were done with each serum on two different occasions to verify the specificity of absorption for the antibodies studied.

TABLE 4a

Bactericidal activity of NTHi anti protein D antibodies

| Subjects | Anti PROTEIN D ELISA Ab titers (EU/mL) | Bactericidal titer* (pre adsorption) | Anti PROTEIN D ELISA Ab titers (post protein D-Ab adsorption) (EU/mL) | Bacterial titer* (with protein D adsorbed sera) |
|---|---|---|---|---|
| 1 | 1100 | 8 | 200 | 4 |
| 2 | 76 | 8 | 40 | 4 |
| 3 | 1500 | 16 | 100 | 8 |
| 4 | 780 | 16 | 187 | 4 |
| 5 | 773 | 8 | 291 | 8 |
| 6 | 1130 | 32 | <5 | 32 |

TABLE 4a-continued

Bactericidal activity of NTHi anti protein D antibodies

| Subjects | Anti PROTEIN D ELISA Ab titers (EU/mL) | Bactericidal titer* (pre adsorption) | Anti PROTEIN D ELISA Ab titers (post protein D-Ab adsorption) (EU/mL) | Bacterial titer* (with protein D adsorbed sera) |
|---|---|---|---|---|
| 7  | 1260 | 4  | <5  | 4  |
| 8  | 1275 | 64 | 150 | 32 |
| 9  | 5450 | 16 | <5  | 8  |
| 10 | 8326 | 8  | 495 | 8  |
| 11 | 213  | 8  | <5  | 4  |

TABLE 4b

Bactericidal activity of NTHi anti protein P6 antibodies

| Subjects | P6 ELISA Ab titers in sera (EU/mL) | Bacterial titer* (pre adsorption) | Anti P6 ELISA Ab titers in sera (post P6-Ab adsorption) (EU/mL) | Bacterial titer* (with P6 adsorbed sera) |
|---|---|---|---|---|
| 1  | 4531  | 8  | 124 | 4  |
| 2  | 180   | 8  | 91  | 4  |
| 3  | 199   | 16 | 127 | 8  |
| 4  | 1265  | 16 | 226 | 16 |
| 5  | 1160  | 8  | 192 | 4  |
| 6  | 632   | 32 | 174 | 8  |
| 7  | 933   | 4  | 38  | 0  |
| 8  | 1348  | 64 | 128 | 16 |
| 9  | >6000 | 16 | 40  | 16 |
| 10 | 1605  | 8  | 62  | 4  |
| 11 | 674   | 8  | 32  | 0  |

TABLE 4c

Bactericidal activity of NTHi anti OMP26 antibodies

| Subjects | Anti OMP26 Ab titers (EU/mL) | Bacterial titer* (pre adsorption) | Anti OMP26 Ab titers (post OMP26-Ab adsorption) (EU/mL) | Bacterial titer* (with OMP26 adsorbed sera) |
|---|---|---|---|---|
| 1  | 260  | 8  | <5  | 8  |
| 2  | 146  | 8  | <5  | 8  |
| 3  | 281  | 16 | <5  | 16 |
| 4  | 1110 | 16 | 265 | 16 |
| 5  | 207  | 8  | <5  | 8  |
| 6  | 267  | 32 | <5  | 32 |
| 7  | 1600 | 4  | 866 | 4  |
| 8  | 840  | 64 | <5  | 64 |
| 9  | 1800 | 16 | 172 | 16 |
| 10 | 1550 | 8  | 195 | 8  |
| 11 | 243  | 8  | <5  | 8  |

*Bactericidal titer values are expressed as a reciprocal titer of the dilution where 50% bacterial killing was achieved.

4. Discussion

The systemic antibody response in children who experience NTHi colonization and AOM has not been well characterized. Progress in the development of an NTHi vaccine to prevent AOM is hampered by our gaps in knowledge of the immune response mounted by children who experience NTHi NP colonization and AOM. Studies in the past often did not have the advantage of current microbiology, molecular biology and immunology techniques, the antibody repertoire and functionality of antibody was not fully assessed, and/or the diagnostic accuracy of AOM and differentiation of AOM from OME—a distinctly different clinical condition, was often not made [Shurin et al., J Pediatr 1980; 97(3):364-9; Novotny et al., Infect Immun 2000; 68(4):2119-28; Novotny et al., Vaccine 2002; 20(29-30):3590-7; Murphy T et al., J Clin Invest 1986; 78(4):1020-7; Harabuchi et al., J Infect Dis 1994; 170(4):862-6; Spinola et al., J Infect Dis 1986; 154(1):100-9; Faden et al., J Infect Dis 1995; 172(1):132-5; Sloyer et al., J Infect Dis 1975; 132(6):685-8; Faden et al., J Infect Dis 1989; 160(6):999-1004; Bernstein et al., Otolaryngol Head Neck Surg 1997; 116(3):363-71; Harabuchi et al., Acta Otolaryngol 1998; 118(6):826-32; Yamanaka and Faden, J Pediatr 1993; 122(2):212-8; Hotomi et al., Acta Otolaryngol 1999; 119(6):703-7; Sloyer et al., J Clin Microbiol 1976; 4(3):306-8; Faden et al., Infect Immun 1989; 57(11):3555-9; Yamanaka and Faden, Acta Otolaryngol 1993; 113(4):524-9; Bernstein et al., Otolaryngol Head Neck Surg 1991; 105(3):406-10].

NP colonization by otopathogens among children has been studied in a study design similar to ours in the past. Faden et al. [Faden et al., J Infect Dis 1995; 172:132-5] prospectively evaluated NP colonization by NTHi in a cohort of 200 children from birth to two years of age living in suburban Buffalo N.Y. NP colonization was detected in 44% of the children, with more frequent colonization detected in the first year of life compared to the second year of life. Frequent acquisition of NTHi strains with frequent clearing was observed in that study, similar to our findings. Faden et al. included children from birth to 6 months of age when colonization occurred relatively frequently and his group sampled the NP more often than we did in the first year of life. This may account for our detection rate of 28% of evaluated children compared to their study. Indeed, we did observe significant increases in serum antibody to one or more of the NTHi antigens we studied occurring between study visits, suggesting that NP colonization events occurred without detection due to NP sampling frequency.

Importantly, the gradual acquisition of serum antibody in children over time to vaccine candidate antigens protein D, P6 and OMP26 demonstrates that the 3 proteins are immunogenic in infants 6-30 months of age. Such an observation is strongly supportive of the potential of these antigens to be useful in a vaccine against NTHi infection in children. Previously, Akkoyunia et al. [Akkoyunia et al., Infect Immun 1996; 64:4586-92] evaluated naturally occurring protein D antibodies and found they were low in children below one year of age but rose between age 1 and 5 years. Yamanaka and Faden [Yamanaka and Faden, J Pediatr 1993; 122:212-8] prospectively studied the serum antibody levels to P6 in eight children at ages birth, 6 months, 1, 2, 4, 6, and 10 years old and eight adults. They found that levels increased over time and the difference became significant when 6 month olds were compared to four year olds.

It was previously reported that NP colonization appeared to be an immunizing event in children relative to P6 protein [Sabirov et al., Pediatr Res 2009; 66(5):565-70]. The significant difference in antibody level among NP colonized compared to uncolonized children beginning at age 15 months for protein D and 6 months for P6 provides further evidence that NP colonization with NTHi is associated with stimulation of serum antibody to OMPs expressed by this bacteria. The absence of a significant increase in antibody to OMP26 in NP colonized compared to uncolonized children was unexpected since a gradual and significant rise in antibody to OMP26 was observed to occur as children increased in age from 6 to 30 months old. This observation will require further study. Our findings are in contrast to those by Spinola et al. [Spinola et al., J Infect Dis 1986; 154(1):100-9], who prospectively followed 3 children who attended a single day care center from infancy until early childhood obtaining NP cultures periodically. They noted that NP colonization in children with NTHi was a dynamic process with loss and acquisition of different strains occurring over time. Serum IgG directed to the OMPs of NTHi did not appear to change greatly over time, or to be correlated with NP colonization. In a study evaluating pneumococcal NP colonization and AOM, Virolainen et al. [Virolainen et al., Pediatr Infect Dis J 1996; 15:128-33] evaluated serum antibodies in children with AOM to pneumolysin, a pneumococcal protein that is a vaccine candidate. Eight of 10 children experienced a seroconversion in pneumolysin antibody levels following AOM due to pneumococci at a median age of 20 months old. Similarly, Rapola et al. [Rapola et al., Pediatr Infect Dis J 2001; 20:482-7] studied the serum antibody response to pneumolysin and pneumococcal surface adhesion A (PsaA) in children with AOM age 2 months to 2 years. Antibody levels were compared among three groups: pneumococcal AOM, pneumococcal NP colonized and neither NP colonized nor AOM due to pneumococci. At the time of the sampling, children with NP colonization had the highest anti-PsaA antibody levels, children with a current AOM were next highest, children with no current but a past history of pneumococcal NP colonization or AOM were third highest, and lowest were those with no current or previous documented history of pneumococcal colonization or AOM. Wide variations in antibody levels were measured. The findings were similar with pneumolysin. Our study of NTHi antibody responses to protein D, P6 and OMP26 are in agreement with the studies of pneumococcal vaccine protein candidates. Age of the child and preexisting antibody levels are important covariates in predicting an antibody response to NP colonization. This may prove true also for vaccination.

The isotypes of antibody in acute and convalescent sera surrounding an AOM for the subset of children where there was paired serum, IgG antibody predominated although IgM antibody levels were also elevated. This repertoire of antibody is most consistent with prior priming of the immune response before the AOM; otherwise we would have expected IgM to predominate in acute sera and a switch in Ig class to occur in convalescent sera to IgG predominant Analysis of individual child data allowed us to observe that the cohort analysis masked differences in the antibody repertoire. The addition of more children to our study in the future may allow a clearer understanding of the proportion of children with various antibody response characteristics. In earlier work, Samukawa et al. [Samukawa et al., Infect Immun 2000; 68:1569-73] studied the immune response to S. pneumoniae surface proteinA (PspA) and M. catarrhalis OMP UspA in the sera of various age groups in the general population. In the first 2 years of life they found comparable amounts of IgG and IgM serum antibodies to both PspA and UspA whereas in adults IgG predominated. In contrast, when Virolainen et al. [Virolainen et al., Pediatr Infect Dis J 1996; 15:128-33] evaluated serum antibodies in children with AOM to pneumolysin they found eight of 10 children experienced a seroconversion in pneumolysin antibody levels, all of the IgA class only.

Not all antibody elicited by natural exposure to NTHi may be functional; therefore the study of the contribution of antibody to protein D, P6 and OMP26 to bactericidal activity was of interest. Serum bactericidal antibody is associated with protection from AOM caused by NTHi [Shurin et al., J Pediatr 1980; 97(3):364-9; Faden et al., J Infect Dis 1999; 160:999-1004]. Previous work has shown that serum bactericidal antibody to the homologous strain persists after AOM and can protect against recurrent NTHi AOM infection by the homologous strain but cross-protection for other (heterologous) strains generally is not induced [Shurin et al., J Pediatr 1980; 97(3):364-9; Faden et al., J Infect Dis 1999; 160:999-1004]. Forsgren has previously shown that antibody to protein D can be bactericidal [Forsgren et al., Clin Infect Dis 2008; 46:726-31]. Murphy et al. [Murphy et al., J Clin Invest 1986; 78(4):1020-7] assessed the role of P6 as a target of bactericidal antibody and showed that in a pool of 6 adult sera depletion of P6 antibodies resulted in a reduction bactericidal activity. The absence of a bactericidal effect by OMP26 has been noted [Cripps and Otczyk, Exp Rev Vaccines 2006; 5:517-34]. Therefore, the results are consistent with previous reports.

A significant correlation was not found between bactericidal titers and ELISA antibody concentrations for P6, protein D and OMP26 antibodies. Higher ELISA antibody titers did not consistently result in higher bactericidal titers. Particularly for OMP26 high ELISA antibody titers did not correlate with high bactericidal titers and the depletion of OMP26 specific antibodies did not change bactericidal titers. The disparity in antibody quantity measured by ELISA and bactericidal titers most likely is a reflection of the fact that ELISA measures antibody of low and high avidity whereas bactericidal titers largely reflect high avidity antibody [Pollard and Levin, Lancet 2000; 356(9247):2065-6; Maslanka et al., Infect Immun 1998; 66(6):2453-9]. Also it can be that not all OMPs expressed by NTHi elicit bactericidal antibodies.

The difficulty of obtaining blood from young children repetitively between 6 and 30 months of age is considerable, particularly when coupled with additional blood sampling for acute and convalescent levels surrounding an AOM. Therefore, despite best efforts, blood samples were not obtained from every child at every visit as designed. This created windows of missing data that were addressed statistically as possible, but the addition of more samples from more children is ongoing and may allow further light on some of the issues addressed in this report. The need to evaluate mucosal immune responses and cellular responses to NTHi NP colonization and AOM was recognized and to compare immune responses between children with absent or infrequent AOM with otitis prone children. Those studies are ongoing and will be reported subsequently. The study cohort is drawn from a predominantly high socioeconomic population in a developed country and therefore the results may not be generalizable to children in developing countries with lower socioeconomic status where the NP colonization frequency and bacterial load may be higher.

In conclusion, this is the first study to compare antibody levels to three NTHi candidate vaccine OMPs in children following asymptomatic NP colonization and episodes of AOM. Increasing levels of protein D, P6 and OMP26-specific IgG antibodies were found in children as they increased in age from 6 to 30 months of age. Increased antibody levels were specifically measured following detected NP colonization with NTHi for protein D and P6 but not OMP26. In convalescence from AOM children had lower overall IgG antibody levels than after asymptomatic NP colonization. Thus it appeared that AOM occurred in the context of a less robust immune response than following colonization. However the overall response did not reflect individual responses among the study cohort in that some children had a clear increase in antibody to protein D, P6 and/or OMP26 following AOM. Natural antibodies to protein D and P6 but not OMP26 elicited by NP colonization and AOM were bactericidal.

F. Example 6

Reduced Serum IgG Responses to Pneumococcal Antigens in Otitis Prone Children May be Due to Poor Memory B-Cell Generation 1. Introduction

*Streptococcus pneumoniae* (Spn) is one of the most common pathogens causing AOM [Casey et al., Pediatr. Infect. Dis. J. 2010; 29(4):304-9]. Studies in animal models, and in humans to some extent, suggest that immune correlates of protection from infection by Spn include memory $CD4^+$ T cells, B cells, neutralizing serum and mucosal antibody levels [Zhang et al., J. Infect. Dis. 2007; 195(8):1194-202; Snapper et al., Trends Immunol. 2001; 22(6):308-11; Weiser et al., Proc. Natl. Acad. Sci. U.S.A 2003; 100(7):4215-20]. It was recently established that otitis prone children have reduced frequencies of Spn and nontypeable *Haemophilus influenzae* (NTHi)-antigen-specific memory $CD4^+$ T cells in their circulation at the time of AOM and following nasopharyngeal (NP) colonization [Sharma et al., J Infect Dis. 2011; 204(4):645-653]. After natural infection and vaccination, robust memory T and B cell responses should be generated, with memory lymphocytes populating lymphoid and non-lymphoid sites, to provide long-term protection from re-infection [Pichichero, Pediatrics 2009; 124(6):1633-41]. Once generated on subsequent exposure to a pathogen, memory B cells can proliferate into antibody secreting cells (ASCs) and maintain serum antibody levels over a period of time [Lanzavecchia and Sallusto, Curr. Opin. Immunol. 2009; 21(3):298-304; Kelly et al., JAMA 2005; 294(23):3019-23].

Earlier reports describe that otitis prone children produce lower amounts of Spn and NTHi-antigen-specific antibodies and/or not to produce functional bactericidal antibodies in response to AOM and/or NP colonization [Faden, Eur. J. Pediatr. 2001; 160(7):407-13; Murphy and Yi, Ann. N.Y. Acad. Sci. 1997; 830:353-60; Kaur et al., Vaccine 2011; 29(5):1023-8]. These findings indicate that decreased concentrations of circulating antibodies to the otopathogens may contribute to the otitis prone condition. However, until this current work there has not been an evaluation of whether the observed reduction in the serum antibody in otitis prone children might be due to failure to generate robust antigen-specific memory B cells. This is the first report demonstrating that lower pathogen-specific memory B cell generation may account for lower antibody levels to protein antigens displayed by Spn among young children from recurrent episodes of AOM.

2. Methods i. Subjects

Subjects were participants from our 5-year prospective longitudinal AOM study funded by the NIH NIDCD [Kaur et al., Vaccine 2011; 29(5):1023-8]. Enrolled children were from a middle class, suburban socio-demographic population in Rochester N.Y. Healthy children at age of 6 months without prior AOM were enrolled and had blood, NP and oropharyngeal (OP) cultures obtained seven times, at the age of 6, 9, 12, 15, 18, 24 and 30 months. Middle ear fluid (MEF) was obtained by tympanocentesis during AOM episodes. Colonization with Spn and/or NTHi in the NP/OP was routinely determined by standard microbiologic culture. To identify the otitis prone child in the study population all the children had tympanocentesis-confirmed infections and all received antibiotic therapy directed to the otopathogen isolated from middle ear fluid for each AOM event. PBMCs were isolated from the collected blood and frozen in the liquid nitrogen until used. Children having three episodes of AOM within 6 months or 4 episodes within one year were considered otitis prone while others who had fewer episodes were placed into the non-otitis prone group. Written informal consent was obtained in association with a protocol approved by the Rochester General Hospital Investigational Review Board.

ii. Antigens

Five different pneumococcal protein antigens were used in this study: pneumococcal histidine triad proteins D (PhtD) and E (PhtE), LytB, PcpA, PlyD1 (a detoxified derivative of pneumolysin which has three point mutations that do not interfere with anti-pneumolysin antibody responses). All these antigens are pneumococcal vaccine candidate antigens.

iii. Humoral Responses

For measuring IgG antibody levels in the samples, ELISA was performed as described previously [Kaur et al., Vaccine 2011; 29(5):1023-8]. Briefly, 96-well ELISA plates (Nunc-Immulon) were coated with 0.5 ug/ml of individual antigens (100 μl/well) in coating buffer (bicarbonate, [pH 9.4]) and incubated overnight at 4° C. After washing, the plates were blocked with 3% skimmed milk at 37° C. for 1 hr (200 μl per well). After five washes, 100 μl of serum at a starting dilution of 1:100 (in PBS-3% skim milk) was added to the wells and diluted serially 2 fold. The mixture was incubated at room temperature for 1 hr followed by the addition of affinity purified goat anti-human IgG, IgM or IgA antibody conjugated to horseradish-peroxidase (Bethyl Laboratories, Inc, Montgomery, Tex.) as a secondary antibody. The reaction products were developed with TMB Microwell Peroxidase Substrate System (KPL, Gaithersburg, Md.), stopped by the addition of 1.0 molar phosphoric acid and read by an automated ELISA reader using a 450-nm filter. To provide quantitative results on antibody concentrations, the level of the specific antibody present in the unknown sample was determined by comparison to an internal reference serum (pool of human serum with high antigen titers). The levels of IgG in the reference serum were quantitatively measured by using a human IgG ELISA quantitation kit (Bethyl laboratories). A Four-parameter logistic-log function was used to form the reference and sample curves.

iv. Antibody Secreting Cells (ASCs) ELISPOT

Antigen-specific as well as total IgG secreting cells were quantified by an assay in which memory B cells were stimulated in vitro to differentiate into antibody-secreting cells (ASC) as standardized in the laboratory. Briefly, one million thawed PBMC were placed in each well of a 24-well plate containing 1 ml of complete media alone or complete media containing 1 μg/ml of pokeweed mitogen. Cells were kept at 37° C. for 3-days for differentiation, washed with complete media, counted and distributed onto overnight antigen-coated (10 μg/ml) 96-well ELISPOT plates (Millipore). Plasma cell differentiation was optimized with the help of flow cytometric evaluation of the differentiated cells (data not shown). For the detection of total IgG-secreting cells, wells were pre-coated with monoclonal anti-human IgG (MT91/145; Mabtech) at 10 ug/ml in PBS. As a negative control wells were left untreated or coated with same amount of bovine serum albumin (BSA). Plates were blocked with 10% FBS in RPMI 1640 for 30 min at 37° C. Stimulated PBMC were counted and $5 \times 10^5$ cells were resuspended in 200 μl of fresh complete RPMI media before distributing them onto control and antigen-coated wells. Plates were then incubated at 37° C. in a 5% $CO_2$ incubator overnight and then washed with PBS at least 5-times. Next, 100 μl of 1 μg/ml biotinylated anti-human IgG antibodies (MT78/145; Mabtech) were added to the wells and incubated for an hour. After washing streptavidin-alkaline phosphatase conjugate (1:1000) was added to the wells and incubated for an hour at 37° C. Plates were then washed 5-times with PBS before developing it with substrate (BCIP/NBT; Mabtech). Because of the low frequencies of antigen-specific ASCs, developed spots were manually counted with the help of dissection microscope. Ag specific data was expressed as a percentage of antigen-specific memory B-cells and was calculated per million of PBMC as follows: % Ag-specific MBC=(No. antigen-specific spots/No. of total Ig spots)×100.

v. Statistics

All data was analyzed using Graph Pad Prism software. Two tailed P values for the data were calculated using Mann Whitney Test.

3. Results i. Study Population

From a total study population of 387 children otitis prone children were identified. From the remainder children with 1 or 2 AOMs who were of a similar age as the non-otitis prone children were randomly selected to serve as controls. Clinical characteristics of the study children are shown in Table 5.

TABLE 5

Characteristics of study subjects

| | Otitis Prone (n = 10) | Non-Otitis Prone (n = 12) | P value |
|---|---|---|---|
| Gender | | | |
| Male | 6 | 7 | 1.00 |
| Female | 4 | 5 | 1.00 |
| Mean Age (mos) | 13.3 | 12.1 | 0.50 |
| # AOM Episodes | | | |
| ≥3 in 6 months | 5 | 0 | 0.01 |
| ≥4 in 12 months | 5 | 0 | 0.01 |
| Total number of AOM Episodes | | | |
| 1-3 | 3 | 4 | 1.00 |
| 4-5 | 6 | 0 | 0.003 |
| 6 or more | 1 | 0 | 0.45 |
| PET Insertion | 4 | 0 | 0.03 |
| Breast Feeding ≥6 months | 5 | 8 | 0.67 | ii. Generation of Pneumococcal Antigen-Specific Memory B-Cell is Reduced in Otitis Prone Children The circulating frequencies of various Spn antigen-specific memory B cells were compared between non-otitis prone and otitis prone children by stimulating their PBMCs with polycloncal stimulation. Antigen specific B cell responses were normalized with the control ELISPOT plate wells left uncoated or coated with BSA.

FIG. 18A demonstrates percentages of memory B cells to 5-Spn antigens in otitis prone children and non-otitis prone children caused by Spn. In sharp contrast, otitis prone children had a marked reduction of circulating Spn specific memory B cells after their AOM or NP colonization (Table 5). In particular, significantly lower percentages of memory B cells producing antigen-specific IgG were observed against antigens PhtD, PhtE and PlyD1 (P<0.02). Although otitis prone children showed an overall lower memory B cells generated to LytB, however the difference was not found significant (p=0.1). No difference was found in the memory B cells to PcpA in both otitis prone and non-otitis prone children (FIG. 18A). Similarly, total IgG-secreting cells were not different among both of the groups (data not shown).

iii. Otitis Prone Children have Reduced IgG Concentration to Pneumococcal Protein Antigens Antigen-specific IgG titers were evaluated in the serum of otitis prone and non-otitis prone children of matching age group. Serum IgG levels to Spn antigens in the respective groups are shown in FIG. 18B. In the cohort of non-otitis prone children IgG titers to PhtD, PcpA and PhtE were significantly higher compared to otitis prone (P<0.05), whereas PlyD1 levels were lower and not significantly different between the groups (FIG. 18B). Antibodies to LytB were lowest among all antigens tested in both of the cohorts (FIG. 18B).

4. Discussion

In this study, it was found that a reduced percentage of memory B cells circulating in the blood of otitis prone children following AOM and/or NP colonization (FIG. 18A). After encounter of antigen with naive B cells, antigen-specific memory B cells and antibody secreting cells are generated in the secondary lymphoid structures that transit through the blood to bone marrow, spleen, or target tissues such as respiratory tract [Kelly et al., JAMA 2005; 294(23):3019-23]. Since serum antibody levels are maintained by memory B cells [Bernasconi et al., Science 2002; 298(5600:2199-202], by analyzing the percentages of generated antigen-specific memory B cells a more precise immunological explanation for lower antibody levels in otitis prone children was provided. To confirm the association of lower frequencies of memory B cells with serum antibody levels we measured Spn-specific antibody titers and found they were significantly lower in otitis prone children (FIG. 18B).

Recently, it was demonstrated that otitis prone children have suboptimal pneumococcal antigen-specific memory $CD4^+$ T cell responses [Sharma et al., J Infect Dis. 2011; 204(4):645-653]. Findings from this study indicate that otitis prone children may develop some antibody responses since antibodies and memory B cells were detectable among these children after AOM and NP colonization with otopathogens (FIG. 18A-B). However, in the absence of antigen-specific memory B cell generation as well as adequate help from memory $CD4^+$ T cells, the antibody levels wane and otitis prone children are unable to maintain adequate serum antibody levels and get frequent repeat infections.

Pneumococcal polysaccharide-conjugate vaccination is helpful in boosting protective levels of anti-polysaccharide antibodies [Barnett et al., Clin. Infect. Dis. 1999; 29(1):191-2]; however serotype variation limits the protective efficacy of strain specific anti-polysaccharide antibodies [Casey et al., Pediatr. Infect. Dis. J. 2010; 29(4):304-9]. Moreover, despite of the fact that otitis prone children can induce serotype specific antibodies to conjugate vaccines, repeated infections are common among this vulnerable group [Barnett et al., Clin. Infect. Dis. 1999; 29(1):191-2], indicating that serotype-neutralizing immunity is brief and incomplete.

Interestingly, it was found that the percentage of circulating PhtD specific memory B-cells correlated with serum PhtD levels (FIG. 18C). A difference in the percentages of antigen-specific B cells and serum antibodies levels to PcpA and PlyD1 was observed (FIG. 18A-B). It is possible that (1) by binding to the circulating IgG, an active state of NP colonization or AOM infection may affect the detection of serum antibody levels as opposed to memory B cells, and (2) during infection in the uncontrolled inflammatory environment of NP, a different dose of pathogen antigen and PAMPs stimulation may elicit variable frequencies of B cell differentiation into ASCs and thus affect serum IgG levels even in the presence of memory B cells.

In conclusion, the memory B cell data indicate that otitis prone children have a significantly lower memory B cell generation that can differentiate into antibody secreting cells. The clinical relevance of the finding is clear. Antigen specific memory B cells act as reservoirs for serum antibody maintenance that upon antigen re-encounter can proliferate into ASCs leading to an increase in the serum antibody levels. It was found that otitis prone children do not lack total IgG-secreting cells. Furthermore the flow cytometry results showed that in response to polyclonal stimulation, otitis prone children do not have mechanistic dysfunction in the transformation of memory B cells (CD19+IgD−) to antibody secreting plasma-cells (CD27+CD38+CD138+) (data not shown). Whether naive B cells in the secondary lymphoid organs of otitis prone children are unable to get optimal CD4+ T-cells or T-follicular cell help for differentiation into memory B cells and/or ASCs for eventually maintaining higher serum IgG levels is currently being investigate.

is a child, wherein the vaccine elicits an effective immune response to Hi when administered to otitis prone children.

2. The method of claim 1, wherein the vaccine is administered through an oral route or intraperitoneal route.

3. The method of claim 1, wherein the vaccine is administered in capsular form.

4. The method of claim 1, wherein the vaccine is administered at a dosage ranging from 0.01 mg/ml/kg to 100 mg/ml/kg.

5. The method of claim 1, wherein the vaccine is capable of inhibiting a *Haemophilus influenzae* (Hi) infection in a subject prone to Hi to a greater extent than a vaccine comprising Protein D or OMP26.

6. The method of claim 1, wherein the vaccine is in a deliverable form.

7. The method of claim 1, wherein the vaccine comprises the P6 antigen and Protein D, epitopes of P5, Protein D, or mixtures thereof, but not OMP26 of non typeable *Haemophilus influenzae* (NTHi).

8. The method of claim 7, wherein the vaccine consists of P6 or P6 epitopes.

We claim:

1. A method of vaccination for preventing infections caused by the Gram negative bacteria *Haemophilus influenzae* (Hi) in otitis prone children, the method comprising administering a therapeutically effective dose of a vaccine comprising a P6 antigen to a subject, wherein the subject 9. The method of claim 1, wherein the vaccine further comprises a pharmaceutical carrier for administration to a subject.

10. The method of claim 1, wherein the P6 antigen in the vaccine is at a concentration of at least 1.1, 1.2, 1.3, 1.5, 1.7, 1.9, 2.0, 2.5, 3.0, 5, 7, or 10 fold the P6 antigen of a vaccine having P6, protein D, and OMP24 present.

11. The method of claim 1, wherein the vaccine induces a Th1 immune response.

12. The method of claim 1, wherein the vaccine downregulates NLRP3, PAFt, or IL1B, upregulates IL6, CCL3, CCL4, or downstream signaling of TLR2 and TLR4, or combinations thereof.

* * * * *